United States Patent
Woon et al.

(10) Patent No.: US 7,575,920 B2
(45) Date of Patent: Aug. 18, 2009

(54) YEAST EXPRESSION VECTORS FOR PRODUCTION OF ITF

(75) Inventors: Chee-Wai Woon, Worcester, MA (US); Nicholas P. Barker, Southborough, MA (US)

(73) Assignee: The GI Company, Inc., Framingham, MA (US)

( * ) Notice: Subject to any disclaimer, the term of this patent is extended or adjusted under 35 U.S.C. 154(b) by 0 days.

(21) Appl. No.: 11/493,791

(22) Filed: Jul. 25, 2006

(65) Prior Publication Data

US 2007/0148733 A1    Jun. 28, 2007

Related U.S. Application Data

(60) Provisional application No. 60/702,583, filed on Jul. 25, 2005.

(51) Int. Cl.
*C12N 15/00*    (2006.01)
*C07H 21/02*    (2006.01)

(52) U.S. Cl. .................................. 435/320.1; 536/23.1

(58) Field of Classification Search .................. None
See application file for complete search history.

(56) References Cited

U.S. PATENT DOCUMENTS

2003/0208057 A1*    11/2003    Lewin et al. ................ 536/23.2

FOREIGN PATENT DOCUMENTS

WO    84/04330    *    11/1984

WO    2005/042010    *    5/2005

OTHER PUBLICATIONS

Egel-Mitani et al. 1987; Nucleotide sequence of the gene encoding the *Saccharomyces kluyveri* mating factor pheromone. Nucleic Acids Res. 15(15): 6303-6304.*
Campbell et al. Mar. 2003; Embl AY264844.*
Mashimo et al. 1995; Structure and expression of murine intestinal trefoil factor: High evolutionary conservation and postnatal expression. Biochem. Biophys. Res. Commun. 210(1): 31-37.*
Kanai et al. 1998; Intestinal trefoil induces inactivation of extracellular signal-regulated protein kinase in intestinal epithelial cells. PNAS 95: 178-182.*
PIC9 manual from Invitrogen.*
Thim et al. 1993; Purification and characterization of the trefoil peptide human spasmolytic polypeptide (hSP) produced in yeast. FEBS Letters 318 (3): 345-352.*
Hagenbuchle et al. 1981; Mouse liver and salivary gland a-amylase mRNAs differ only in the 5' non-translated sequences. Nature 289:643-646.*
Eurwilaichitr et al., "Glutamic Acid and Alanine Spacer is Not Necessary for Removal of MFα-1 Signal Sequence Fused to the Human Growth Hormone Produced from *Pichia pastoris*," *World J. Micro. Biotech.* 18:493-498 (2002).
Thim et al., "Characterization of Human and Rat Intestinal Trefoil Factor Produced In Yeast," *Biochemistry* 34:4757-4764 (1995).
International Search Report and Written Opinion, mailed Apr. 9, 2008 (PCT/US06/28795).

* cited by examiner

*Primary Examiner*—Karen Cochrane Carlson
(74) *Attorney, Agent, or Firm*—Clark & Elbing LLP

(57) ABSTRACT

The invention features ITF expression vectors and methods of producing ITF.

2 Claims, 59 Drawing Sheets

FIGURE 4

Sequence of pPIC9

(SEQ ID NO: 1)

AGATCTAACATCCAAAGACGAAAGGTTGAATGAAACCTTTTTGCCATCCGACATCCACAGGTCCATTCTC
ACACATAAGTGCCAAACGCAACAGGAGGGGATACACTAGCAGCAGACCGTTGCAAACGCAGGACCTCCAC
TCCTCTTCTCCTCAACACCCACTTTTGCCATCGAAAAACCAGCCCAGTTATTGGGCTTGATTGGAGCTCG
CTCATTCCAATTCCTTCTATTAGGCTACTAACACCATGACTTTATTAGCCTGTCTATCCTGGCCCCCTG
GCGAGGTTCATGTTTGTTTATTTCCGAATGCAACAAGCTCCGCATTACACCCGAACATCACTCCAGATGA
GGGCTTTCTGAGTGTGGGGTCAAATAGTTTCATGTTCCCCAAATGGCCCAAAACTGACAGTTTAAACGCT
GTCTTGGAACCTAATATGACAAAAGCGTGATCTCATCCAAGATGAACTAAGTTTGGTTCGTTGAAATGCT
AACGGCCAGTTGGTCAAAAAGAAACTTCCAAAAGTCGCCATACCGTTTGTCTTGTTTGGTATTGATTGAC
GAATGCTCAAAAATAATCTCATTAATGCTTAGCGCAGTCTCTCTATCGCTTCTGAACCCCGGTGCACCTG
TGCCGAAACGCAAATGGGGAAACACCCGCTTTTTGGATGATTATGCATTGTCTCCACATTGTATGCTTCC
AAGATTCTGGTGGGAATACTGCTGATAGCCTAACGTTCATGATCAAAATTTAACTGTTCTAACCCCTACT
TGACAGCAATATATAAACAGAAGGAAGCTGCCCTGTCTTAAACCTTTTTTTTTATCATCATTATTAGCTT
ACTTTCATAATTGCGACTGGTTCCAATTGACAAGCTTTTGATTTAACGACTTTTAACGACAACTTGAGA
AGATCAAAAAACAACTAATTATTCGAAGGATCCAAACGATGAGATTTCCTTCAATTTTTACTGCAGTTTT
ATTCGCAGCATCCTCCGCATTAGCTGCTCCAGTCAACACTACAACAGAAGATGAAACGGCACAAATTCCG
GCTGAAGCTGTCATCGGTTACTCAGATTTAGAAGGGGATTTCGATGTTGCTGTTTTGCCATTTTCCAACA
GCACAAATAACGGGTTATTGTTTATAAATACTACTATTGCCAGCATTGCTGCTAAAGAAGAAGGGGTATC
TCTCGAGAAAAGAGAGGCTGAAGCTTACGTAGAATTCCCTAGGGCGGCCGCGAATTAATTCGCCTTAGAC
ATGACTGTTCCTCAGTTCAAGTTGGGCACTTACGAGAAGACCGGTCTTGCTAGATTCTAATCAAGAGGAT
GTCAGAATGCCATTTGCCTGAGAGATGCAGGCTTCATTTTTGATACTTTTTTATTTGTAACCTATATAGT
ATAGGATTTTTTTTGTCATTTTGTTTCTTCTCGTACGAGCTTGCTCCTGATCAGCCTATCTCGCAGCTGA
TGAATATCTTGTGGTAGGGGTTTGGGAAAATCATTCGAGTTTGATGTTTTTCTTGGTATTTCCCACTCCT
CTTCAGAGTACAGAAGATTAAGTGAGAAGTTCGTTTGTGCAAGCTTATCGATAAGCTTTAATGCGGTAGT
TTATCACAGTTAAATTGCTAACGCAGTCAGGCACCGTGTATGAAATCTAACAATGCGCTCATCGTCATCC
TCGGCACCGTCACCCTGGATGCTGTAGGCATAGGCTTGGTTATGCCGGTACTGCCGGGCCTCTTGCGGGA
TATCGTCCATTCCGACAGCATCGCCAGTCACTATGGCGTGCTGCTAGCGCTATATGCGTTGATGCAATTT
CTATGCGCACCCGTTCTCGGAGCACTGTCCGACCGCTTTGGCCGCCGCCCAGTCCTGCTCGCTTCGCTAC
TTGGAGCCACTATCGACTACGCGATCATGGCGACCACACCCGTCCTGTGGATCTATCGAATCTAAATGTA
AGTTAAAATCTCTAAATAATTAAATAAGTCCCAGTTTCTCCATACGAACCTTAACAGCATTGCGGTGAGC
ATCTAGACCTTCAACAGCAGCCAGATCCATCACTGCTTGGCCAATATGTTTCAGTCCCTCAGGAGTTACG
TCTTGTGAAGTGATGAACTTCTGGAAGGTTGCAGTGTTAACTCCGCTGTATTGACGGGCATATCCGTACG
TTGGCAAAGTGTGGTTGGTACCGGAGGAGTAATCTCCACAACTCTCTGGAGAGTAGGCACCAACAAACAC
AGATCCAGCGTGTTGTACTTGATCAACATAAGAAGAAGCATTCTCGATTTGCAGGATCAAGTGTTCAGGA
GCGTACTGATTGGACATTTCCAAAGCCTGCTCGTAGGTTGCAACCGATAGGGTTGTAGAGTGTGCAATAC
ACTTGCGTACAATTTCAACCCTTGGCAACTGCACAGCTTGGTTGTGAACAGCATCTTCAATTCTGGCAAG
CTCCTTGTCTGTCATATCGACAGCCAACAGAATCACCTGGGAATCAATACCATGTTCAGCTTGAGACAGA
AGGTCTGAGGCAACGAAATCTGGATCAGCGTATTTATCAGCAATAACTAGAACTTCAGAAGGCCCAGCAG
GCATGTCAATACTACACAGGGCTGATGTGTCATTTGAACCATCATCTTGGCAGCAGTAACGAACTGGTT
TCCTGGACCAAATATTTTGTCACACTTAGGAACAGTTTCTGTTCCGTAAGCCATAGCAGCTACTGCCTGG
GCGCCTCCTGCTAGCACGATACACTTAGCACCAACCTTGTGGGCAACGTAGATGACTTCTGGGGTAAGGG
TACCATCCTTCTTAGGTGGAGATGCAAAAACAATTTCTTTGCAACCAGCAACTTTGGCAGGAACACCCAG
CATCAGGGAAGTGGAAGGCAGAATTGCGGTTCCACCAGGAATATAGAGGCCAACTTTCTCAATAGGTCTT
GCAAAACGAGAGCAGACTACACCAGGGCAAGTCTCAACTTGCAACGTCTCCGTTAGTTGAGCTTCATGGA
ATTTCCTGACGTTATCTATAGAGAGATCAATGGCTCTCTTAACGTTATCTGGCAATTGCATAAGTTCCTC
TGGGAAAGGAGCTTCTAACACAGGTGTCTTCAAAGCGACTCCATCAAACTTGGCAGTTAGTTCTAAAAGG
GCTTTGTCACCATTTTGACGAACATTGTCGACAATTGGTTTGACTAATTCCATAATCTGTTCCGTTTTCT
GGATAGGACGACGAAGGGCATCTTCAATTTCTTGTGAGGAGGCCTTAGAAACGTCAATTTTGCACAATTC
AATACGACCTTCAGAAGGGACTTCTTTAGGTTTGGATTCTTCTTTAGGTTGTTCCTTGGTGTATCCTGGC

FIGURE 4, cont.

```
TTGGCATCTCCTTTCCTTCTAGTGACCTTTAGGGACTTCATATCCAGGTTTCTCTCCACCTCGTCCAACG
TCACACCGTACTTGGCACATCTAACTAATGCAAAATAAAATAAGTCAGCACATTCCCAGGCTATATCTTC
CTTGGATTTAGCTTCTGCAAGTTCATCAGCTTCCTCCCTAATTTTAGCGTTCAACAAAACTTCGTCGTCA
AATAACCGTTTGGTATAAGAACCTTCTGGAGCATTGCTCTTACGATCCCACAAGGTGGCTTCCATGGCTC
TAAGACCCTTTGATTGGCCAAAACAGGAAGTGCGTTCCAAGTGACAGAAACCAACACCTGTTTGTTCAAC
CACAAATTTCAAGCAGTCTCCATCACAATCCAATTCGATACCCAGCAACTTTTGAGTTGCTCCAGATGTA
GCACCTTTATACCACAAACCGTGACGACGAGATTGGTAGACTCCAGTTTGTGTCCTTATAGCCTCCGGAA
TAGACTTTTTGGACGAGTACACCAGGCCCAACGAGTAATTAGAAGAGTCAGCCACCAAAGTAGTGAATAG
ACCATCGGGGCGGTCAGTAGTCAAAGACGCCAACAAAATTTCACTGACAGGGAACTTTTTGACATCTTCA
GAAAGTTCGTATTCAGTAGTCAATTGCCGAGCATCAATAATGGGGATTATACCAGAAGCAACAGTGGAAG
TCACATCTACCAACTTTGCGGTCTCAGAAAAGCATAAACAGTTCTACTACCGCCATTAGTGAAACTTTT
CAAATCGCCCAGTGGAGAAGAAAAAGGCACAGCGATACTAGCATTAGCGGGCAAGGATGCAACTTTATCA
ACCAGGGTCCTATAGATAACCCTAGCGCCTGGGATCATCCTTTGGACAACTCTTTCTGCCAAATCTAGGT
CCAAAATCACTTCATTGATACCATTATTGTACAACTTGAGCAAGTTGTCGATCAGCTCCTCAAATTGGTC
CTCTGTAACGGATGACTCAACTTGCACATTAACTTGAAGCTCAGTCGATTGAGTGAACTTGATCAGGTTG
TGCAGCTGGTCAGCAGCATAGGGAAACACGGCTTTTCCTACCAAACTCAAGGAATTATCAAACTCTGCAA
CACTTGCGTATGCAGGTAGCAAGGGAAATGTCATACTTGAAGTCGGACAGTGAGTGTAGTCTTGAGAAAT
TCTGAAGCCGTATTTTTATTATCAGTGAGTCAGTCATCAGGAGATCCTCTACGCCGGACGCATCGTGGCC
GGCATCACCGGCGCCACAGGTGCGGTTGCTGGCGCCTATATCGCCGACATCACCGATGGGGAAGATCGGG
CTCGCCACTTCGGGCTCATGAGCGCTTGTTTCGGCGTGGGTATGGTGGCAGGCCCCGTGGCCGGGGGACT
GTTGGGCGCCATCTCCTTGCATGCACCATTCCTTGCGGCGGCGGTGCTCAACGGCCTCAACCTACTACTG
GGCTGCTTCCTAATGCAGGAGTCGCATAAGGGAGAGCGTCGAGTATCTATGATTGGAAGTATGGGAATGG
TGATACCCGCATTCTTCAGTGTCTTGAGGTCTCCTATCAGATTATGCCCAACTAAAGCAACCGGAGGAGG
AGATTTCATGGTAAATTTCTCTGACTTTTGGTCATCAGTAGACTCGAACTGTGAGACTATCTCGGTTATG
ACAGCAGAAATGTCCTTCTTGGAGACAGTAAATGAAGTCCCACCAATAAAGAAATCCTTGTTATCAGGAA
CAAACTTCTTGTTTCGAACTTTTTCGGTGCCTTGAACTATAAAATGTAGAGTGGATATGTCGGGTAGGAA
TGGAGCGGGCAAATGCTTACCTTCTGGACCTTCAAGAGGTATGTAGGGTTTGTAGATACTGATGCCAACT
TCAGTGACAACGTTGCTATTTCGTTCAAACCATTCCGAATCCAGAGAAATCAAAGTTGTTTGTCTACTAT
TGATCCAAGCCAGTGCGGTCTTGAAACTGACAATAGTGTGCTCGTGTTTTGAGGTCATCTTTGTATGAAT
AAATCTAGTCTTTGATCTAAATAATCTTGACGAGCCAAGGCGATAAATACCCAAATCTAAAACTCTTTTA
AAACGTTAAAAGGACAAGTATGTCTGCCTGTATTAAACCCCAAATCAGCTCGTAGTCTGATCCTCATCAA
CTTGAGGGGCACTATCTTGTTTTAGAGAAATTTGCGGAGATGCGATATCGAGAAAAAGGTACGCTGATTT
TAAACGTGAAATTTATCTCAAGATCTCTGCCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCCGTCAGGGCGC
GTCAGCGGGTGTTGGCGGGTGTCGGGGCGCAGCCATGACCCAGTCACGTAGCGATAGCGGAGTGTATACT
GGCTTAACTATGCGGCATCAGAGCAGATTGTACTGAGAGTGCACCATATGCGGTGTGAAATACCGCACAG
ATGCGTAAGGAGAAAATACCGCATCAGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCCGCGTTGCTGGC
GTTTTTCCATAGGCTCCGCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCAATGCTCACGCTG
TAGGTATCTCAGTTCGGTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTTCACCTAGATCCTT
TTAAATTAAAAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCA
CGCTCACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAGTTAA
TAGTTTGCGCAACGTTGTTGCCATTGCTGCAGGCATCGTGGTGTCACGCTCGTCGTTTGGTATGGCTTCA
TTCAGCTCCGGTTCCCAACGATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCACTCATGGTTATGGCAGCACT
```

FIGURE 4, cont.
GCATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAACACGGGATAATACCGCGCCAC
ATAGCAGAACTTTAAAAGTGCTCATCATTGGAAAACGTTCTTCGGGGCGAAAACTCTCAAGGATCTTACC
GCTGTTGAGATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAAGGGAATAAGGGCGACACGGAAAT
GTTGAATACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAAAGTGCCA
CCTGACGTCTAAGAAACCATTATTATCATGACATTAACCTATAAAAATAGGCGTATCACGAGGCCCTTTC
GTCTTCAAGAATTAATTCTCATGTTTGACAGCTTATCATCGATAAGCTGACTCATGTTGGTATTGTGAAA
TAGACGCAGATCGGGAACACTGAAAAATAACAGTTATTATTCG

FIGURE 5

Sequence of pPICGIco (SEQ ID NO: 2)

```
AGATCTAACATCCAAAGACGAAAGGTTGAATGAAACCTTTTTGCCATCCGACATCCACAGGTCCATTCTC
ACACATAAGTGCCAAACGCAACAGGAGGGGATACACTAGCAGCAGACCGTTGCAAACGCAGGACCTCCAC
TCCTCTTCTCCTCAACACCCACTTTTGCCATCGAAAAACCAGCCCAGTTATTGGGCTTGATTGGAGCTCG
CTCATTCCAATTCCTTCTATTAGGCTACTAACACCATGACTTTATTAGCCTGTCTATCCTGGCCCCCCTG
GCGAGGTTCATGTTTGTTTATTTCCGAATGCAACAAGCTCCGCATTACACCCGAACATCACTCCAGATGA
GGGCTTTCTGAGTGTGGGGTCAAATAGTTTCATGTTCCCCAAATGGCCCAAAACTGACAGTTTAAACGCT
GTCTTGGAACCTAATATGACAAAAGCGTGATCTCATCCAAGATGAACTAAGTTTGGTTCGTTGAAATGCT
AACGGCCAGTTGGTCAAAAAGAAACTTCCAAAAGTCGCCATACCGTTTGTCTTGTTTGGTATTGATTGAC
GAATGCTCAAAAATAATCTCATTAATGCTTAGCGCAGTCTCTATCGCTTCTGAACCCCGGTGCACCTG
TGCCGAAACGCAAATGGGGAAACACCCGCTTTTTGGATGATTATGCATTGTCTCCACATTGTATGCTTCC
AAGATTCTGGTGGGAATACTGCTGATAGCCTAACGTTCATGATCAAAATTTAACTGTTCTAACCCCTACT
TGACAGCAATATATAAACAGAAGGAAGCTGCCCTGTCTTAAACCTTTTTTTTTATCATCATTATTAGCTT
ACTTTCATAATTGCGACTGGTTCCAATTGACAAGCTTTTGATTTTAACGACTTTTAACGACAACTTGAGA
AGATCAAAAAACAACTAATTATTCGAAGGATCCAAACGATGAGATTTCCTTCAATTTTTACTGCAGTTTT
ATTCGCAGCATCCTCCGCATTAGCTGCTCCAGTCAACACTACAACAGAAGATGAAACGGCACAAATTCCG
GCTGAAGCTGTCATCGGTTACTCAGATTTAGAAGGGGATTTCGATGTTGCTGTTTTGCCATTTTCCAACA
GCACAAATAACGGGTTATTGTTTATAAATACTACTATTGCCAGCATTGCTGCTAAAGAAGAAGGGGTATC
TCTCGAGTAGAATTCCCTAGGGCGGCCGCGAATTAATTCGCCTTAGACATGACTGTTCCTCAGTTCAAGTT
GGGCACTTACGAGAAGACCGGTCTTGCTAGATTCTAATCAAGAGGATGTCAGAATGCCATTTGCCTGAGAG
ATGCAGGCTTCATTTTTGATACTTTTTTATTTGTAACCTATATAGTATAGGATTTTTTTTGTCATTTTGTT
TCTTCTCGTACGAGCTTGCTCCTGATCAGCCTATCTCGCAGCTGATGAATATCTTGTGGTAGGGGTTTGGG
AAAATCATTCGAGTTTGATGTTTTTCTTGGTATTTCCCACTCCTCTTCAGAGTACAGAAGATTAAGTGAGA
AGTTCGTTTGTGCAAGCTTATCGATAAGCTTTAATGCGGTAGTTTATCACAGTTAAATTGCTAACGCAGTC
AGGCACCGTGTATGAAATCTAACAATGCGCTCATCGTCATCCTCGGCACCGTCACCCTGGATGCTGTAGGC
ATAGGCTTGGTTATGCCGGTACTGCCGGGCCTCTTGCGGGATATCGTCCATTCCGACAGCATCGCCAGTCA
CTATGGCGTGCTGCTAGCGCTATATGCGTTGATGCAATTTCTATGCGCACCCGTTCTCGGAGCACTGTCCG
ACCGCTTTGGCCGCCGCCCAGTCCTGCTCGCTTCGCTACTTGGAGCCACTATCGACTACGCGATCATGGCG
ACCACACCCGTCCTGTGGATCTATCGAATCTAAATGTAAGTTAAAATCTCTAAATAATTAAATAAGTCCCA
GTTTCTCCATACGAACCTTAACAGCATTGCGGTGAGCATCTAGACCTTAACAGCAGCCAGATCCATCACT
GCTTGGCCAATATGTTTCAGTCCCTCAGGAGTTACGTCTTGTGAAGTGATGAACTTCTGGAAGGTTGCAGT
GTTAACTCCGCTGTATTGACGGGCATATCCGTACGTTGGCAAAGTGTGGTTGGTACCGGAGGAGTAATCTC
CACAACTCTCTGGAGAGTAGGCACCAACAAACACAGATCCAGCGTGTTGTACTTGATCAACATAAGAAGAA
GCATTCTCGATTTGCAGGATCAAGTGTTCAGGAGCGTACTGATTGGACATTTCCAAAGCCTGCTCGTAGGT
TGCAACCGATAGGGTTGTAGAGTGTGCAATACACTTGCGTACAATTTCAACCCTTGGCAACTGCACAGCTT
GGTTGTGAACAGCATCTTCAATTCTGGCAAGCTCCTTGTCTGTCATATCGACAGCCAACAGAATCACCTGG
GAATCAATACCATGTTCAGCTTGAGACAGAAGGTCTGAGGCAACGAAATCTGGATCAGCGTATTTATCAGC
AATAACTAGAACTTCAGAAGGCCCAGCAGGCATGTCAATACTACACAGGGCTGATGTGTCATTTTGAACCA
TCATCTTGGCAGCAGTAACGAACTGGTTTCCTGGACCAAATATTTTGTCACACTTAGGAACAGTTTCTGTT
CCGTAAGCCATAGCAGCTACTGCCTGGGCGCCTCCTGCTAGCACGATACACTTAGCACCAACCTTGTGGGC
AACGTAGATGACTTCTGGGGTAAGGGTACCATCCTTCTTAGGTGGAGATGCAAAAACAATTTCTTTGCAAC
CAGCAACTTTGGCAGGAACACCCAGCATCAGGGAAGTGGAAGGCAGAATTGCGGTTCCACCAGGAATATAG
AGGCCAACTTTCTCAATAGGTCTTGCAAAACGAGAGCAGACTACACCAGGGCAAGTCTCAACTTGCAACGT
CTCCGTTAGTTGAGCTTCATGGAATTTCCTGACGTTATCTATAGAGAGATCAATGGCTCTCTTAACGTTAT
CTGGCAATTGCATAAGTTCCTCTGGGAAAGGAGCTTCTAACACAGGTGTCTTCAAAGCGACTCCATCAAAC
TTGGCAGTTAGTTCTAAAAGGGCTTTGTCACCATTTTGACGAACATTGTCGACAATTGGTTTGACTAATTC
CATAATCTGTTCCGTTTTCTGGATAGGACGACGAAGGGCATCTTCAATTTCTTGTGAGGAGGCCTTAGAAA
CGTCAATTTTGCACAATTCAATACGACCTTCAGAAGGGACTTCTTTAGGTTTGGATTCTTCTTTAGGTTGT
TCCTTGGTGTATCCTGGCTTGGCATCTCCTTTCCTTCTAGTGACCTTTAGGGACTTCATATCCAGGTTTCT
```

FIGURE 5, cont.

```
CTCCACCTCGTCCAACGTCACACCGTACTTGGCACATCTAACTAATGCAAAATAAAATAAGTCAGCACATT
CCCAGGCTATATCTTCCTTGGATTTAGCTTCTGCAAGTTCATCAGCTTCCTCCCTAATTTTAGCGTTCAAC
AAAACTTCGTCGTCAAATAACCGTTTGGTATAAGAACCTTCTGGAGCATTGCTCTTACGATCCCACAAGGT
GGCTTCCATGGCTCTAAGACCCTTTGATTGGCCAAAACAGGAAGTGCGTTCCAAGTGACAGAAACCAACAC
CTGTTTGTTCAACCACAAATTTCAAGCAGTCTCCATCACAATCCAATTCGATACCCAGCAACTTTTGAGTT
GCTCCAGATGTAGCACCTTTATACCACAAACCGTGACGACGAGATTGGTAGACTCCAGTTTGTGTCCTTAT
AGCCTCCGGAATAGACTTTTTGGACGAGTACACCAGGCCCAACGAGTAATTAGAAGAGTCAGCCACCAAAG
TAGTGAATAGACCATCGGGGCGGTCAGTAGTCAAAGACGCCAACAAAATTTCACTGACAGGGAACTTTTG
ACATCTTCAGAAAGTTCGTATTCAGTAGTCAATTGCCGAGCATCAATAATGGGGATTATACCAGAAGCAAC
AGTGGAAGTCACATCTACCAACTTTGCGGTCTCAGAAAAAGCATAAACAGTTCTACTACCGCCATTAGTGA
AACTTTTCAAATCGCCCAGTGGAGAAGAAAAAGGCACAGCGATACTAGCATTAGCGGGCAAGGATGCAACT
TTATCAACCAGGGTCCTATAGATAACCCTAGCGCCTGGGATCATCCTTTGGACAACTCTTTCTGCCAAATC
TAGGTCCAAAATCACTTCATTGATACCATTATTGTACAACTTGAGCAAGTTGTCGATCAGCTCCTCAAATT
GGTCCTCTGTAACGGATGACTCAACTTGCACATTAACTTGAAGCTCAGTCGATTGAGTGAACTTGATCAGG
TTGTGCAGCTGGTCAGCAGCATAGGGAAACACGGCTTTTCCTACCAAACTCAAGGAATTATCAAACTCTGC
AACACTTGCGTATGCAGGTAGCAAGGGAAATGTCATACTTGAAGTCGGACAGTGAGTGTAGTCTTGAGAAA
TTCTGAAGCCGTATTTTTATTATCAGTGAGTCAGTCATCAGGAGATCCTCTACGCCGGACGCATCGTGGCC
GGCATCACCGGCGCCACAGGTGCGGTTGCTGGCGCCTATATCGCCGACATCACCGATGGGAAGATCGGG
CTCGCCACTTCGGGCTCATGAGCGCTTGTTTCGGCGTGGGTATGGTGGCAGGCCCCGTGGCCGGGGGACT
GTTGGGCGCCATCTCCTTGCATGCACCATTCCTTGCGGCGGCGGTGCTCAACGGCCTCAACCTACTACTG
GGCTGCTTCCTAATGCAGGAGTCGCATAAGGGAGAGCGTCGAGTATCTATGATTGGAAGTATGGGAATGG
TGATACCCGCATTCTTCAGTGTCTTGAGGTCTCCTATCAGATTATGCCCAACTAAAGCAACCGGAGGAGG
AGATTTCATGGTAAATTTCTCTGACTTTTGGTCATCAGTAGACTCGAACTGTGAGACTATCTCGGTTATG
ACAGCAGAAATGTCCTTCTTGGAGACAGTAAATGAAGTCCCACCAATAAAGAAATCCTTGTTATCAGGAA
CAAACTTCTTGTTTCGAACTTTTTCGGTGCCTTGAACTATAAAATGTAGAGTGGATATGTCGGGTAGGAA
TGGAGCGGGCAAATGCTTACCTTCTGGACCTTCAAGAGGTATGTAGGGTTTGTAGATACTGATGCCAACT
TCAGTGACAACGTTGCTATTTCGTTCAAACCATTCCGAATCCAGAGAAATCAAAGTTGTTTGTCTACTAT
TGATCCAAGCCAGTGCGGTCTTGAAACTGACAATAGTGTGCTCGTGTTTTGAGGTCATCTTTGTATGAAT
AAATCTAGTCTTTGATCTAAATAATCTTGACGAGCCAAGGCGATAAATACCCAAATCTAAAACTCTTTTA
AAACGTTAAAAGGACAAGTATGTCTGCCTGTATTAAACCCCAAATCAGCTCGTAGTCTGATCCTCATCAA
CTTGAGGGGCACTATCTTGTTTTAGAGAAATTTGCGGAGATGCGATATCGAGAAAAGGTACGCTGATTT
TAAACGTGAAATTTATCTCAAGATCTCTGCCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCCGTCAGGGCGC
GTCAGCGGGTGTTGGCGGGTGTCGGGGCGCAGCCATGACCCAGTCACGTAGCGATAGCGGAGTGTATACT
GGCTTAACTATGCGGCATCAGAGCAGATTGTACTGAGAGTGCACCATATGCGGTGTGAAATACCGCACAG
ATGCGTAAGGAGAAAATACCGCATCAGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCAATGCTCACGCTG
TAGGTATCTCAGTTCGGTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGTCTGACGCTCA
GTGGAACGAAAACTCACGTTAAGGGATTTTGGTCATGAGATTATCAAAAAGGATCTTCACCTAGATCCTT
TTAAATTAAAAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCA
CGCTCACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAGTTAA
TAGTTTGCGCAACGTTGTTGCCATTGCTGCAGGCATCGTGGTGTCACGCTCGTCGTTTGGTATGGCTTCA
TTCAGCTCCGGTTCCCAACGATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCACTCATGGTTATGGCAGCACT
GCATAATTCTCTTACTGTCATGCCATCCGTAAGATGCTTTTCTGTGACTGGTGAGTACTCAACCAAGTCA
```

FIGURE 5, cont.

```
TTCTGAGAATAGTGTATGCGGCGACCGAGTTGCTCTTGCCCGGCGTCAACACGGGATAATACCGCGCCAC
ATAGCAGAACTTTAAAAGTGCTCATCATTGGAAAACGTTCTTCGGGGCGAAAACTCTCAAGGATCTTACC
GCTGTTGAGATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAAGGGAATAAGGGCGACACGGAAAT
GTTGAATACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAAAGTGCCA
CCTGACGTCTAAGAAACCATTATTATCATGACATTAACCTATAAAAATAGGCGTATCACGAGGCCCTTTC
GTCTTCAAGAATTAATTCTCATGTTTGACAGCTTATCATCGATAAGCTGACTCATGTTGGTATTGTGAAA
TAGACGCAGATCGGGAACACTGAAAAATAACAGTTATTATTCG
```

FIGURE 6

Sequence of pPICGIco-hITF$_{15-73}$ (SEQ ID NO: 3)

AGATCTAACATCCAAAGACGAAAGGTTGAATGAAACCTTTTTGCCATCCGACATCCACAGGTCCATTCTC
ACACATAAGTGCCAAACGCAACAGGAGGGGATACACTAGCAGCAGACCGTTGCAAACGCAGGACCTCCAC
TCCTCTTCTCCTCAACACCCACTTTTGCCATCGAAAAACCAGCCCAGTTATTGGGCTTGATTGGAGCTCG
CTCATTCCAATTCCTTCTATTAGGCTACTAACACCATGACTTTATTAGCCTGTCTATCCTGGCCCCCCTG
GCGAGGTTCATGTTTGTTTATTTCCGAATGCAACAAGCTCCGCATTACACCCGAACATCACTCCAGATGA
GGGCTTTCTGAGTGTGGGGTCAAATAGTTTCATGTTCCCCAAATGGCCCAAAACTGACAGTTTAAACGCT
GTCTTGGAACCTAATATGACAAAAGCGTGATCTCATCCAAGATGAACTAAGTTTGGTTCGTTGAAATGCT
AACGGCCAGTTGGTCAAAAAGAAACTTCCAAAAGTCGCCATACCGTTTGTCTTGTTTGGTATTGATTGAC
GAATGCTCAAAAATAATCTCATTAATGCTTAGCGCAGTCTCTCTATCGCTTCTGAACCCCGGTGCACCTG
TGCCGAAACGCAAATGGGGAAACACCCGCTTTTTGGATGATTATGCATTGTCTCCACATTGTATGCTTCC
AAGATTCTGGTGGGAATACTGCTGATAGCCTAACGTTCATGATCAAAATTTAACTGTTCTAACCCCTACT
TGACAGCAATATATAAACAGAAGGAAGCTGCCCTGTCTTAAACCTTTTTTTTTATCATCATTATTAGCTT
ACTTTCATAATTGCGACTGGTTCCAATTGACAAGCTTTTGATTTTAACGACTTTTAACGACAACTTGAGA
AGATCAAAAAACAACTAATTATTCGAAGGATCCAAACGATGAGATTTCCTTCAATTTTTACTGCAGTTTT
ATTCGCAGCATCCTCCGCATTAGCTGCTCCAGTCAACACTACAACAGAAGATGAAACGGCACAAATTCCG
GCTGAAGCTGTCATCGGTTACTCAGATTTAGAAGGGGATTTCGATGTTGCTGTTTTGCCATTTTCCAACA
GCACAAATAACGGGTTATTGTTTATAAATACTACTATTGCCAGCATTGCTGCTAAAGAAGAAGGGGTATC
TCTCGAGAAAAGAGAGGAGTACGTGGGCCTGTCTGCAAACCAGTGTGCCGTGCCAGCCAAGGACAGGGTGG
ACTGCGGCTACCCCATGTCACCCCAAGGAGTGCAACAACCGGGGCTGCTGCTTTGACTCCAGGATCCCT
GGAGTGCCTTGGTGTTTCAAGCCCTGCAGGAAGCAGAATGCACCTTCTGAGAATTCCCTAGGGCGGCCGC
GAATTAATTCGCCTTAGACATGACTGTTCCTCAGTTCAAGTTGGGCACTTACGAGAAGACCGGTCTTGCTA
GATTCTAATCAAGAGGATGTCAGAATGCCATTTGCCTGAGAGATGCAGGCTTCATTTTGATACTTTTTA
TTTGTAACCTATATAGTATAGGATTTTTTTTGTCATTTTGTTTCTTCTCGTACGAGCTTGCTCCTGATCAG
CCTATCTCGCAGCTGATGAATATCTTGTGGTAGGGGTTTGGGAAAATCATTCGAGTTTGATGTTTTTCTTG
GTATTTCCCACTCCTCTTCAGAGTACAGAAGATTAAGTGAGAAGTTCGTTTGTGCAAGCTTATCGATAAGC
TTTAATGCGGTAGTTTATCACAGTTAAATTGCTAACGCAGTCAGGCACCGTGTATGAAATCTAACAATGCG
CTCATCGTCATCCTCGGCACCGTCACCCTGGATGCTGTAGGCATAGGCTTGGTTATGCCGGTACTGCCGGG
CCTCTTGCGGGATATCGTCCATTCCGACAGCATCGCCAGTCACTATGGCGTGCTGCTAGCGCTATATGCGT
TGATGCAATTTCTATGCGCACCCGTTCTCGGAGCACTGTCCGACCGCTTTGGCCGCCGCCCAGTCCTGCTC
GCTTCGCTACTTGGAGCCACTATCGACTACGCGATCATGGCGACCACACCCGTCCTGTGGATCTATCGAAT
CTAAATGTAAGTTAAAATCTCTAAATAATTAAATAAGTCCCAGTTTCTCCATACGAACCTTAACAGCATTG
CGGTGAGCATCTAGACCTTAACAGCAGCCAGATCCATCACTGCTTGGCCAATATGTTTCAGTCCCTCAGG
AGTTACGTCTTGTGAAGTGATGAACTTCTGGAAGGTTGCAGTGTTAACTCCGCTGTATTGACGGGCATATC
CGTACGTTGGCAAAGTGTGGTTGGTACCGGAGGAGTAATCTCCACAACTCTCTGGAGAGTAGGCACCAACA
AACACAGATCCAGCGTGTTGTACTTGATCAACATAAGAAGAAGCATTCTCGATTTGCAGGATCAAGTGTTC
AGGAGCGTACTGATTGGACATTTCCAAAGCCTGCTCGTAGGTTGCAACCGATAGGGTTGTAGAGTGTGCAA
TACACTTGCGTACAATTTCAACCCTTGGCAACTGCACAGCTTGGTTGTGAACAGCATCTTCAATTCTGGCA
AGCTCCTTGTCTGTCATATCGACAGCCAACAGAATCACCTGGGAATCAATACCATGTTCAGCTTGAGACAG
AAGGTCTGAGGCAACGAAATCTGGATCAGCGTATTTATCAGCAATAACTAGAACTTCAGAAGGCCCAGCAG
GCATGTCAATACTACACAGGGCTGATGTGTCATTTTGAACCATCATCTTGGCAGCAGTAACGAACTGGTTT
CCTGGACCAAATATTTTGTCACACTTAGGAACAGTTTCTGTTCCGTAAGCCATAGCAGCTACTGCCTGGGC
GCCTCCTGCTAGCACGATACACTTAGCACCAACCTTGTGGGCAACGTAGATGACTTCTGGGGTAAGGGTAC
CATCCTTCTTAGGTGGAGATGCAAAAACAATTTCTTTGCAACCAGCAACTTTGGCAGGAACACCCAGCATC
AGGGAAGTGGAAGGCAGAATTGCGGTTCCACCAGGAATATAGAGGCCAACTTTCTCAATAGGTCTTGCAAA
ACGAGAGCAGACTACACCAGGGCAAGTCTCAACTTGCAACGTCTCCGTTAGTTGAGCTTCATGGAATTTCC
TGACGTTATCTATAGAGAGATCAATGGCTCTCTTAACGTTATCTGGCAATTGCATAAGTTCCTCTGGGAAA
GGAGCTTCTAACACAGGTGTCTTCAAAGCGACTCCATCAAACTTGGCAGTTAGTTCTAAAAGGGCTTTGTC
ACCATTTTGACGAACATTGTCGACAATTGGTTTGACTAATTCCATAATCTGTTCCGTTTTCTGGATAGGAC

FIGURE 6, cont.

```
GACGAAGGGCATCTTCAATTTCTTGTGAGGAGGCCTTAGAAACGTCAATTTTGCACAATTCAATACGACCT
TCAGAAGGGACTTCTTTAGGTTTGGATTCTTCTTTAGGTTGTTCCTTGGTGTATCCTGGCTTGGCATCTCC
TTTCCTTCTAGTGACCTTTAGGGACTTCATATCCAGGTTTCTCTCCACCTCGTCCAACGTCACACCGTACT
TGGCACATCTAACTAATGCAAAATAAAATAAGTCAGCACATTCCCAGGCTATATCTTCCTTGGATTTAGCT
TCTGCAAGTTCATCAGCTTCCTCCCTAATTTTAGCGTTCAACAAAACTTCGTCGTCAAATAACCGTTTGGT
ATAAGAACCTTCTGGAGCATTGCTCTTACGATCCCACAAGGTGGCTTCCATGGCTCTAAGACCCTTTGATT
GGCCAAAACAGGAAGTGCGTTCCAAGTGACAGAAACCAACACCTGTTTGTTCAACCACAAATTTCAAGCAG
TCTCCATCACAATCCAATTCGATACCCAGCAACTTTTGAGTTGCTCCAGATGTAGCACCTTTATACCACAA
ACCGTGACGACGAGATTGGTAGACTCCAGTTTGTGTCCTTATAGCCTCCGGAATAGACTTTTTGGACGAGT
ACACCAGGCCCAACGAGTAATTAGAAGAGTCAGCCACCAAAGTAGTGAATAGACCATCGGGGCGGTCAGTA
GTCAAAGACGCCAACAAAATTTCACTGACAGGGAACTTTTTGACATCTTCAGAAAGTTCGTATTCAGTAGT
CAATTGCCGAGCATCAATAATGGGGATTATACCAGAAGCAACAGTGGAAGTCACATCTACCAACTTTGCGG
TCTCAGAAAAAGCATAAACAGTTCTACTACCGCCATTAGTGAAACTTTTCAAATCGCCCAGTGGAGAAGAA
AAAGGCACAGCGATACTAGCATTAGCGGGCAAGGATGCAACTTTATCAACCAGGGTCCTATAGATAACCCT
AGCGCCTGGGATCATCCTTTGGACAACTCTTTCTGCCAAATCTAGGTCCAAAATCACTTCATTGATACCAT
TATTGTACAACTTGAGCAAGTTGTCGATCAGCTCCTCAAATTGGTCCTCTGTAACGGATGACTCAACTTGC
ACATTAACTTGAAGCTCAGTCGATTGAGTGAACTTGATCAGGTTGTGCAGCTGGTCAGCAGCATAGGGAAA
CACGGCTTTTCCTACCAAACTCAAGGAATTATCAAACTCTGCAACACTTGCGTATGCAGGTAGCAAGGGAA
ATGTCATACTTGAAGTCGGACAGTGAGTGTAGTCTTGAGAAATTCTGAAGCCGTATTTTATTATCAGTGA
GTCAGTCATCAGGAGATCCTCTACGCCGGACGCATCGTGGCCGGCATCACCGGCGCCACAGGTGCGGTTGC
TGGCGCCTATATCGCCGACATCACCGATGGGGAAGATCGGGCTCGCCACTTCGGGCTCATGAGCGCTTGTT
TCGGCGTGGGTATGGTGGCAGGCCCCGTGGCCGGGGACTGTTGGGCGCCATCTCCTTGCATGCACCATTC
CTTGCGGCGGCGGTGCTCAACGGCCTCAACCTACTACTGGGCTGCTTCCTAATGCAGGAGTCGCATAAGGG
AGAGCGTCGAGTATCTATGATTGGAAGTATGGGAATGGTGATACCCGCATTCTTCAGTGTCTTGAGGTCTC
CTATCAGATTATGCCCAACTAAAGCAACCGGAGGAGGAGATTTCATGGTAAATTTCTCTGACTTTTGGTCA
TCAGTAGACTCGAACTGTGAGACTATCTCGGTTATGACAGCAGAAATGTCCTTCTTGGAGACAGTAAATGA
AGTCCCACCAATAAAGAAATCCTTGTTATCAGGAACAAACTTCTTGTTTCGAACTTTTTCGGTGCCTTGAA
CTATAAAATGTAGAGTGGATATGTCGGGTAGGAATGGAGCGGGCAAATGCTTACCTTCTGGACCTTCAAGA
GGTATGTAGGGTTTGTAGATACTGATGCCAACTTCAGTGACAACGTTGCTATTTCGTTCAAACCATTCCGA
ATCCAGAGAAATCAAAGTTGTTTGTCTACTATTGATCCAAGCCAGTGCGGTCTTGAAACTGACAATAGTGT
GCTCGTGTTTTGAGGTCATCTTTGTATGAATAAATCTAGTCTTTGATCTAAATAATCTTGACGAGCCAAGG
CGATAAATACCCAAATCTAAAACTCTTTTAAAACGTTAAAAGGACAAGTATGTCTGCCTGTATTAAACCCC
AAATCAGCTCGTAGTCTGATCCTCATCAACTTGAGGGGCACTATCTTGTTTTAGAGAAATTTGCGGAGATG
CGATATCGAGAAAAAGGTACGCTGATTTTAAACGTGAAATTTATCTCAAGATCTCTGCCTCGCGCGTTTCG
GTGATGACGGTGAAAACCTCTGACACATGCAGCTCCCGGAGACGGTCACAGCTTGTCTGTAAGCGGATGCC
GGGAGCAGACAAGCCCGTCAGGGCGCGTCAGCGGGTGTTGGCGGGTGTCGGGCGCAGCCATGACCCAGTC
ACGTAGCGATAGCGGAGTGTATACTGGCTTAACTATGCGGCATCAGAGCAGATTGTACTGAGAGTGCACCA
TATGCGGTGTGAAATACCGCACAGATGCGTAAGGAGAAAATACCGCATCAGGCGCTCTTCCGCTTCCTCGC
TCACTGACTCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCACAAAAATCGACGCT
CAAGTCAGAGGTGGCGAAACCCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCCCTTCGGGAAGCGTGGCGCT
TTCTCAATGCTCACGCTGTAGGTATCTCAGTTCGGTGTAGGTCGTTCGCTCCAAGCTGGGCTGTGTGCACG
AACCCCCCGTTCAGCCCGACCGCTGCGCCTTATCCGGTAACTATCGTCTTGAGTCCAACCCGGTAAGACAC
GACTTATCGCCACTGGCAGCAGCCACTGGTAACAGGATTAGCAGAGCGAGGTATGTAGGCGGTGCTACAGA
GTTCTTGAAGTGGTGGCCTAACTACGGCTACACTAGAAGGACAGTATTTGGTATCTGCGCTCTGCTGAAGC
CAGTTACCTTCGGAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCTTTTCTACGGG
GTCTGACGCTCAGTGGAACGAAAACTCACGTTAAGGGATTTTGGTCATGAGATTATCAAAAAGGATCTTCA
CCTAGATCCTTTTAAATTAAAAATGAAGTTTTAAATCAATCTAAAGTATATATGAGTAAACTTGGTCTGAC
AGTTACCAATGCTTAATCAGTGAGGCACCTATCTCAGCGATCTGTCTATTTCGTTCATCCATAGTTGCCTG
ACTCCCCGTCGTGTAGATAACTACGATACGGGAGGGCTTACCATCTGGCCCCAGTGCTGCAATGATACCGC
GAGACCCACGCTCACCGGCTCCAGATTTATCAGCAATAAACCAGCCAGCCGGAAGGGCCGAGCGCAGAAGT
GGTCCTGCAACTTTATCCGCCTCCATCCAGTCTATTAATTGTTGCCGGGAAGCTAGAGTAAGTAGTTCGCC
AGTTAATAGTTTGCGCAACGTTGTTGCCATTGCTGCAGGCATCGTGGTGTCACGCTCGTCGTTTGGTATGG
CTTCATTCAGCTCCGGTTCCCAACGATCAAGGCGAGTTACATGATCCCCCATGTTGTGCAAAAAAGCGGTT
```

FIGURE 6, cont.

```
AGCTCCTTCGGTCCTCCGATCGTTGTCAGAAGTAAGTTGGCCGCAGTGTTATCACTCATGGTTATGGCAGC
ACTGCATAATTCTCTTACTGTCATGCCATCCGTAAGATGCTTTTCTGTGACTGGTGAGTACTCAACCAAGT
CATTCTGAGAATAGTGTATGCGGCGACCGAGTTGCTCTTGCCCGGCGTCAACACGGGATAATACCGCGCCA
CATAGCAGAACTTTAAAAGTGCTCATCATTGGAAAACGTTCTTCGGGGCGAAAACTCTCAAGGATCTTACC
GCTGTTGAGATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAAGGGAATAAGGGCGACACGGAAAT
GTTAATACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAAAGTGCCA
CCTGACGTCTAAGAAACCATTATTATCATGACATTAACCTATAAAAATAGGCGTATCACGAGGCCCTTTC
GTCTTCAAGAATTAATTCTCATGTTTGACAGCTTATCATCGATAAGCTGACTCATGTTGGTATTGTGAAA
TAGACGCAGATCGGGAACACTGAAAAATAACAGTTATTATTCG
```

FIGURE 7

Sequence of pPICGIco-hITF$_{1-73}$ (SEQ ID NO: 4)

AGATCTAACATCCAAAGACGAAAGGTTGAATGAAACCTTTTTGCCATCCGACATCCACAGGTCCATTCTC
ACACATAAGTGCCAAACGCAACAGGAGGGGATACACTAGCAGCAGACCGTTGCAAACGCAGGACCTCCAC
TCCTCTTCTCCTCAACACCCACTTTTGCCATCGAAAAACCAGCCCAGTTATTGGGCTTGATTGGAGCTCG
CTCATTCCAATTCCTTCTATTAGGCTACTAACACCATGACTTTATTAGCCTGTCTATCCTGGCCCCCTG
GCGAGGTTCATGTTTGTTTATTTCCGAATGCAACAAGCTCCGCATTACACCCGAACATCACTCCAGATGA
GGGCTTTCTGAGTGTGGGGTCAAATAGTTTCATGTTCCCCAAATGGCCCAAAACTGACAGTTTAAACGCT
GTCTTGGAACCTAATATGACAAAAGCGTGATCTCATCCAAGATGAACTAAGTTTGGTTCGTTGAAATGCT
AACGGCCAGTTGGTCAAAAAGAAACTTCCAAAAGTCGCCATACCGTTTGTCTTGTTTGGTATTGATTGAC
GAATGCTCAAAAATAATCTCATTAATGCTTAGCGCAGTCTCTCTATCGCTTCTGAACCCCGGTGCACCTG
TGCCGAAACGCAAATGGGGAAACACCCGCTTTTTGGATGATTATGCATTGTCTCCACATTGTATGCTTCC
AAGATTCTGGTGGGAATACTGCTGATAGCCTAACGTTCATGATCAAAATTTAACTGTTCTAACCCCTACT
TGACAGCAATATATAAACAGAAGGAAGCTGCCCTGTCTTAAACCTTTTTTTTATCATCATTATTAGCTT
ACTTTCATAATTGCGACTGGTTCCAATTGACAAGCTTTTGATTTTAACGACTTTTAACGACAACTTGAGA
AGATCAAAAAACAACTAATTATTCGAAGGATCCAAACGATGAGATTTCCTTCAATTTTTACTGCAGTTTT
ATTCGCAGCATCCTCCGCATTAGCTGCTCCAGTCAACACTACAACAGAAGATGAAACGGCACAAATTCCG
GCTGAAGCTGTCATCGGTTACTCAGATTTAGAAGGGGATTTCGATGTTGCTGTTTTGCCATTTTCCAACA
GCACAAATAACGGGTTATTGTTTATAAATACTACTATTGCCAGCATTGCTGCTAAAGAAGAAGGGGTATC
TCTCGAGAAAAGAATGCTGGGGCTGGTCCTGGCCTTGCTGTCCTCCAGCTCTGCTGAGGAGTACGTGGGCC
TGTCTGCAAACCAGTGTGCCGTGCCAGCCAAGGACAGGGTGGACTGCGGCTACCCCCATGTCACCCCAAG
GAGTGCAACAACCGGGGCTGCTGCTTTGACTCCAGGATCCCTGGAGTGCCTTGGTGTTTCAAGCCCCTGCA
GGAAGCAGAATGCACCTTCTGAGAATTCCCTAGGGCGGCCGCGAATTAATTCGCCTTAGACATGACTGTTC
CTCAGTTCAAGTTGGGCACTTACGAGAAGACCGGTCTTGCTAGATTCTAATCAAGAGGATGTCAGAATGCC
ATTTGCCTGAGAGATGCAGGCTTCATTTTTGATACTTTTTTATTTGTAACCTATATAGTATAGGATTTTTT
TTGTCATTTTGTTTCTTCTCGTACGAGCTTGCTCCTGATCAGCCTATCTCGCAGCTGATGAATATCTTGTG
GTAGGGGTTTGGGAAAATCATTCGAGTTTGATGTTTTTCTTGGTATTTCCCACTCCTCTTCAGAGTACAGA
AGATTAAGTGAGAAGTTCGTTTGTGCAAGCTTATCGATAAGCTTTAATGCGGTAGTTTATCACAGTTAAAT
TGCTAACGCAGTCAGGCACCGTGTATGAAATCTAACAATGCGCTCATCGTCATCCTCGGCACCGTCACCCT
GGATGCTGTAGGCATAGGCTTGGTTATGCCGGTACTGCCGGGCCTCTTGCGGGATATCGTCCATTCCGACA
GCATCGCCAGTCACTATGGCGTGCTGCTAGCGCTATATGCGTTGATGCAATTTCTATGCGCACCCGTTCTC
GGAGCACTGTCCGACCGCTTTGGCCGCCGCCCAGTCCTGCTCGCTTCGCTACTTGGAGCCACTATCGACTA
CGCGATCATGGCGACCACACCCGTCCTGTGGATCTATCGAATCTAAATGTAAGTTAAAATCTCTAAATAAT
TAAATAAGTCCCAGTTTCTCCATACGAACCTTAACAGCATTGCGGTGAGCATCTAGACCTTCAACAGCAGC
CAGATCCATCACTGCTTGGCCAATATGTTTCAGTCCCTCAGGAGTTACGTCTTGTGAAGTGATGAACTTCT
GGAAGGTTGCAGTGTTAACTCCGCTGTATTGACGGGCATATCCGTACGTTGGCAAAGTGTGGTTGGTACCG
GAGGAGTAATCTCCACAACTCTCTGGAGAGTAGGCACCAACAAACACAGATCCAGCGTGTTGTACTTGATC
AACATAAGAAGAAGCATTCTCGATTTGCAGGATCAAGTGTTCAGGAGCGTACTGATTGGACATTTCCAAAG
CCTGCTCGTAGGTTGCAACCGATAGGGTTGTAGAGTGTGCAATACACTTGCGTACAATTTCAACCCTTGGC
AACTGCACAGCTTGGTTGTGAACAGCATCTTCAATTCTGGCAAGCTCCTTGTCTGTCATATCGACAGCCAA
CAGAATCACCTGGGAATCAATACCATGTTCAGCTTGAGACAGAAGGTCTGAGGCAACGAAATCTGGATCAG
CGTATTTATCAGCAATAACTAGAACTTCAGAAGGCCCAGCAGGCATGTCAATACTACACAGGGCTGATGTG
TCATTTTGAACCATCATCTTGGCAGCAGTAACGAACTGGTTTCCTGGACCAAATATTTTGTCACACTTAGG
AACAGTTTCTGTTCCGTAAGCCATAGCAGCTACTGCCTGGGCGCCTCCTGCTAGCACGATACACTTAGCAC
CAACCTTGTGGGCAACGTAGATGACTTCTGGGGTAAGGGTACCATCCTTCTTAGGTGGAGATGCAAAAACA
ATTTCTTTGCAACCAGCAACTTTGGCAGGAACACCCAGCATCAGGGAAGTGGAAGGCAGAATTGCGGTTCC
ACCAGGAATATAGAGGCCAACTTTCTCAATAGGTCTTGCAAAACGAGAGCAGACTACACCAGGGCAAGTCT
CAACTTGCAACGTCTCCGTTAGTTGAGCTTCATGGAATTTCCTGACGTTATCTATAGAGAGATCAATGGCT

FIGURE 7, cont.

```
CTCTTAACGTTATCTGGCAATTGCATAAGTTCCTCTGGGAAAGGAGCTTCTAACACAGGTGTCTTCAAAGC
GACTCCATCAAACTTGGCAGTTAGTTCTAAAAGGGCTTTGTCACCATTTTGACGAACATTGTCGACAATTG
GTTTGACTAATTCCATAATCTGTTCCGTTTTCTGGATAGGACGACGAAGGGCATCTTCAATTTCTTGTGAG
GAGGCCTTAGAAACGTCAATTTTGCACAATTCAATACGACCTTCAGAAGGGACTTCTTTAGGTTTGGATTC
TTCTTTAGGTTGTTCCTTGGTGTATCCTGGCTTGGCATCTCCTTTCCTTCTAGTGACCTTTAGGGACTTCA
TATCCAGGTTTCTCTCCACCTCGTCCAACGTCACACCGTACTTGGCACATCTAACTAATGCAAAATAAAAT
AAGTCAGCACATTCCCAGGCTATATCTTCCTTGGATTTAGCTTCTGCAAGTTCATCAGCTTCCTCCCTAAT
TTTAGCGTTCAACAAAACTTCGTCGTCAAATAACCGTTTGGTATAAGAACCTTCTGGAGCATTGCTCTTAC
GATCCCACAAGGTGGCTTCCATGGCTCTAAGACCCTTTGATTGGCCAAAACAGGAAGTGCGTTCCAAGTGA
CAGAAACCAACACCTGTTTGTTCAACCACAAATTTCAAGCAGTCTCCATCACAATCCAATTCGATACCCAG
CAACTTTTGAGTTGCTCCAGATGTAGCACCTTTATACCACAAACCGTGACGACGAGATTGGTAGACTCCAG
TTTGTGTCCTTATAGCCTCCGGAATAGACTTTTTGGACGAGTACACCAGGCCCAACGAGTAATTAGAAGAG
TCAGCCACCAAAGTAGTGAATAGACCATCGGGGCGGTCAGTAGTCAAAGACGCCAACAAAATTTCACTGAC
AGGGAACTTTTTGACATCTTCAGAAAGTTCGTATTCAGTAGTCAATTGCCGAGCATCAATAATGGGGATTA
TACCAGAAGCAACAGTGGAAGTCACATCTACCAACTTTGCGGTCTCAGAAAAAGCATAAACAGTTCTACTA
CCGCCATTAGTGAAACTTTTCAAATCGCCCAGTGGAGAAGAAAAAGGCACAGCGATACTAGCATTAGCGGG
CAAGGATGCAACTTTATCAACCAGGGTCCTATAGATAACCCTAGCGCCTGGGATCATCCTTTGGACAACTC
TTTCTGCCAAATCTAGGTCCAAAATCACTTCATTGATACCATTATTGTACAACTTGAGCAAGTTGTCGATC
AGCTCCTCAAATTGGTCCTCTGTAACGGATGACTCAACTTGCACATTAACTTGAAGCTCAGTCGATTGAGT
GAACTTGATCAGGTTGTGCAGCTGGTCAGCAGCATAGGGAAACACGGCTTTTCCTACCAAACTCAAGGAAT
TATCAAACTCTGCAACACTTGCGTATGCAGGTAGCAAGGGAAATGTCATACTTGAAGTCGGACAGTGAGTG
TAGTCTTGAGAAATTCTGAAGCCGTATTTTTATTATCAGTGAGTCAGTCATCAGGAGATCCTCTACGCCGG
ACGCATCGTGGCC
GGCATCACCGGCGCCACAGGTGCGGTTGCTGGCGCCTATATCGCCGACATCACCGATGGGGAAGATCGGG
CTCGCCACTTCGGGCTCATGAGCGCTTGTTTCGGCGTGGGTATGGTGGCAGGCCCCGTGGCCGGGGACT
GTTGGGCGCCATCTCCTTGCATGCACCATTCCTTGCGGCGGCGGTGCTCAACGGCCTCAACCTACTACTG
GGCTGCTTCCTAATGCAGGAGTCGCATAAGGGAGAGCGTCGAGTATCTATGATTGGAAGTATGGGAATGG
TGATACCCGCATTCTTCAGTGTCTTGAGGTCTCCTATCAGATTATGCCCAACTAAAGCAACCGGAGGAGG
AGATTTCATGGTAAATTTCTCTGACTTTTGGTCATCAGTAGACTCGAACTGTGAGACTATCTCGGTTATG
ACAGCAGAAATGTCCTTCTTGGAGACAGTAAATGAAGTCCCACCAATAAAGAAATCCTTGTTATCAGGAA
CAAACTTCTTGTTTCGAACTTTTTCGGTGCCTTGAACTATAAAATGTAGAGTGGATATGTCGGGTAGGAA
TGGAGCGGGCAAATGCTTACCTTCTGGACCTTCAAGAGGTATGTAGGGTTTGTAGATACTGATGCCAACT
TCAGTGACAACGTTGCTATTTCGTTCAAACCATTCCGAATCCAGAGAAATCAAAGTTGTTTGTCTACTAT
TGATCCAAGCCAGTGCGGTCTTGAAACTGACAATAGTGTGCTCGTGTTTTGAGGTCATCTTTGTATGAAT
AAATCTAGTCTTTGATCTAAATAATCTTGACGAGCCAAGGCGATAAATACCCAAATCTAAAACTCTTTTA
AAACGTTAAAAGGACAAGTATGTCTGCCTGTATTAAACCCCAAATCAGCTCGTAGTCTGATCCTCATCAA
CTTGAGGGCACTATCTTGTTTTAGAGAAATTTGCGGAGATGCGATATCGAGAAAAAGGTACGCTGATTT
TAAACGTGAAATTTATCTCAAGATCTCTGCCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCCGTCAGGGCGC
GTCAGCGGGTGTTGGCGGGTGTCGGGGCGCAGCCATGACCCAGTCACGTAGCGATAGCGGAGTGTATACT
GGCTTAACTATGCGGCATCAGAGCAGATTGTACTGAGAGTGCACCATATGCGGTGTGAAATACCGCACAG
ATGCGTAAGGAGAAAATACCGCATCAGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCCGCGTTGCTGGC
GTTTTTCCATAGGCTCCGCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCAATGCTCACGCTG
TAGGTATCTCAGTTCGGTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGTCTGACGCTCA
GTGGAACGAAAACTCACGTTAAGGGATTTTGGTCATGAGATTATCAAAAAGGATCTTCACCTAGATCCTT
TTAAATTAAAAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCA
```

FIGURE 7, cont.

```
CGCTCACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAGTTAA
TAGTTTGCGCAACGTTGTTGCCATTGCTGCAGGCATCGTGGTGTCACGCTCGTCGTTTGGTATGGCTTCA
TTCAGCTCCGGTTCCCAACGATCAAGGCGAGTTACATGATCCCCATGTTGTGCAAAAAAGCGGTTAGCT
CCTTCGGTCCTCCGATCGTTGTCAGAAGTAAGTTGGCCGCAGTGTTATCACTCATGGTTATGGCAGCACT
GCATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAACACGGGATAATACCGCGCCAC
ATAGCAGAACTTTAAAAGTGCTCATCATTGGAAAACGTTCTTCGGGGCGAAAACTCTCAAGGATCTTACC
GCTGTTGAGATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAAGGGAATAAGGGCGACACGGAAAT
GTTGAATACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAAAGTGCCA
CCTGACGTCTAAGAAACCATTATTATCATGACATTAACCTATAAAAATAGGCGTATCACGAGGCCCTTTC
GTCTTCAAGAATTAATTCTCATGTTTGACAGCTTATCATCGATAAGCTGACTCATGTTGGTATTGTGAAA
TAGACGCAGATCGGGAACACTGAAAAATAACAGTTATTATTCG
```

FIGURE 8

Sequence of pPICpre (SEQ ID NO: 5)

```
AGATCTAACATCCAAAGACGAAAGGTTGAATGAAACCTTTTTGCCATCCGACATCCACAGGTCCATTCTC
ACACATAAGTGCCAAACGCAACAGGAGGGGATACACTAGCAGCAGACCGTTGCAAACGCAGGACCTCCAC
TCCTCTTCTCCTCAACACCCACTTTTGCCATCGAAAAACCAGCCCAGTTATTGGGCTTGATTGGAGCTCG
CTCATTCCAATTCCTTCTATTAGGCTACTAACACCATGACTTTATTAGCCTGTCTATCCTGGCCCCCCTG
GCGAGGTTCATGTTTGTTTATTTCCGAATGCAACAAGCTCCGCATTACACCCGAACATCACTCCAGATGA
GGGCTTTCTGAGTGTGGGGTCAAATAGTTTCATGTTCCCCAAATGGCCCAAAACTGACAGTTTAAACGCT
GTCTTGGAACCTAATATGACAAAAGCGTGATCTCATCCAAGATGAACTAAGTTTGGTTCGTTGAAATGCT
AACGGCCAGTTGGTCAAAAAGAAACTTCCAAAAGTCGCCATACCGTTTGTCTTGTTTGGTATTGATTGAC
GAATGCTCAAAAATAATCTCATTAATGCTTAGCGCAGTCTCTATCGCTTCTGAACCCCGGTGCACCTG
TGCCGAAACGCAAATGGGGAAACACCCGCTTTTTGGATGATTATGCATTGTCTCCACATTGTATGCTTCC
AAGATTCTGGTGGGAATACTGCTGATAGCCTAACGTTCATGATCAAAATTTAACTGTTCTAACCCCTACT
TGACAGCAATATATAAACAGAAGGAAGCTGCCCTGTCTTAAACCTTTTTTTTATCATCATTATTAGCTT
ACTTTCATAATTGCGACTGGTTCCAATTGACAAGCTTTTGATTTAACGACTTTTAACGACAACTTGAGA
AGATCAAAAAACAACTAATTATTCGAAGGATCCAAACGATGAGATTTCCTTCAATTTTTACTGCAGTTTT
ATTCGCAGCATCCTCCGCATTAGCTGCTCTCGAGTAGAATTCCCTAGGCGGCCGCGAATTAATTCGCCTT
AGACATGACTGTTCCTCAGTTCAAGTTGGGCACTTACGAGAAGACCGGTCTTGCTAGATTCTAATCAAGAG
GATGTCAGAATGCCATTTGCCTGAGAGATGCAGGCTTCATTTTTGATACTTTTTTATTTGTAACCTATATA
GTATAGGATTTTTTTTGTCATTTTGTTTCTTCTCGTACGAGCTTGCTCCTGATCAGCCTATCTCGCAGCTG
ATGAATATCTTGTGGTAGGGGTTTGGGAAAATCATTCGAGTTTGATGTTTTTCTTGGTATTTCCCACTCCT
CTTCAGAGTACAGAAGATTAAGTGAGAAGTTCGTTTGTGCAAGCTTATCGATAAGCTTTAATGCGGTAGTT
TATCACAGTTAAATTGCTAACGCAGTCAGGCACCGTGTATGAAATCTAACAATGCGCTCATCGTCATCCTC
GGCACCGTCACCCTGGATGCTGTAGGCATAGGCTTGGTTATGCCGGTACTGCCGGGCCTCTTGCGGGATAT
CGTCCATTCCGACAGCATCGCCAGTCACTATGGCGTGCTGCTAGCGCTATATGCGTTGATGCAATTTCTAT
GCGCACCCGTTCTCGGAGCACTGTCCGACCGCTTTGGCCGCCGCCCAGTCCTGCTCGCTTCGCTACTTGGA
GCCACTATCGACTACGCGATCATGGCGACCACACCCGTCCTGTGGATCTATCGAATCTAAATGTAAGTTAA
AATCTCTAAATAATTAAATAAGTCCCAGTTTCTCCATACGAACCTTAACAGCATTGCGGTGAGCATCTAGA
CCTTCAACAGCAGCCAGATCCATCACTGCTTGGCCAATATGTTTCAGTCCCTCAGGAGTTACGTCTTGTGA
AGTGATGAACTTCTGGAAGGTTGCAGTGTTAACTCCGCTGTATTGACGGGCATATCCGTACGTTGGCAAAG
TGTGGTTGGTACCGGAGGAGTAATCTCCACAACTCTCTGGAGAGTAGGCACCAACAAACACAGATCCAGCG
TGTTGTACTTGATCAACATAAGAAGAAGCATTCTCGATTTGCAGGATCAAGTGTTCAGGAGCGTACTGATT
GGACATTTCCAAAGCCTGCTCGTAGGTTGCAACCGATAGGGTTGTAGAGTGTGCAATACACTTGCGTACAA
TTTCAACCCTTGGCAACTGCACAGCTTGGTTGTGAACAGCATCTTCAATTCTGGCAAGCTCCTTGTCTGTC
ATATCGACAGCCAACAGAATCACCTGGGAATCAATACCATGTTCAGCTTGAGACAGAAGGTCTGAGGCAAC
GAAATCTGGATCAGCGTATTTATCAGCAATAACTAGAACTTCAGAAGGCCCAGCAGGCATGTCAATACTAC
ACAGGGCTGATGTGTCATTTTGAACCATCATCTTGGCAGCAGTAACGAACTGGTTTCCTGGACCAAATATT
TTGTCACACTTAGGAACAGTTTCTGTTCCGTAAGCCATAGCAGCTACTGCCTGGGCGCCTCCTGCTAGCAC
GATACACTTAGCACCAACCTTGTGGGCAACGTAGATGACTTCTGGGGTAAGGGTACCATCCTTCTTAGGTG
GAGATGCAAAAACAATTTCTTTGCAACCAGCAACTTTGGCAGGAACACCCAGCATCAGGGAAGTGGAAGGC
AGAATTGCGGTTCCACCAGGAATATAGAGGCCAACTTTCTCAATAGGTCTTGCAAAACGAGAGCAGACTAC
ACCAGGGCAAGTCTCAACTTGCAACGTCTCCGTTAGTTGAGCTTCATGGAATTCCTGACGTTATCTATAG
AGAGATCAATGGCTCTCTTAACGTTATCTGGCAATTGCATAAGTTCCTCTGGGAAAGGAGCTTCTAACACA
GGTGTCTTCAAAGCGACTCCATCAAACTTGGCAGTTAGTTCTAAAAGGGCTTTGTCACCATTTTGACGAAC
ATTGTCGACAATTGGTTTGACTAATTCCATAATCTGTTCCGTTTTCTGGATAGGACGACGAAGGGCATCTT
CAATTCTTGTGAGGAGGCCTTAGAAACGTCAATTTGCACAATTCAATACGACCTTCAGAAGGGACTTCT
TTAGGTTTGGATTCTTCTTTAGGTTGTTCCTTGGTGTATCCTGGCTTGGCATCTCCTTTCCTTCAGTGAC
CTTTAGGGACTTCATATCCAGGTTTCTCTCCACCTCGTCCAACGTCACACCGTACTTGGCACATCTAACTA
ATGCAAAATAAAATAAGTCAGCACATTCCCAGGCTATATCTTCCTTGGATTTAGCTTCTGCAAGTTCATCA
GCTTCCTCCCTAATTTTAGCGTTCAACAAACTTCGTCGTCAAATAACCGTTTGGTATAAGAACCTTCTGG
```

FIGURE 8, cont.

```
AGCATTGCTCTTACGATCCCACAAGGTGGCTTCCATGGCTCTAAGACCCTTTGATTGGCCAAAACAGGAAG
TGCGTTCCAAGTGACAGAAACCAACACCTGTTTGTTCAACCACAAATTTCAAGCAGTCTCCATCACAATCC
AATTCGATACCCAGCAACTTTTGAGTTGCTCCAGATGTAGCACCTTTATACCACAAACCGTGACGACGAGA
TTGGTAGACTCCAGTTTGTGTCCTTATAGCCTCCGGAATAGACTTTTTGGACGAGTACACCAGGCCCAACG
AGTAATTAGAAGAGTCAGCCACCAAAGTAGTGAATAGACCATCGGGGCGGTCAGTAGTCAAAGACGCCAAC
AAAATTTCACTGACAGGGAACTTTTTGACATCTTCAGAAAGTTCGTATTCAGTAGTCAATTGCCGAGCATC
AATAATGGGGATTATACCAGAAGCAACAGTGGAAGTCACATCTACCAACTTTGCGGTCTCAGAAAAAGCAT
AAACAGTTCTACTACCGCCATTAGTGAAACTTTTCAAATCGCCCAGTGGAGAAGAAAAAGGCACAGCGATA
CTAGCATTAGCGGGCAAGGATGCAACTTTATCAACCAGGGTCCTATAGATAACCCTAGCGCCTGGGATCAT
CCTTTGGACAACTCTTTCTGCCAAATCTAGGTCCAAAATCACTTCATTGATACCATTATTGTACAACTTGA
GCAAGTTGTCGATCAGCTCCTCAAATTGGTCCTCTGTAACGGATGACTCAACTTGCACATTAACTTGAAGC
TCAGTCGATTGAGTGAACTTGATCAGGTTGTGCAGCTGGTCAGCAGCATAGGGAAACACGGCTTTTCCTAC
CAAACTCAAGGAATTATCAAACTCTGCAACACTTGCGTATGCAGGTAGCAAGGGAAATGTCATACTTGAAG
TCGGACAGTGAGTGTAGTCTTGAGAAATTCTGAAGCCGTATTTTATTATCAGTGAGTCAGTCATCAGGAG
ATCCTCTACGCCGGACGCATCGTGGCC
GGCATCACCGGCGCCACAGGTGCGGTTGCTGGCGCCTATATCGCCGACATCACCGATGGGAAGATCGGG
CTCGCCACTTCGGGCTCATGAGCGCTTGTTTCGGCGTGGGTATGGTGGCAGGCCCCGTGGCCGGGGGACT
GTTGGGCGCCATCTCCTTGCATGCACCATTCCTTGCGGCGGCGGTGCTCAACGGCCTCAACCTACTACTG
GGCTGCTTCCTAATGCAGGAGTCGCATAAGGGAGAGCGTCGAGTATCTATGATTGGAAGTATGGGAATGG
TGATACCCGCATTCTTCAGTGTCTTGAGGTCTCCTATCAGATTATGCCCAACTAAAGCAACCGGAGGAGG
AGATTTCATGGTAAATTTCTCTGACTTTTGGTCATCAGTAGACTCGAACTGTGAGACTATCTCGGTTATG
ACAGCAGAAATGTCCTTCTTGGAGACAGTAAATGAAGTCCCACCAATAAAGAAATCCTTGTTATCAGGAA
CAAACTTCTTGTTTCGAACTTTTTCGGTGCCTTGAACTATAAAATGTAGAGTGGATATGTCGGGTAGGAA
TGGAGCGGGCAAATGCTTACCTTCTGGACCTTCAAGAGGTATGTAGGGTTTGTAGATACTGATGCCAACT
TCAGTGACAACGTTGCTATTTCGTTCAAACCATTCCGAATCCAGAGAAATCAAAGTTGTTTGTCTACTAT
TGATCCAAGCCAGTGCGGTCTTGAAACTGACAATAGTGTGCTCGTGTTTTGAGGTCATCTTTGTATGAAT
AAATCTAGTCTTTGATCTAAATAATCTTGACGAGCCAAGGCGATAAATACCCAAATCTAAAACTCTTTTA
AAACGTTAAAAGGACAAGTATGTCTGCCTGTATTAAACCCCAAATCAGCTCGTAGTCTGATCCTCATCAA
CTTGAGGGGCACTATCTTGTTTTAGAGAAATTTGCGGAGATGCGATATCGAGAAAAAGGTACGCTGATTT
TAAACGTGAAATTTATCTCAAGATCTCTGCCTCGCGCGTTTCGGTGATGACGGTGAAAACCTCTGACACA
TGCAGCTCCCGGAGACGGTCACAGCTTGTCTGTAAGCGGATGCCGGGAGCAGACAAGCCCGTCAGGGCGC
GTCAGCGGGTGTTGGCGGGTGTCGGGCGCAGCCATGACCCAGTCACGTAGCGATAGCGGAGTGTATACT
GGCTTAACTATGCGGCATCAGAGCAGATTGTACTGAGAGTGCACCATATGCGGTGTGAAATACCGCACAG
ATGCGTAAGGAGAAAATACCGCATCAGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATA
ACGCAGGAAAGAACATGTGAGCAAAAGGCCAGCAAAAGGCCAGGAACCGTAAAAAGGCCGCGTTGCTGGC
GTTTTTCCATAGGCTCCGCCCCCCTGACGAGCATCACAAAAATCGACGCTCAAGTCAGAGGTGGCGAAAC
CCGACAGGACTATAAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCAATGCTCACGCTG
TAGGTATCTCAGTTCGGTGTAGGTCGTTCGCTCCAAGCTGGGCTGTGTGCACGAACCCCCCGTTCAGCCC
GACCGCTGCGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTGAAGTGGTG
GCCTAACTACGGCTACACTAGAAGGACAGTATTTGGTATCTGCGCTCTGCTGAAGCCAGTTACCTTCGGA
AAAAGAGTTGGTAGCTCTTGATCCGGCAAACAAACCACCGCTGGTAGCGGTGGTTTTTTTGTTTGCAAGC
AGCAGATTACGCGCAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTTCACCTAGATCCTT
TTAAATTAAAAATGAAGTTTTAAATCAATCTAAAGTATATATGAGTAAACTTGGTCTGACAGTTACCAAT
GCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCA
CGCTCACCGGCTCCAGATTTATCAGCAATAAACCAGCCAGCCGGAAGGGCCGAGCGCAGAAGTGGTCCTG
CAACTTTATCCGCCTCCATCCAGTCTATTAATTGTTGCCGGGAAGCTAGAGTAAGTAGTTCGCCAGTTAA
TAGTTTGCGCAACGTTGTTGCCATTGCTGCAGGCATCGTGGTGTCACGCTCGTCGTTTGGTATGGCTTCA
TTCAGCTCCGGTTCCCAACGATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCACTCATGGTTATGGCAGCACT
GCATAATTCTCTTACTGTCATGCCATCCGTAAGATGCTTTTCTGTGACTGGTGAGTACTCAACCAAGTCA
TTCTGAGAATAGTGTATGCGGCGACCGAGTTGCTCTTGCCCGGCGTCAACACGGGATAATACCGCGCCAC
ATAGCAGAACTTTAAAAGTGCTCATCATTGGAAAACGTTCTTCGGGGCGAAAACTCTCAAGGATCTTACC
```

FIGURE 8, cont.

```
GCTGTTGAGATCCAGTTCGATGTAACCCACTCGTGCACCCAACTGATCTTCAGCATCTTTTACTTTCACC
AGCGTTTCTGGGTGAGCAAAAACAGGAAGGCAAAATGCCGCAAAAAGGGAATAAGGGCGACACGGAAAT
GTTGAATACTCATACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCCCCGAAAAGTGCCA
CCTGACGTCTAAGAAACCATTATTATCATGACATTAACCTATAAAAATAGGCGTATCACGAGGCCCTTTC
GTCTTCAAGAATTAATTCTCATGTTTGACAGCTTATCATCGATAAGCTGACTCATGTTGGTATTGTGAAA
TAGACGCAGATCGGGAACACTGAAAAATAACAGTTATTATTCG
```

FIGURE 9

Sequence of pPICpre-hITF$_{15-73}$ (SEQ ID NO: 6)

AGATCTAACATCCAAAGACGAAAGGTTGAATGAAACCTTTTTGCCATCCGACATCCACAGGTCCATTCTC
ACACATAAGTGCCAAACGCAACAGGAGGGGATACACTAGCAGCAGACCGTTGCAAACGCAGGACCTCCAC
TCCTCTTCTCCTCAACACCCACTTTTGCCATCGAAAAACCAGCCCAGTTATTGGGCTTGATTGGAGCTCG
CTCATTCCAATTCCTTCTATTAGGCTACTAACACCATGACTTTATTAGCCTGTCTATCCTGGCCCCCCTG
GCGAGGTTCATGTTTGTTTATTTCCGAATGCAACAAGCTCCGCATTACACCCGAACATCACTCCAGATGA
GGGCTTTCTGAGTGTGGGGTCAAATAGTTTCATGTTCCCCAAATGGCCCAAAACTGACAGTTTAAACGCT
GTCTTGGAACCTAATATGACAAAAGCGTGATCTCATCCAAGATGAACTAAGTTTGGTTCGTTGAAATGCT
AACGGCCAGTTGGTCAAAAAGAAACTTCCAAAAGTCGCCATACCGTTTGTCTTGTTTGGTATTGATTGAC
GAATGCTCAAAAATAATCTCATTAATGCTTAGCGCAGTCTCTCTATCGCTTCTGAACCCCGGTGCACCTG
TGCCGAAACGCAAATGGGGAAACACCCGCTTTTTGGATGATTATGCATTGTCTCCACATTGTATGCTTCC
AAGATTCTGGTGGGAATACTGCTGATAGCCTAACGTTCATGATCAAAATTTAACTGTTCTAACCCCTACT
TGACAGCAATATATAAACAGAAGGAAGCTGCCCTGTCTTAAACCTTTTTTTTTATCATCATTATTAGCTT
ACTTTCATAATTGCGACTGGTTCCAATTGACAAGCTTTTGATTTTAACGACTTTTAACGACAACTTGAGA
AGATCAAAAAACAACTAATTATTCGAAGGATCCAAACGATGAGATTTCCTTCAATTTTTACTGCAGTTTT
ATTCGCAGCATCCTCCGCATTAGCTGCT<u>CTCGAG</u>AAAAGAGAGGAGTACGTGGGCCTGTCTGCAAACCAGT
GTGCCGTGCCAGCCAAGGACAGGGTGGACTGCGGCTACCCCCATGTCACCCCCAAGGAGTGCAACAACCGG
GGCTGCTGCTTTGACTCCAGGATCCCTGGAGTGCCTTGGTGTTTCAAGCCCCTGCAGGAAGCAGAATGCAC
CTTCTGA<u>GAATTC</u>CCTAGGGCGGCCGCGAATTAATTCGCCTTAGACATGACTGTTCCTCAGTTCAAGTTGG
GCACTTACGAGAAGACCGGTCTTGCTAGATTCTAATCAAGAGGATGTCAGAATGCCATTTGCCTGAGAGAT
GCAGGCTTCATTTTTGATACTTTTTATTTGTAACCTATATAGTATAGGATTTTTTTGTCATTTTGTTTC
TTCTCGTACGAGCTTGCTCCTGATCAGCCTATCTCGCAGCTGATGAATATCTTGTGGTAGGGGTTTGGGAA
AATCATTCGAGTTTGATGTTTTTCTTGGTATTTCCCACTCCTCTTCAGAGTACAGAAGATTAAGTGAGAAG
TTCGTTTGTGCAAGCTTATCGATAAGCTTTAATGCGGTAGTTTATCACAGTTAAATTGCTAACGCAGTCAG
GCACCGTGTATGAAATCTAACAATGCGCTCATCGTCATCCTCGGCACCGTCACCCTGGATGCTGTAGGCAT
AGGCTTGGTTATGCCGGTACTGCCGGGCCTCTTGCGGGATATCGTCCATTCCGACAGCATCGCCAGTCACT
ATGGCGTGCTGCTAGCGCTATATGCGTTGATGCAATTTCTATGCGCACCCGTTCTCGGAGCACTGTCCGAC
CGCTTTGGCCGCCGCCCAGTCCTGCTCGCTTCGCTACTTGGAGCCACTATCGACTACGCGATCATGGCGAC
CACACCCGTCCTGTGGATCTATCGAATCTAAATGTAAGTTAAAATCTCTAAATAATTAAATAAGTCCCAGT
TTCTCCATACGAACCTTAACAGCATTGCGGTGAGCATCTAGACCTTCAACAGCAGCCAGATCCATCACTGC
TTGGCCAATATGTTTCAGTCCCTCAGGAGTTACGTCTTGTGAAGTGATGAACTTCTGGAAGGTTGCAGTGT
TAACTCCGCTGTATTGACGGGCATATCCGTACGTTGGCAAAGTGTGGTTGGTACCGGAGGAGTAATCTCCA
CAACTCTCTGGAGAGTAGGCACCAACAAACACAGATCCAGCGTGTTGTACTTGATCAACATAAGAAGAAGC
ATTCTCGATTTGCAGGATCAAGTGTTCAGGAGCGTACTGATTGGACATTTCCAAAGCCTGCTCGTAGGTTG
CAACCGATAGGGTTGTAGAGTGTGCAATACACTTGCGTACAATTTCAACCCTTGGCAACTGCACAGCTTGG
TTGTGAACAGCATCTTCAATTCTGGCAAGCTCCTTGTCTGTCATATCGACAGCCAACAGAATCACCTGGGA
ATCAATACCATGTTCAGCTTGAGACAGAAGGTCTGAGGCAACGAAATCTGGATCAGCGTATTTATCAGCAA
TAACTAGAACTTCAGAAGGCCCAGCAGGCATGTCAATACTACACAGGGCTGATGTGTCATTTTGAACCATC
ATCTTGGCAGCAGTAACGAACTGGTTTCCTGGACCAAATATTTTGTCACACTTAGGAACAGTTTCTGTTCC
GTAAGCCATAGCAGCTACTGCCTGGGCGCCTCCTGCTAGCACGATACACTTAGCACCAACCTTGTGGGCAA
CGTAGATGACTTCTGGGGTAAGGGTACCATCCTTCTTAGGTGGAGATGCAAAAACAATTTCTTTGCAACCA
GCAACTTTGGCAGGAACACCCAGCATCAGGGAAGTGGAAGGCAGAATTGCGGTTCCACCAGGAATATAGAG
GCCAACTTTCTCAATAGGTCTTGCAAAACGAGAGCAGACTACACCAGGGCAAGTCTCAACTTGCAACGTCT
CCGTTAGTTGAGCTTCATGGAATTTCCTGACGTTATCTATAGAGATCAATGGCTCTCTTAACGTTATCT
GGCAATTGCATAAGTTCCTCTGGGAAAGGAGCTTCTAACACAGGTGTCTTCAAAGCGACTCCATCAAACTT
GGCAGTTAGTTCTAAAAGGGCTTTGTCACCATTTTGACGAACATTGTCGACAATTGGTTTGACTAATTCCA
TAATCTGTTCCGTTTTCTGGATAGGACGACGAAGGGCATCTTCAATTTCTTGTGAGGAGGCCTTAGAAACG
TCAATTTTGCACAATTCAATACGACCTTCAGAAGGGACTTCTTTAGGTTTGGATTCTTCTTTAGGTTGTTC
CTTGGTGTATCCTGGCTTGGCATCTCCTTTCCTTCTAGTGACCTTTAGGGACTTCATATCCAGGTTTCTCT

FIGURE 9, cont.

```
CCACCTCGTCCAACGTCACACCGTACTTGGCACATCTAACTAATGCAAAATAAAATAAGTCAGCACATTCC
CAGGCTATATCTTCCTTGGATTTAGCTTCTGCAAGTTCATCAGCTTCCTCCCTAATTTTAGCGTTCAACAA
AACTTCGTCGTCAAATAACCGTTTGGTATAAGAACCTTCTGGAGCATTGCTCTTACGATCCCACAAGGTGG
CTTCCATGGCTCTAAGACCCTTTGATTGGCCAAAACAGGAAGTGCGTTCCAAGTGACAGAAACCAACACCT
GTTTGTTCAACCACAAATTTCAAGCAGTCTCCATCACAATCCAATTCGATACCCAGCAACTTTTGAGTTGC
TCCAGATGTAGCACCTTTATACCACAAACCGTGACGACGAGATTGGTAGACTCCAGTTTGTGTCCTTATAG
CCTCCGGAATAGACTTTTTGGACGAGTACACCAGGCCCAACGAGTAATTAGAAGAGTCAGCCACCAAAGTA
GTGAATAGACCATCGGGGCGGTCAGTAGTCAAAGACGCCAACAAAATTTCACTGACAGGGAACTTTTTGAC
ATCTTCAGAAAGTTCGTATTCAGTAGTCAATTGCCGAGCATCAATAATGGGGATTATACCAGAAGCAACAG
TGGAAGTCACATCTACCAACTTTGCGGTCTCAGAAAAAGCATAAACAGTTCTACTACCGCCATTAGTGAAA
CTTTTCAAATCGCCCAGTGGAGAAGAAAAAGGCACAGCGATACTAGCATTAGCGGGCAAGGATGCAACTTT
ATCAACCAGGGTCCTATAGATAACCCTAGCGCCTGGATCATCCTTTGGACAACTCTTTCTGCCAAATCTA
GGTCCAAAATCACTTCATTGATACCATTATTGTACAACTTGAGCAAGTTGTCGATCAGCTCCTCAAATTGG
TCCTCTGTAACGGATGACTCAACTTGCACATTAACTTGAAGCTCAGTCGATTGAGTGAACTTGATCAGGTT
GTGCAGCTGGTCAGCAGCATAGGGAAACACGGCTTTTCCTACCAAACTCAAGGAATTATCAAACTCTGCAA
CACTTGCGTATGCAGGTAGCAAGGGAAATGTCATACTTGAAGTCGGACAGTGAGTGTAGTCTTGAGAAATT
CTGAAGCCGTATTTTTATTATCAGTGAGTCAGTCATCAGGAGATCCTCTACGCCGGACGCATCGTGGCCGG
CATCACCGGCGCCACAGGTGCGGTTGCTGGCGCCTATATCGCCGACATCACCGATGGGGAAGATCGGGCTC
GCCACTTCGGGCTCATGAGCGCTTGTTTCGGCGTGGGTATGGTGGCAGGCCCCGTGGCCGGGGGACTGTTG
GGCGCCATCTCCTTGCATGCACCATTCCTTGCGGCGGCGGTGCTCAACGGCCTCAACCTACTACTGGGCTG
CTTCCTAATGCAGGAGTCGCATAAGGGAGAGCGTCGAGTATCTATGATTGGAAGTATGGGAATGGTGATAC
CCGCATTCTTCAGTGTCTTGAGGTCTCCTATCAGATTATGCCCAACTAAAGCAACCGGAGGAGGAGATTTC
ATGGTAAATTTCTCTGACTTTTGGTCATCAGTAGACTCGAACTGTGAGACTATCTCGGTTATGACAGCAGA
AATGTCCTTCTTGGAGACAGTAAATGAAGTCCCACCAATAAAGAAATCCTTGTTATCAGGAACAAACTTCT
TGTTTCGAACTTTTTCGGTGCCTTGAACTATAAAATGTAGAGTGGATATGTCGGGTAGGAATGGAGCGGGC
AAATGCTTACCTTCTGGACCTTCAAGAGGTATGTAGGGTTTGTAGATACTGATGCCAACTTCAGTGACAAC
GTTGCTATTTCGTTCAAACCATTCCGAATCCAGAGAAATCAAAGTTGTTTGTCTACTATTGATCCAAGCCA
GTGCGGTCTTGAAACTGACAATAGTGTGCTCGTGTTTTGAGGTCATCTTTGTATGAATAAATCTAGTCTTT
GATCTAAATAATCTTGACGAGCCAAGGCGATAAATACCCAAATCTAAAACTCTTTTAAAACGTTAAAAGGA
CAAGTATGTCTGCCTGTATTAAACCCCAAATCAGCTCGTAGTCTGATCCTCATCAACTTGAGGGGCACTAT
CTTGTTTTAGAGAAATTTGCGGAGATGCGATATCGAGAAAAAGGTACGCTGATTTTAAACGTGAAATTTAT
CTCAAGATCTCTGCCTCGCGCGTTTCGGTGATGACGGTGAAAACCTCTGACACATGCAGCTCCCGGAGACG
GTCACAGCTTGTCTGTAAGCGGATGCCGGGAGCAGACAAGCCCGTCAGGGCGCGTCAGCGGGTGTTGGCGG
GTGTCGGGGCGCAGCCATGACCCAGTCACGTAGCGATAGCGGAGTGTATACTGGCTTAACTATGCGGCATC
AGAGCAGATTGTACTGAGAGTGCACCATATGCGGTGTGAAATACCGCACAGATGCGTAAGGAGAAAATACC
GCATCAGGCGCTCTTCCGCTTCCTCGCTCACTGACTCGCTGCGCTCGGTCGTTCGGCTGCGGCGAGCGGTA
TCAGCTCACTCAAAGGCGGTAATACGGTTATCCACAGAATCAGGGGATAACGCAGGAAAGAACATGTGAGC
AAAAGGCCAGCAAAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTACCGGATACCTGTCCGC
CTTTCTCCCTTCGGGAAGCGTGGCGCTTTCTCAATGCTCACGCTGTAGGTATCTCAGTTCGGTGTAGGTCG
TTCGCTCCAAGCTGGGCTGTGTGCACGAACCCCCCGTTCAGCCCGACCGCTGCGCCTTATCCGGTAACTAT
CGTCTTGAGTCCAACCCGGTAAGACACGACTTATCGCCACTGGCAGCAGCCACTGGTAACAGGATTAGCAG
AGCGAGGTATGTAGGCGGTGCTACAGAGTTCTTGAAGTGGTGGCCTAACTACGGCTACACTAGAAGGACAG
TATTTGGTATCTGCGCTCTGCTGAAGCCAGTTACCTTCGGAAAAAGAGTTGGTAGCTCTTGATCCGGCAAA
CAAACCACCGCTGGTAGCGGTGGTTTTTTGTTTGCAAGCAGCAGATTACGCGCAGAAAAAAGGATCTCA
AGAAGATCCTTTGATCTTTTCTACGGGGTCTGACGCTCAGTGGAACGAAAACTCACGTTAAGGGATTTTGG
TCATGAGATTATCAAAAAGGATCTTCACCTAGATCCTTTTAAATTAAAAATGAAGTTTTAAATCAATCTAA
AGTATATATGAGTAAACTTGGTCTGACAGTTACCAATGCTTAATCAGTGAGGCACCTATCTCAGCGATCTG
TCTATTTCGTTCATCCATAGTTGCCTGACTCCCCGTCGTGTAGATAACTACGATACGGGAGGGCTTACCAT
CTGGCCCCAGTGCTGCAATGATACCGCGAGACCCACGCTCACCGGCTCCAGATTTATCAGCAATAAACCAG
CCAGCCGGAAGGGCCGAGCGCAGAAGTGGTCCTGCAACTTTATCCGCCTCCATCCAGTCTATTAATTGTTG
CCGGGAAGCTAGAGTAAGTAGTTCGCCAGTTAATAGTTTGCGCAACGTTGTTGCCATTGCTGCAGGCATCG
TGGTGTCACGCTCGTCGTTTGGTATGGCTTCATTCAGCTCCGGTTCCCAACGATCAAGGCGAGTTACATGA
TCCCCCATGTTGTGCAAAAAAGCGGTTAGCTCCTTCGGTCCTCCGATCGTTGTCAGAAGTAAGTTGGCCGC
AGTGTTATCACTCATGGTTATGGCAGCACTGCATAATTCTCTTACTGTCATGCCATCCGTAAGATGCTTTT
CTGTGACTGGTGAGTACTCAACCAAGTCATTCTGAGAATAGTGTATGCGGCGACCGAGTTGCTCTTGCCCG
```

FIGURE 9, cont.

GCGTCAACACGGGATAATACCGCGCCACATAGCAGAACTTTAAAAGTGCTCATCATTGGAAAACGTTCTTC
GGGGCGAAAACTCTCAAGGATCTTACCGCTGTTGAGATCCAGTTCGATGTAACCCACTCGTGCACCCAACT
GATCTTCAGCATCTTTTACTTTCACCAGCGTTTCTGGGTGAGCAAAAACAGGAAGGCAAAATGCCGCAAAA
AAGGGAATAAGGGCGACACGGAAATGTTGAATACTCATACTCTTCCTTTTTCAATATTATTGAAGCATTTA
TCAGGGTTATTGTCTCATGAGCGGATACATATTTGAATGTATTTAGAAAAATAAACAAATAGGGGTTCCGC
GCACATTTCCCCGAAAAGTGCCACCTGACGTCTAAGAAACCATTATTATCATGACATTAACCTATAAAAAT
AGGCGTATCACGAGGCCCTTTCGTCTTCAAGAATTAATTCTCATGTTTGACAGCTTATCATCGATAAGCTG
ACTCATGTTGGTATTGTGAAATAGACGCAGATCGGGAACACTGAAAAATAACAGTTATTATTCG

FIGURE 10

Sequence of pPICGIcoEA-hITF$_{15-73}$ (SEQ ID NO: 7)

AGATCTAACATCCAAAGACGAAAGGTTGAATGAAACCTTTTTGCCATCCGACATCCACAGGTCCATTCTC
ACACATAAGTGCCAAACGCAACAGGAGGGGATACACTAGCAGCAGACCGTTGCAAACGCAGGACCTCCAC
TCCTCTTCTCCTCAACACCCACTTTTGCCATCGAAAAACCAGCCCAGTTATTGGGCTTGATTGGAGCTCG
CTCATTCCAATTCCTTCTATTAGGCTACTAACACCATGACTTTATTAGCCTGTCTATCCTGGCCCCCCTG
GCGAGGTTCATGTTTGTTTATTTCCGAATGCAACAAGCTCCGCATTACACCCGAACATCACTCCAGATGA
GGGCTTTCTGAGTGTGGGGTCAAATAGTTTCATGTTCCCCAAATGGCCCAAAACTGACAGTTTAAACGCT
GTCTTGGAACCTAATATGACAAAAGCGTGATCTCATCCAAGATGAACTAAGTTTGGTTCGTTGAAATGCT
AACGGCCAGTTGGTCAAAAAGAAACTTCCAAAAGTCGCCATACCGTTTGTCTTGTTTGGTATTGATTGAC
GAATGCTCAAAAATAATCTCATTAATGCTTAGCGCAGTCTCTCTATCGCTTCTGAACCCCGGTGCACCTG
TGCCGAAACGCAAATGGGGAAACACCCGCTTTTTGGATGATTATGCATTGTCTCCACATTGTATGCTTCC
AAGATTCTGGTGGGAATACTGCTGATAGCCTAACGTTCATGATCAAAATTTAACTGTTCTAACCCCTACT
TGACAGCAATATATAAACAGAAGGAAGCTGCCCTGTCTTAAACCTTTTTTTTATCATCATTATTAGCTT
ACTTTCATAATTGCGACTGGTTCCAATTGACAAGCTTTTGATTTTAACGACTTTTAACGACAACTTGAGA
AGATCAAAAAACAACTAATTATTCGAAGGATCCAAACGATGAGATTTCCTTCAATTTTTACTGCAGTTTT
ATTCGCAGCATCCTCCGCATTAGCTGCTCCAGTCAACACTACAACAGAAGATGAAACGGCACAAATTCCG
GCTGAAGCTGTCATCGGTTACTCAGATTTAGAAGGGGATTTCGATGTTGCTGTTTTGCCATTTTCCAACA
GCACAAATAACGGGTTATTGTTTATAAATACTACTATTGCCAGCATTGCTGCTAAAGAAGAAGGGGTATC
TCTCGAGAAAGAGAGGCT**GAGGAGTACGTGGGCCTGTCTGCAAACCAGTGTGCCGTGCCAGCCAAGGACA
GGGTGGACTGCGGCTACCCCATGTCACCCCAAGGAGTGCAACAACCGGGGCTGCTGCTTTGACTCCAGG
ATCCCTGGAGTGCCTTGGTGTTTCAAGCCCCTGCAGGAAGCAGAATGCACCTTCTGA**GAATTCCCTAGGGC
GGCCGCGAATTAATTCGCCTTAGACATGACTGTTCCTCAGTTCAAGTTGGGCACTTACGAGAAGACCGGTC
TTGCTAGATTCTAATCAAGAGGATGTCAGAATGCCATTTGCCTGAGAGATGCAGGCTTCATTTTTGATACT
TTTTTATTTGTAACCTATATAGTATAGGATTTTTTTTGTCATTTGTTTCTTCTCGTACGAGCTTGCTCCT
GATCAGCCTATCTCGCAGCTGATGAATATCTTGTGGTAGGGGTTTGGGAAAATCATTCGAGTTTGATGTTT
TTCTTGGTATTTCCCACTCCTCTTCAGAGTACAGAAGATTAAGTGAGAAGTTCGTTTGTGCAAGCTTATCG
ATAAGCTTTAATGCGGTAGTTTATCACAGTTAAATTGCTAACGCAGTCAGGCACCGTGTATGAAATCTAAC
AATGCGCTCATCGTCATCCTCGGCACCGTCACCCTGGATGCTGTAGGCATAGGCTTGGTTATGCCGGTACT
GCCGGGCCTCTTGCGGGATATCGTCCATTCCGACAGCATCGCCAGTCACTATGGCGTGCTGCTAGCGCTAT
ATGCGTTGATGCAATTTCTATGCGCACCCGTTCTCGGAGCACTGTCCGACCGCTTTGGCCGCCGCCCAGTC
CTGCTCGCTTCGCTACTTGGAGCCACTATCGACTACGCGATCATGGCGACCACACCCGTCCTGTGGATCTA
TCGAATCTAAATGTAAGTTAAAATCTCTAAATAATTAAATAAGTCCCAGTTTCTCCATACGAACCTTAACA
GCATTGCGGTGAGCATCTAGACCTTCAACAGCAGCCAGATCCATCACTGCTTGGCCAATATGTTTCAGTCC
CTCAGGAGTTACGTCTTGTGAAGTGATGAACTTCTGGAAGGTTGCAGTGTTAACTCCGCTGTATTGACGGG
CATATCCGTACGTTGGCAAAGTGTGGTTGGTACCGGAGGAGTAATCTCCACAACTCTCTGGAGAGTAGGCA
CCAACAAACACAGATCCAGCGTGTTGTACTTGATCAACATAAGAAGAAGCATTCTCGATTTGCAGGATCAA
GTGTTCAGGAGCGTACTGATTGGACATTTCCAAAGCCTGCTCGTAGGTTGCAACCGATAGGGTTGTAGAGT
GTGCAATACACTTGCGTACAATTTCAACCCTTGGCAACTGCACAGCTTGGTTGTGAACAGCATCTTCAATT
CTGGCAAGCTCCTTGTCTGTCATATCGACAGCCAACAGAATCACCTGGGAATCAATACCATGTTCAGCTTG
AGACAGAAGGTCTGAGGCAACGAAATCTGGATCAGCGTATTTATCAGCAATAACTAGAACTTCAGAAGGCC
CAGCAGGCATGTCAATACTACACAGGGCTGATGTGTCATTTGAACCATCATCTTGGCAGCAGTAACGAAC
TGGTTTCCTGGACCAAATATTTTGTCACACTTAGGAACAGTTTCTGTTCCGTAAGCCATAGCAGCTACTGC
CTGGGCGCCTCCTGCTAGCACGATACACTTAGCACCAACCTTGTGGGCAACGTAGATGACTTCTGGGGTAA
GGGTACCATCCTTCTTAGGTGGAGATGCAAAAACAATTTCTTTGCAACCAGCAACTTTGGCAGGAACACCC
AGCATCAGGGAAGTGGAAGGCAGAATTGCGGTTCCACCAGGAATATAGAGGCCAACTTTCTCAATAGGTCT
TGCAAAACGAGAGCAGACTACACCAGGGCAAGTCTCAACTTGCAACGTCTCCGTTAGTTGAGCTTCATGGA
ATTTCCTGACGTTATCTATAGAGAGATCAATGGCTCTCTTAACGTTATCTGGCAATTGCATAAGTTCCTCT
GGGAAAGGAGCTTCTAACACAGGTGTCTTCAAAGCGACTCCATCAAACTTGGCAGTTAGTTCTAAAAGGGC
TTTGTCACCATTTTGACGAACATTGTCGACAATTGGTTTGACTAATTCCATAATCTGTTCCGTTTTCTGGA

FIGURE 10, cont.

```
TAGGACGACGAAGGGCATCTTCAATTTCTTGTGAGGAGGCCTTAGAAACGTCAATTTTGCACAATTCAATA
CGACCTTCAGAAGGGACTTCTTTAGGTTTGGATTCTTCTTTAGGTTGTTCCTTGGTGTATCCTGGCTTGGC
ATCTCCTTTCCTTCTAGTGACCTTTAGGGACTTCATATCCAGGTTTCTCTCCACCTCGTCCAACGTCACAC
CGTACTTGGCACATCTAACTAATGCAAAATAAAATAAGTCAGCACATTCCCAGGCTATATCTTCCTTGGAT
TTAGCTTCTGCAAGTTCATCAGCTTCCTCCCTAATTTTAGCGTTCAACAAAACTTCGTCGTCAAATAACCG
TTTGGTATAAGAACCTTCTGGAGCATTGCTCTTACGATCCCACAAGGTGGCTTCCATGGCTCTAAGACCCT
TTGATTGGCCAAAACAGGAAGTGCGTTCCAAGTGACAGAAACCAACACCTGTTTGTTCAACCACAAATTTC
AAGCAGTCTCCATCACAATCCAATTCGATACCCAGCAACTTTTGAGTTGCTCCAGATGTAGCACCTTTATA
CCACAAACCGTGACGACGAGATTGGTAGACTCCAGTTTGTGTCCTTATAGCCTCCGGAATAGACTTTTTGG
ACGAGTACACCAGGCCCAACGAGTAATTAGAAGAGTCAGCCACCAAAGTAGTGAATAGACCATCGGGGCGG
TCAGTAGTCAAAGACGCCAACAAAATTTCACTGACAGGGAACTTTTTGACATCTTCAGAAAGTTCGTATTC
AGTAGTCAATTGCCGAGCATCAATAATGGGGATTATACCAGAAGCAACAGTGGAAGTCACATCTACCAACT
TTGCGGTCTCAGAAAAAGCATAAACAGTTCTACTACCGCCATTAGTGAAACTTTTCAAATCGCCCAGTGGA
GAAGAAAAAGGCACAGCGATACTAGCATTAGCGGGCAAGGATGCAACTTTATCAACCAGGGTCCTATAGAT
AACCCTAGCGCCTGGGATCATCCTTTGGACAACTCTTTCTGCCAAATCTAGGTCCAAATCACTTCATTGA
TACCATTATTGTACAACTTGAGCAAGTTGTCGATCAGCTCCTCAAATTGGTCCTCTGTAACGGATGACTCA
ACTTGCACATTAACTTGAAGCTCAGTCGATTGAGTGAACTTGATCAGGTTGTGCAGCTGGTCAGCAGCATA
GGGAAACACGGCTTTTCCTACCAAACTCAAGGAATTATCAAACTCTGCAACACTTGCGTATGCAGGTAGCA
AGGGAAATGTCATACTTGAAGTCGGACAGTGAGTGTAGTCTTGAGAAATTCTGAAGCCGTATTTTATTAT
CAGTGAGTCAGTCATCAGGAGATCCTCTACGCCGGACGCATCGTGGCCGGCATCACCGGCGCCACAGGTGC
GGTTGCTGGCGCCTATATCGCCGACATCACCGATGGGGAAGATCGGGCTCGCCACTTCGGGCTCATGAGCG
CTTGTTTCGGCGTGGGTATGGTGGCAGGCCCCGTGGCCGGGGACTGTTGGGCGCCATCTCCTTGCATGCA
CCATTCCTTGCGGCGGCGGTGCTCAACGGCCTCAACCTACTACTGGGCTGCTTCCTAATGCAGGAGTCGCA
TAAGGGAGAGCGTCGAGTATCTATGATTGGAAGTATGGGAATGGTGATACCCGCATTCTTCAGTGTCTTGA
GGTCTCCTATCAGATTATGCCCAACTAAAGCAACCGGAGGAGGAGATTTCATGGTAAATTTCTCTGACTTT
TGGTCATCAGTAGACTCGAACTGTGAGACTATCTCGGTTATGACAGCAGAAATGTCCTTCTTGGAGACAGT
AAATGAAGTCCCACCAATAAAGAAATCCTTGTTATCAGGAACAAACTTCTTGTTTCGAACTTTTTCGGTGC
CTTGAACTATAAAATGTAGAGTGGATATGTCGGGTAGGAATGGAGCGGGCAAATGCTTACCTTCTGGACCT
TCAAGAGGTATGTAGGGTTTGTAGATACTGATGCCAACTTCAGTGACAACGTTGCTATTTCGTTCAAACCA
TTCCGAATCCAGAGAAATCAAAGTTGTTTGTCTACTATTGATCCAAGCCAGTGCGGTCTTGAAACTGACAA
TAGTGTGCTCGTGTTTTGAGGTCATCTTTGTATGAATAAATCTAGTCTTTGATCTAAATAATCTTGACGAG
CCAAGGCGATAAATACCCAAATCTAAAACTCTTTTAAAACGTTAAAAGGACAAGTATGTCTGCCTGTATTA
AACCCCAAATCAGCTCGTAGTCTGATCCTCATCAACTTGAGGGGCACTATCTTGTTTTAGAGAAATTTGCG
GAGATGCGATATCGAGAAAAAGGTACGCTGATTTTAAACGTGAAATTTATCTCAAGATCTCTGCCTCGCGC
GTTTCGGTGATGACGGTGAAAACCTCTGACACATGCAGCTCCCGGAGACGGTCACAGCTTGTCTGTAAGCG
GATGCCGGGAGCAGACAAGCCCGTCAGGGCGCGTCAGCGGGTGTTGGCGGGTGTCGGGGCGCAGCCATGAC
CCAGTCACGTAGCGATAGCGGAGTGTATACTGGCTTAACTATGCGGCATCAGAGCAGATTGTACTGAGAGT
GCACCATATGCGGTGTGAAATACCGCACAGATGCGTAAGGAGAAAATACCGCATCAGGCGCTCTTCCGCTT
CCTCGCTCACTGACTCGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCCTGACGAGCATCACAAAAATC
GACGCTCAAGTCAGAGGTGGCGAAACCCGACAGGACTATAAAGATACCAGGCGTTTCCCCCTGGAAGCTCC
CTCGTGCGCTCTCCTGTTCCGACCCTGCCGCTTACCGGATACCTGTCCGCCTTTCTCCCTTCGGGAAGCGT
GGCGCTTTCTCAATGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAGTCCAACCCGGTA
AGACACGACTTATCGCCACTGGCAGCAGCCACTGGTAACAGGATTAGCAGAGCGAGGTATGTAGGCGGTGC
TACAGAGTTCTTGAAGTGGTGGCCTAACTACGGCTACACTAGAAGGACAGTATTTGGTATCTGCGCTCTGC
TGAAGCCAGTTACCTTCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAGGATCTCAAGAAGATCCTTTGATCTTTTC
TACGGGGTCTGACGCTCAGTGGAACGAAAACTCACGTTAAGGGATTTTGGTCATGAGATTATCAAAAGGA
TCTTCACCTAGATCCTTTTAAATTAAAAATGAAGTTTTAAATCAATCTAAAGTATATATGAGTAAACTTGG
TCTGACAGTTACCAATGCTTAATCAGTGAGGCACCTATCTCAGCGATCTGTCTATTTCGTTCATCCATAGT
TGCCTGACTCCCCGTCGTGTAGATAACTACGATACGGGAGGGCTTACCATCTGGCCCCAGTGCTGCAATGA
TACCGCGAGACCCACGCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAAGCTAGAGTAAGTAG
TTCGCCAGTTAATAGTTTGCGCAACGTTGTTGCCATTGCTGCAGGCATCGTGGTGTCACGCTCGTCGTTTG
GTATGGCTTCATTCAGCTCCGGTTCCCAACGATCAAGGCGAGTTACATGATCCCCCATGTTGTGCAAAAAA
```

FIGURE 10, cont.

```
GCGGTTAGCTCCTTCGGTCCTCCGATCGTTGTCAGAAGTAAGTTGGCCGCAGTGTTATCACTCATGGTTAT
GGCAGCACTGCATAATTCTCTTACTGTCATGCCATCCGTAAGATGCTTTTCTGTGACTGGTGAGTACTCAA
CCAAGTCATTCTGAGAATAGTGTATGCGGCGACCGAGTTGCTCTTGCCCGGCGTCAACACGGGATAATACC
GCGCCACATAGCAGAACTTTAAAAGTGCTCATCATTGGAAAACGTTCTTCGGGGCGAAAACTCTCAAGGAT
CTTAGCTGTTGAGATCCAGTTCGATGTAACCCACTCGTGCACCCAACTGATCTTCAGCATCTTTTACTTTC
ACCAGCGTTTCTGGGTGAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATTGTCTCATGAGCG
GATACATATTTGAATGTATTTAGAAAAATAAACAAATAGGGGTTCCGCGCACATTTCCCCGAAAAGTGCCA
CCTGACGTCTAAGAAACCATTATTATCATGACATTAACCTATAAAAATAGGCGTATCACGAGGCCCTTTCG
TCTTCAAGAATTAATTCTCATGTTTGACAGCTTATCATCGATAAGCTGACTCATGTTGGTATTGTGAAATA
GACGCAGATCGGGAACACTGAAAAATAACAGTTATTATTCG
```

FIGURE 11A

Construction of pPICGIco yeast expression vector without Glu-Ala spacer

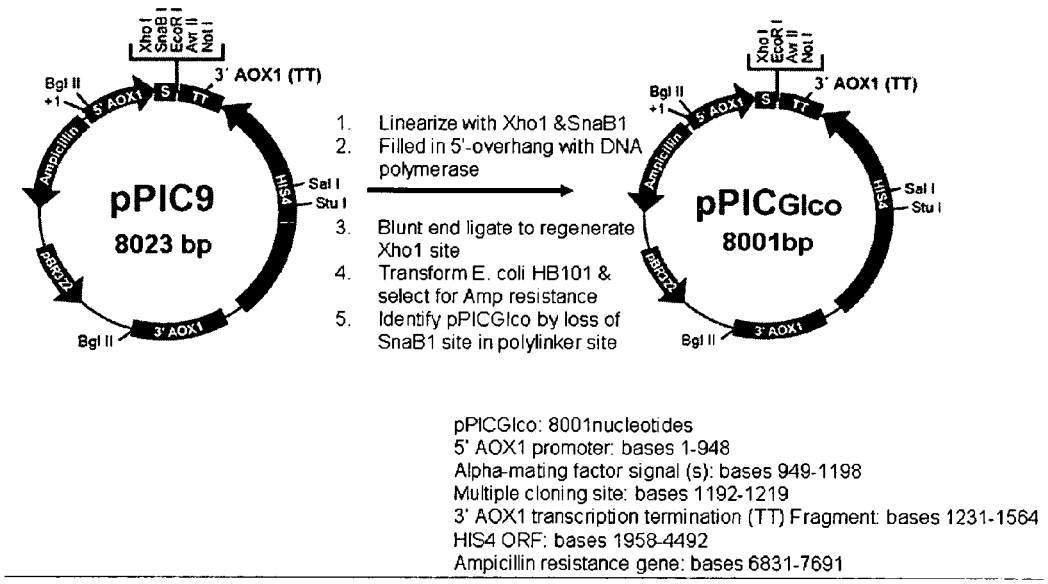

pPICGIco: 8001nucleotides
5' AOX1 promoter: bases 1-948
Alpha-mating factor signal (s): bases 949-1198
Multiple cloning site: bases 1192-1219
3' AOX1 transcription termination (TT) Fragment: bases 1231-1564
HIS4 ORF: bases 1958-4492
Ampicillin resistance gene: bases 6831-7691

FIGURE 11B pPICGIco multiple cloning site

```
              Xho1         EcoR1   AvrIII        Not1
               ↓             ↓       ↓            ↓
           5'- CTC GAG TAG AAT TCC CTA GGG CGG CCG
α-Mating factor prepro-sequence- -Leu  Glu  Stop
```

(SEQ ID NO: 243)

pPICpre Vector Map (SEQ ID NO: 131)

GGATCCAAACG ATGAGATTTC CTTCTATTTT TACTGCAGTT TTATTCGCTG
CATCCTCCGC ATTAGCTGCT CTCGAG pPICpre multiple cloning site (SEQ ID NO: 244)

AOX1----5'-ggatccaaacg atgagatttc cttctatttt tactgcagtt ttattcgctg catcctccgc
              M  R  F  P  S  I  F  T  A  V  L  F  A  A  S  S  A
    XhoI    EcoRI
attagctgct ctcgagtaga attc.....-3'             (SEQ ID NO: 405)
  L  A  A  L  E
    ↑ Signal peptidase cleavage site

FIGURE 13A

Nucleotide sequence of human ITF cDNA (SEQ ID NO: 101)

```
  1 GGAGTCCTGA GCTGCGTCCC GGAGCCCACG GTGGTCATGG CTGCCAGAGC GCTCTGCATG
 61 CTGGGGCTGG TCCTGGCCTT GCTGTCCTCC AGCTCTGCTG AGGAGTACGT GGGCCTGTCT
121 GCAAACCAGT GTGCCGTGCC AGCCAAGGAC AGGGTGGACT GCGGCTACCC CCATGTCACC
181 CCCAAGGAGT GCAACAACCG GGGCTGCTGC TTTGACTCCA GGATCCCTGG AGTGCCTTGG
241 TGTTTCAAGC CCCTGCAGGA AGCAGAATGC ACCTTCTGAG GCACCTCCAG CTGCCCCCGG
301 CCGGGGGATG CGAGGCTCGG AGCACCCTTG CCCGGCTGTG ATTGCTGCCA GGCACTGTTC
361 ATCTCAGCTT TTCTGTCCCT TTGCTCCCGG CAAGCGCTTC TGCTGAAAGT TCATATCTGG
421 AGCCTGATGT CTTAACGAAT AAAGGTCCCA TGCTCCACCC TAAAAAAAAA AAAAAAAAAA
481 AAAAAAAAA A
```

FIGURE 13B

Nucleotide sequence of pig ITF cDNA (SEQ ID NO: 102)

```
  1 ATGGAGGCCA GGATGTTCTG GCTGCTAGTG GTGCTCCTGG CCTTGGCGTC CTCCAGCTCT
 61 GCCGGGGAGT ATGTGGGCCT GTCGGCGAAC CAGTGTGCCG TCCCTGCCAA GGACAGGGTG
121 GACTGCGGCT ACCCCCAGGT CACCCCCGAG CAGTGCAACA ACCGGGGCTG CTGCTTCGAC
181 TCCAGCATCC CCGGGGTGCC CTGGTGCTTC AAGCCCCTGC AGGAAACAGA ATGCACCTTC
241 TGA
```

FIGURE 13C

Nucleotide sequence of dog ITF cDNA (SEQ ID NO: 103)

```
  1 AACGATCTCT GAGCGGTCGG GTCCCCAGAG CCCACCCGTG ACCATGGAGG CCAGAGTGCT
 61 CTGGCTGCTG GTGGTGGTCC TGGTCCTGGG GTCCTCCAGC TTGGCAGTGG CTTACCAGGG
121 CCTGGCGACG AACCTGTGCG AGGTGCCGCC CAAGGACAGG GTGGACTGCG GCTACCCTGA
181 GATCACCTCC GAGCAGTGCG TCAATCGGGG CTGCTGCTTC GACTCCAGCA TCCACGGGGT
241 GCCCTGGTGC TTCAAGCCGT GCAGGACAC AGAATGCAGA TTTTGAAGCA ACGCCCTCGA
301 CCCCGGACAC CCTGGGAAGC
```

FIGURE 13D

Nucleotide sequence of rat ITF cDNA (SEQ ID NO: 104)

```
  1 GAAGTTTGCG TGCTGCCATG GAGACCAGAG CCTTCTGGAC AACCCTGCTG CTGGTCCTGG
 61 TTGCTGGGTC CTCCTGCAAA GCCCAGGAAT TTGTTGGCCT ATCTCCAAGC CAATGTATGG
121 CTCCAACAAA TGTCAGGGTG GACTGTAACT ACCCCACTGT CACATCAGAG CAGTGTAACA
181 ACCGTGGTTG CTGTTTTGAC TCCAGCATCC CAAATGTGCC CTGGTGCTTC AAACCTCTGC
241 AAGAGACAGA ATGTACATTT TGAAGCTGTC CAGGCTCCAG GAAGGGAGCT CCACACCCTG
301 GACTCTTGCT GATGGTAGTG GCCCAGGGTA ACACTCACCC CTGATCTGCT CCCTCGCGCC
361 GGCCAATATA GGAGCTGGGA GTCCAGAAGA ATAAAGACCT TACAGTCAGC ACAAGGCTGT
421 TCTAATTGCG G
```

FIGURE 13E

Nucleotide sequence of mouse ITF cDNA (SEQ ID NO: 105)

```
  1 ATCCTGTGCA GTGGTCCTGA AGCTTGCCTG CTGCCATGGA GACCAGAGCC CTCTGGCTAA
 61 TGCTGTTGGT GGTCCTGGTT GCTGGGTCCT CTGGGATAGC TGCAGATTAC GTTGGCCTGT
121 CTCCAAGCCA ATGTATGGTG CCGGCAAATG TCAGAGTGGA CTGTGGCTAC CCCTCTGTCA
181 CATCGGAGCA GTGTAACAAC CGTGGCTGCT GCTTTGACTC CAGTATCCCA AATGTGCCCT
241 GGTGCTTCAA ACCTCTGCAG GAGACAGAAT GCACATTTTG AAGCTGTCCA GGCTCCAGGA
301 AGGGAGCTCT GCACCCTGGA CTCCTGCTGC TGATGGTGGT CCAAGGGTAG CAAGCATCCC
361 CGATCTGCTC CCTGCTGCAG GCCAATAAAG GAGCCAGGAG TCCTGAAGAA TAAAGACCTC
421 ACAGCCAACA CAAGGCTGAT CTGATTGCTG
```

FIGURE 14A

Amino acid sequence of full-length human ITF (SEQ ID NO: 301)

$M^1$LGLVLALLSSSSAE$^{15}$EYVGLSANQCAVPAKDRVDCGYPHVTPKECNNRGCCFDSRIP
GVPWCFKPLQEAECTF$^{73}$

FIGURE 14B

Amino acid sequence of full-length pig ITF (SEQ ID NO: 302)

$M^1$EARMFWLLVVLLALASSSSAG$^{22}$EYVGLSANQCAVPARDRVDCGYPQVTPEQCNNRGC
CFDSSIPGVPWCFKPLQETECTF$^{80}$

FIGURE 14C

Amino acid sequence of full-length dog ITF (SEQ ID NO: 303)

$M^1$EARVLWLLVVVLVLGSSSLAV$^{22}$AYQGLATNLCEVPPKDRVDCGYPEITSEQCVNRGC
CFDSSIHGVPWCFKPLQDTECRF$^{80}$

FIGURE 14D

Amino acid sequence of full-length rat ITF (SEQ ID NO: 304)

$M^1$ETRAFWTTLLLVLVAGSSCKAQ$^{23}$EFVGLSPSQCMAPTNVRVDCNYPTVTSEQCNNRG
CCFDSSIPNVPWCFKPLQETECTF$^{81}$

FIGURE 14E

Amino acid sequence of full-length mouse ITF (SEQ ID NO: 305)

$M^1$ETRALWLMLLVVLVAGSSGIAA$^{23}$DYVGLSPSQCMVPANVRVDCGYPSVTSEQCNNRG
CCFDSSIPNVPWCFKPLQETECTF$^{81}$

Subcloning of human ITF into pCR2.1

(SEQ ID NO: 106)

5'-<u>ctgccagagc gctctgcatg</u> ctggggctgg tcctggcctt gctgtcctcc agctctgctg aggagtacgt gggcctgtct gcaaaccagt gtgccgtgcc agccaaggac agggtggact gcggctaccc ccatgtcacc cccaaggagt gcaacaaccg gggctgctgc tttgactcca ggatccctgg agtgccttgg tgtttcaagc ccctgcagga agcagaatgc <u>accttctgag gcacctccag</u>-3'

Subcloning of pig ITF into pCR2.1

(SEQ ID NO: 107)

5'- atggaggcca ggatgttctg gctgctagtg gtgctcctgg ccttggcgtc ctccagctct gccggggagt
atgtgggcct gtcggcgaac cagtgtgccg tccctgccaa ggacagggtg gactgcggct accccccaggt
cacccccgag cagtgcaaca accggggctg ctgcttcgac tccagcatcc ccggggtgcc ctggtgcttc
aagcccctgc aggaaacaga atgcaccttc tga-3'

FIGURE 15C

Subcloning of dog ITF into pCR2.1

(SEQ ID NO: 108)

<u>5'-aacgatctct gagcggtcgg</u> gtccccagag cccacccgtg accatggagg ccagagtgct ctggctgctg
Gtggtggtcc tggtcctggg gtcctccagc ttggcagtgg cttaccaggg cctggcgacg aacctgtgcg
aggtgccgcc caaggacagg gtggactgcg gctaccctga gatcacctcc gagcagtgcg tcaatcgggg
ctgctgcttc gactccagca tccacggggt gccctggtgc ttcaagccgt tgcaggacac <u>agaatgcaga</u>
<u>ttttgaagca-3'</u>

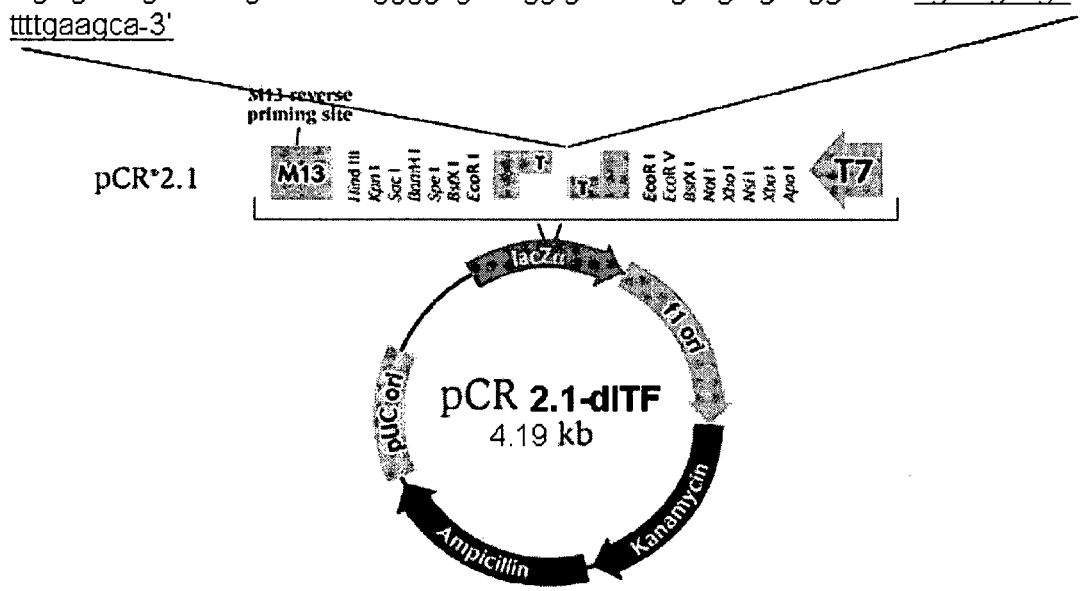

FIGURE 15D

Subcloning of rat ITF into pCR2.1

(SEQ ID NO: 109)

5'-<u>tgctgccatg gagaccagag</u> ccttctggac aaccctgctg ctggtcctgg ttgctgggtc ctcctgcaaa gcccaggaat ttgttggcct atctccaagc caatgtatgg ctccaacaaa tgtcagggtg gactgtaact accccactgt cacatcagag cagtgtaaca accgtggttg ctgttttgac tccagcatcc caaatgtgcc ctggtgcttc aaacctctgc aagagacaga atgtacattt <u>tgaagctgtc caggctccag</u>-3'

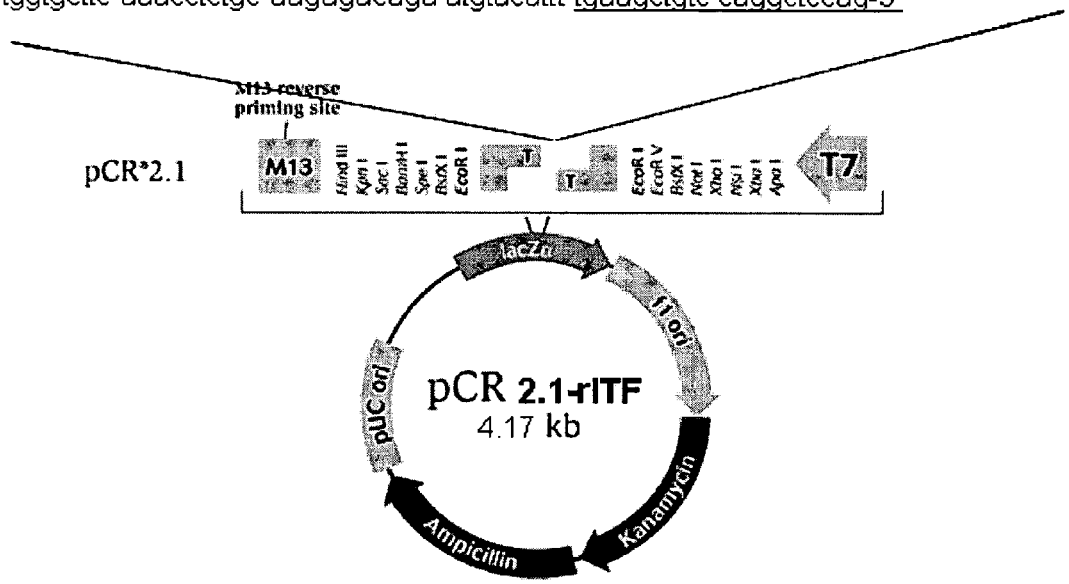

FIGURE 15E

Subcloning of mouse ITF into pCR2.1

(SEQ ID NO: 110)

5'-<u>agcttgcctg ctgccatgga</u> gaccagagcc ctctggctaa tgctgttggt ggtcctggtt gctgggtcct
ctgggatagc tgcagattac gttggcctgt ctccaagcca atgtatggtg ccggcaaatg tcagagtgga
ctgtggctac ccctctgtca catcggagca gtgtaacaac cgtggctgct gctttgactc cagtatccca
Aatgtgccct ggtgcttcaa acctctgcag gagacagaat gcacattttg <u>aagctgtcca ggctccagga</u>-3'

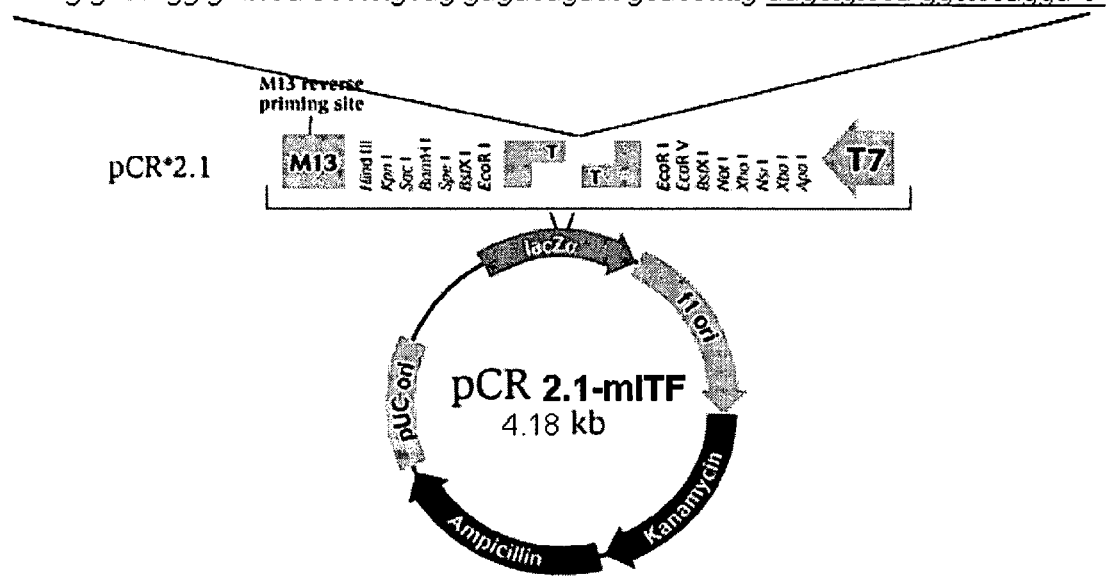

Subcloning of hITF$_{15-73}$ into pPICGIco (SEQ ID NO: 111)

5'-ctcgagaaaagag aggagtacgt gggcctgtct gcaaaccagt gtgccgtgcc
agccaaggac agggtggact gcggctaccc ccatgtcacc cccaaggagt
gcaacaaccg gggctgctgc tttgactcca ggatccctgg agtgccttgg
tgtttcaagc ccctgcagga agcagaatgc accttctgag aattc-3'

Subcloning of pITF$_{22-80}$ into pPICGIco (SEQ ID NO: 112)

5'-ctcgagaaaaga gccggggagt atgtgggcct gtcggcgaac cagtgtgccg tccctgccaa ggacagggtg gactgcggct accccaggt caccccgag cagtgcaaca accggggctg ctgcttcgac tccagcatcc ccggggtgcc ctggtgcttc aagcccctgc aggaaacaga atgcaccttc tgagaattc-3'

Subcloning of dITF$_{22-80}$ into pPICGIco (SEQ ID NO: 113)

5'-ctcgagaaaagagtgg cttaccaggg cctggcgacg aacctgtgcg
aggtgccgcc caaggacagg gtggactgcg gctaccctga gatcacctcc
gagcagtgcg tcaatcgggg ctgctgcttc gactccagca tccacggggt
gccctggtgc ttcaagccgt tgcaggacac agaatgcaga ttttgagaattc-3'

Subcloning of rITF$_{23-81}$ into pPICGIco (SEQ ID NO: 114)

5'-ctcgagaaaagacaggaat tgttggcct atctccaagc caatgtatgg
ctccaacaaa tgtcagggtg gactgtaact accccactgt cacatcagag
cagtgtaaca accgtggttg ctgttttgac tccagcatcc caaatgtgcc
ctggtgcttc aaacctctgc aagagacaga atgtacattt tgagaattc-3'

Subcloning of mITF$_{23-81}$ into pPICGIco (SEQ ID NO: 115)

5'-ctcgagaaaag agcagattac gttggcctgt ctccaagcca atgtatggtg
ccggcaaatg tcagagtgga ctgtggctac ccctctgtca catcggagca
gtgtaacaac cgtggctgct gctttgactc cagtatccca aatgtgccct
ggtgcttcaa acctctgcag gagacagaat gcacattttg agaattc-3'

FIGURE 17A

Amino acid sequence of MFα-hITF$_{15-73}$ (SEQ ID NO: 306)

MRFPSIFTAVLFAASSALAAPVNTTTEDETAQIPAEAVIGYSDLEGDFDVAVLPFSNST
NNGLLFINTTILSIAAKEEGVS<u>LEKR</u>EEYVGLSANQCAVPAKDRVDCGYPHVTPKECNN
RGCCFDSRIPGVPWCFKPLQEAECTF

FIGURE 17B

Amino acid sequence of MFα-pITF$_{22-80}$ (SEQ ID NO: 307)

MRFPSIFTAVLFAASSALAAPVNTTTEDETAQIPAEAVIGYSDLEGDFDVAVLPFSNST
NNGLLFINTTILSIAAKEEGVS<u>LEKR</u>GEYVGLSANQCAVPARDRVDCGYPQVTPEQCNN
RGCCFDSSIPGVPWCFKPLQETECTF

FIGURE 17C

Amino acid sequence of MFα-dITF$_{22-80}$ (SEQ ID NO: 308)

MRFPSIFTAVLFAASSALAAPVNTTTEDETAQIPAEAVIGYSDLEGDFDVAVLPFSNST
NNGLLFINTTILSIAAKEEGVS<u>LEKR</u>VAYQGLATNLCEVPPKDRVDCGYPEITSEQCVN
RGCCFDSSIHGVPWCFKPLQDTECRF

FIGURE 17D

Amino acid sequence of MFα-rITF$_{23-81}$ (SEQ ID NO: 309)

MRFPSIFTAVLFAASSALAAPVNTTTEDETAQIPAEAVIGYSDLEGDFDVAVLPFSNST
NNGLLFINTTILSIAAKEEGVS<u>LEKR</u>QEFVGLSPSQCMAPTNVRVDCNYPTVTSEQCNN
RGCCFDSSIPNVPWCFKPLQETECTF

FIGURE 17E

Amino acid sequence of MFα-mITF$_{23-81}$ (SEQ ID NO: 310)

MRFPSIFTAVLFAASSALAAPVNTTTEDETAQIPAEAVIGYSDLEGDFDVAVLPFSNST
NNGLLFINTTILSIAAKEEGVS<u>LEKR</u>ADYVGLSPSQCMVPANVRVDCGYPSVTSEQCNN
RGCCFDSSIPNVPWCFKPLQETECTF

Subcloning of full-length human ITF into pPICGIco (SEQ ID NO: 116)

5'-ctcgagaaaaga atg ctggggctgg tcctggcctt gctgtcctcc
agctctgctg aggagtacgt gggcctgtct gcaaaccagt gtgccgtgcc
agccaaggac agggtggact gcggctaccc ccatgtcacc cccaaggagt
gcaacaaccg gggctgctgc tttgactcca ggatccctgg agtgccttgg
tgtttcaagc ccctgcagga agcagaatgc accttctgag aattc-3'

FIGURE 18B

Subcloning of full-length pig ITF into pPICGIco (SEQ ID NO: 117)

5'-ctcgagaaaaga atggaggcca ggatgttctg gctgctagtg gtgctcctgg
ccttggcgtc ctccagctct gccggggagt atgtgggcct gtcggcgaac
Cagtgtgccg tccctgccaa ggacagggtg gactgcggct accccaggt
Caccccgag cagtgcaaca accggggctg ctgcttcgac tccagcatcc
Ccggggtgcc ctggtgcttc aagcccctgc aggaaacaga atgcaccttc
tgagaattc-3'

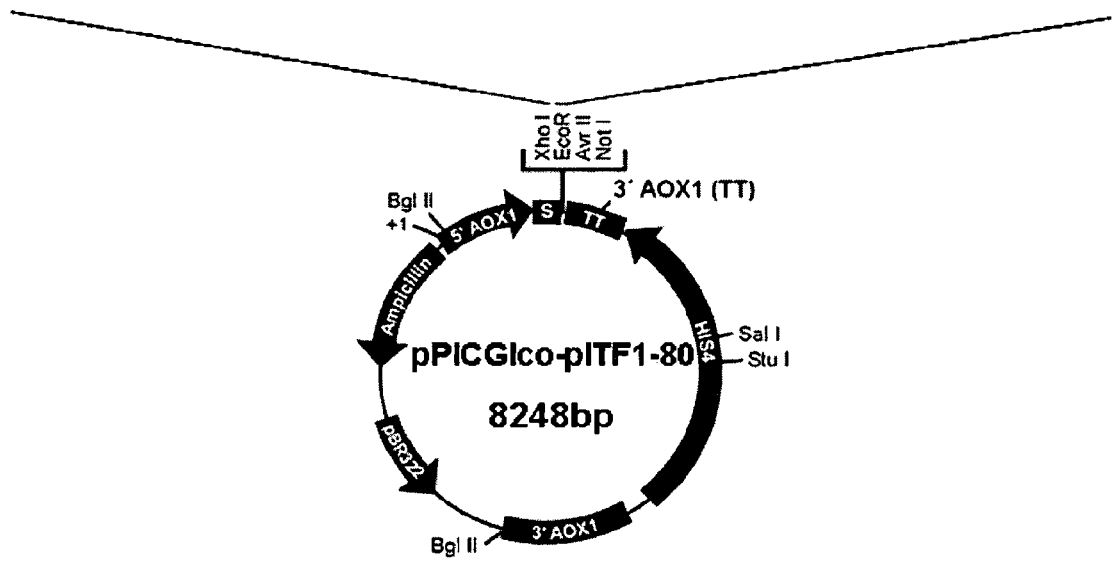

FIGURE 18C

Subcloning of full-length dog ITF into pPICGIco (SEQ ID NO: 118)

5'-ctcgagaaaa gaatggagg ccagagtgct ctggctgctg gtggtggtcc
tggtcctggg gtcctccagc ttggcagtgg cttaccaggg cctggcgacg
Aacctgtgcg aggtgccgcc caaggacagg gtggactgcg gctaccctga
Gatcacctcc gagcagtgcg tcaatcgggg ctgctgcttc gactccagca
Tccacggggt gccctggtgc ttcaagccgt tgcaggacac agaatgcaga
ttttgagaattc-3'

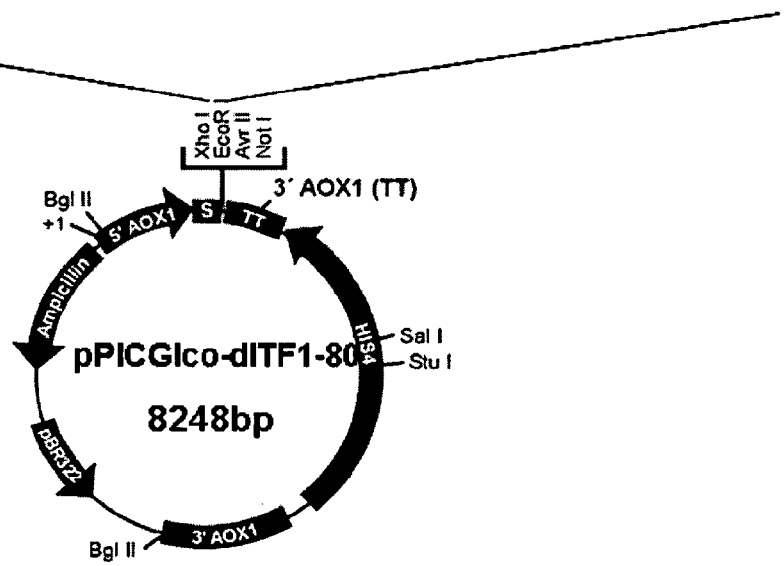

FIGURE 18D

Subcloning of full-length rat ITF into pPICGIco (SEQ ID NO: 119)

5'-ctcgagaaaagaatg gagaccagag ccttctggac aaccctgctg ctggtcctgg
ttgctgggtc ctcctgcaaa gcccaggaat ttgttggcct atctccaagc caatgtatgg
ctccaacaaa tgtcagggtg gactgtaact accccactgt cacatcagag
cagtgtaaca accgtggttg ctgttttgac tccagcatcc caaatgtgcc
ctggtgcttc aaacctctgc aagagacaga atgtacattt tgagaattc-3'

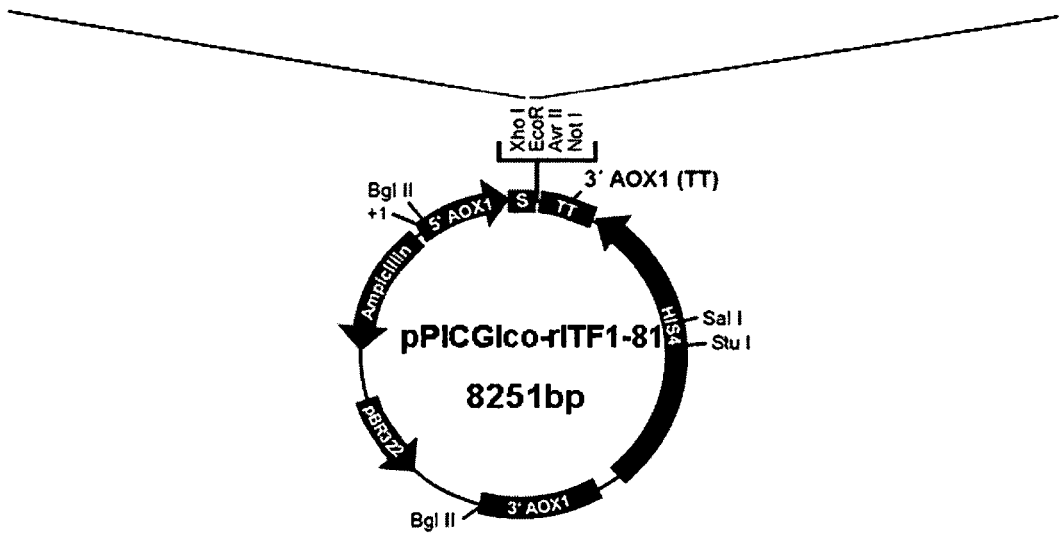

FIGURE 18E

Subcloning of full-length mouse ITF into pPICGIco (SEQ ID NO: 120)

5'-ctcgagaaaag aatgga gaccagagcc ctctggctaa tgctgttggt
ggtcctggtt gctgggtcct ctgggatagc tgcagattac gttggcctgt
ctccaagcca atgtatggtg ccggcaaatg tcagagtgga ctgtggctac
ccctctgtca catcggagca gtgtaacaac cgtggctgct gctttgactc
cagtatccca aatgtgccct ggtgcttcaa acctctgcag gagacagaat
gcacattttg agaattc-3'

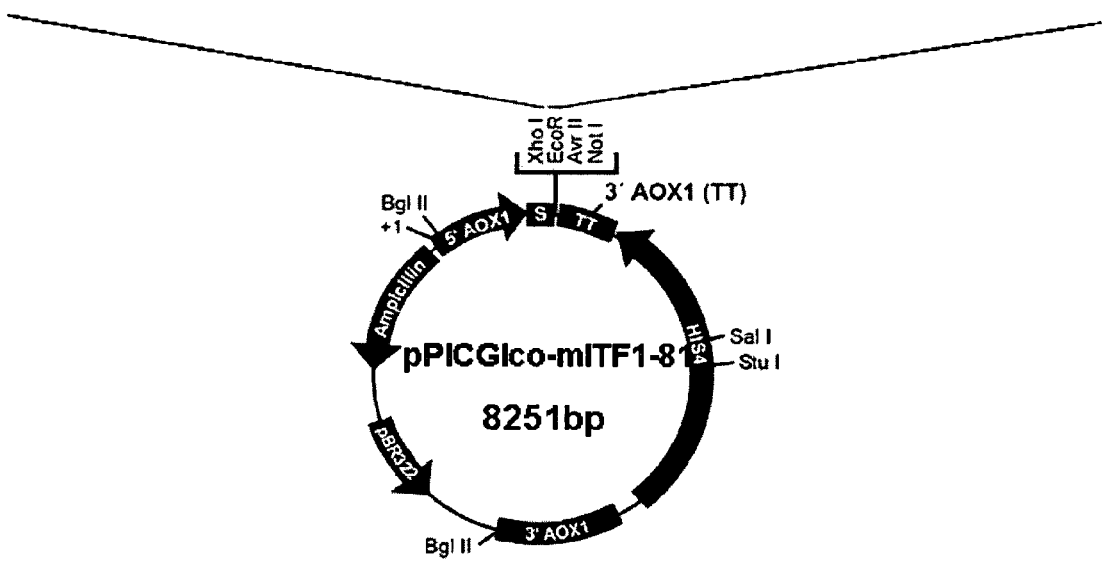

FIGURE 19A

Amino acid sequence of MFα-hITF$_{1-73}$ (SEQ ID NO: 311)

MRFPSIFTAVLFAASSALAAPVNTTTEDETAQIPAEAVIGYSDLEGDFDVAVLPFSNST
NNGLLFINTTILSIAAKEEGVS<u>LEKR</u>MLGLVLALLSSSSAEEYVGLSANQCAVPAKDRV
DCGYPHVTPKECNNRGCCFDSRIPGVPWCFKPLQEAECTF

FIGURE 19B

Amino acid sequence of MFα-pITF$_{1-80}$ (SEQ ID NO: 312)

MRFPSIFTAVLFAASSALAAPVNTTTEDETAQIPAEAVIGYSDLEGDFDVAVLPFSNST
NNGLLFINTTILSIAAKEEGVS<u>LEKR</u>MEARMFWLLVVLLALASSSSAGEYVGLSANQCA
VPARDRVDCGYPQVTPEQCNNRGCCFDSSIPGVPWCFKPLQETECTF

FIGURE 19C

Amino acid sequence of MFα-dITF$_{1-80}$ (SEQ ID NO: 313)

MRFPSIFTAVLFAASSALAAPVNTTTEDETAQIPAEAVIGYSDLEGDFDVAVLPFSNST
NNGLLFINTTILSIAAKEEGVS<u>LEKR</u>MEARVLWLLVVVLVLGSSSLAVAYQGLATNLCE
VPPKDRVDCGYPEITSEQCVNRGCCFDSSIHGVPWCFKPLQDTECRF

FIGURE 19D

Amino acid sequence of MFα-rITF$_{1-81}$ (SEQ ID NO: 314)

MRFPSIFTAVLFAASSALAAPVNTTTEDETAQIPAEAVIGYSDLEGDFDVAVLPFSNST
NNGLLFINTTILSIAAKEEGVSLEKR**METRAFWTTLLLVLVAGSSCKAQEFVGLSPSQC
MAPTNVRVDCNYPTVTSEQCNNRGCCFDSSIPNVPWCFKPLQETECTF**

FIGURE 19E

Amino acid sequence of MFα-mITF$_{1-81}$ (SEQ ID NO: 315)

MRFPSIFTAVLFAASSALAAPVNTTTEDETAQIPAEAVIGYSDLEGDFDVAVLPFSNST
NNGLLFINTTILSIAAKEEGVSLEKR**METRALWLMLLVVLVAGSSGIAADYVGLSPSQC
MVPANVRVDCGYPSVTSEQCNNRGCCFDSSIPNVPWCFKPLQETECTF**

Subcloning of hITF$_{15-73}$ into pPICpre (SEQ ID NO: 121)

5'-ctcgagaaaagag aggagtacgt gggcctgtct gcaaaccagt gtgccgtgcc
agccaaggac agggtggact gcggctaccc ccatgtcacc cccaaggagt
gcaacaaccg gggctgctgc tttgactcca ggatccctgg agtgccttgg
tgtttcaagc ccctgcagga agcagaatgc accttctgag aattc-3'

Subcloning of pITF$_{22-80}$ into pPICpre (SEQ ID NO: 122)

5'-ctcgagaaaaga gccggggagt atgtgggcct gtcggcgaac cagtgtgccg
tccctgccaa ggacagggtg gactgcggct accccaggt caccccgag
cagtgcaaca accggggctg ctgcttcgac tccagcatcc ccggggtgcc
ctggtgcttc aagcccctgc aggaaacaga atgcaccttc tgagaattc-3'

Subcloning of dITF$_{22-80}$ into pPICpre (SEQ ID NO: 123)

5'-ctcgagaaaagagtgg cttaccaggg cctggcgacg aacctgtgcg
aggtgccgcc caaggacagg gtggactgcg gctaccctga gatcacctcc
gagcagtgcg tcaatcgggg ctgctgcttc gactccagca tccacggggt
gccctggtgc ttcaagccgt tgcaggacac agaatgcaga ttttgagaattc-3'

Subcloning of rITF$_{23-81}$ into pPICpre (SEQ ID NO: 124)

5'-ctcgagaaaagacaggaat tgttggcct atctccaagc caatgtatgg
ctccaacaaa tgtcagggtg gactgtaact accccactgt cacatcagag
cagtgtaaca accgtggttg ctgttttgac tccagcatcc caaatgtgcc
ctggtgcttc aaacctctgc aagagacaga atgtacattt tgagaattc-3'

Subcloning of mITF$_{23-81}$ into pPICpre (SEQ ID NO: 125)

5'-ctcgagaaaag agcagattac gttggcctgt ctccaagcca atgtatggtg
ccggcaaatg tcagagtgga ctgtggctac ccctctgtca catcggagca
gtgtaacaac cgtggctgct gctttgactc cagtatccca aatgtgccct
ggtgcttcaa acctctgcag gagacagaat gcacattttg agaattc-3'

FIGURE 21A

Amino acid sequence of MFαpre-hITF$_{15-73}$ (SEQ ID NO: 316)

MRFPSIFTAVLFAASSALAALEKREEYVGLSANQCAVPAKDRVDCGYPHVTPKECNNRG
CCFDSRIPGVPWCFKPLQEAECTF

FIGURE 21B

Amino acid sequence of MFαpre-pITF$_{22-80}$ (SEQ ID NO: 317)

MRFPSIFTAVLFAASSALAALEKRGEYVGLSANQCAVPARDRVDCGYPQVTPEQCNNRG
CCFDSSIPGVPWCFKPLQETECTF

FIGURE 21C

Amino acid sequence of MFαpre-dITF$_{22-80}$ (SEQ ID NO: 318)

MRFPSIFTAVLFAASSALAALEKRVAYQGLATNLCEVPPKDRVDCGYPEITSEQCVNRG
CCFDSSIHGVPWCFKPLQDTECRF

FIGURE 21D

Amino acid sequence of MFαpre-rITF$_{23-81}$ (SEQ ID NO: 319)

MRFPSIFTAVLFAASSALAALEKRQEFVGLSPSQCMAPTNVRVDCNYPTVTSEQCNNRG
CCFDSSIPNVPWCFKPLQETECTF

FIGURE 21E

Amino acid sequence of MFαpre-mITF$_{23-81}$ (SEQ ID NO: 320)

MRFPSIFTAVLFAASSALAALEKRADYVGLSPSQCMVPANVRVDCGYPSVTSEQCNNRG
CCFDSSIPNVPWCFKPLQETECTF

SDS-PAGE of pPICpre-hITF$_{15-73}$ transformants

FIGURES 23A-B
SDS-PAGE and Western blot of pPICGIco-hITF$_{15-73}$ transformants
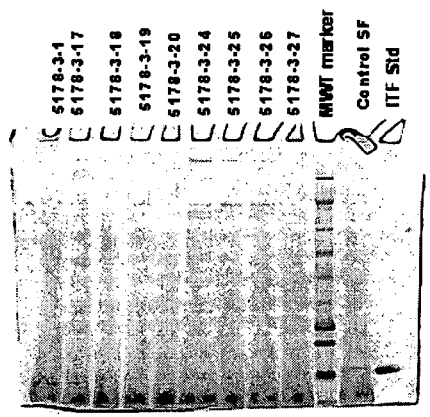
SDS PAGE - Reducing
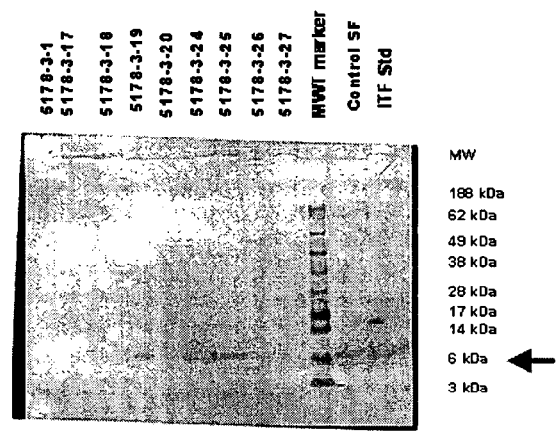
Western Blot Reducing
Note: All samples 120 hours post induction

FIGURES 24A-B
SDS-PAGE and Western blot of pPICGIco-hITF$_{15-73}$ transformant 3-24
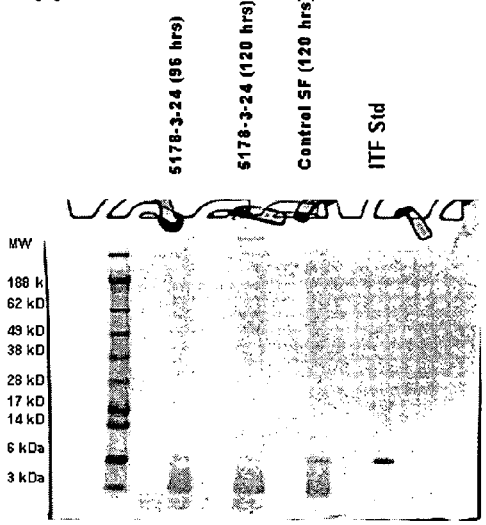
SDS PAGE - Reducing
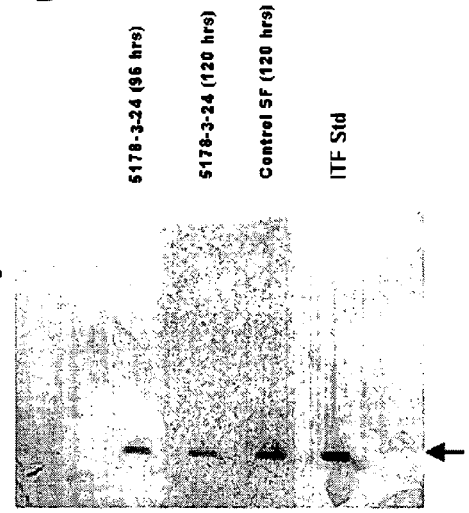
Western Blot Reducing

YEAST EXPRESSION VECTORS FOR PRODUCTION OF ITF

CROSS-REFERENCE TO RELATED APPLICATIONS

This application claims the benefit of U.S. Provisional Application No. 60/702,583, filed Jul. 25, 2005, which is hereby incorporated by reference.

BACKGROUND OF THE INVENTION

Intestinal trefoil factor ("ITF") expression vectors and methods of overexpressing ITF have been described (see, for example, Thim et al., Biochemistry, 34:4757-4764, 1995, and Kanai et al., Proc. Natl. Acad. Sci. USA, 95:178-182, 1998). One useful expression system involves the use of the yeast *Pichia pastoris*, which allows overexpression and secretion of heterologous genes at high levels (see, for example, Tschopp et al., Bio/Technology, 5:1305-1308, 1987, and Cregg et al., Bio/Technology, 11:905-910, 1993).

A need exists in the art for new methods of producing ITF in quantity, especially without extraneous amino acid sequences (FIGS. 1-2). The present invention provides such vectors and methods.

SUMMARY OF THE INVENTION

In one aspect, the invention features an expression vector including a nucleic acid encoding a biologically active intestinal trefoil factor (ITF) polypeptide. This expression vector encodes a polypeptide that includes an N-terminal fusion sequence, a protease cleavage site, and the ITF polypeptide, such that the cleavage site is contiguous with the ITF polypeptide and is recognized by a protease that cleaves immediately C-terminal to the cleavage site. In particular embodiments, the N-terminal fusion sequence includes an MFα signal sequence or an MFα presequence.

In particular embodiments, the cleavage site is recognized by the protease KEX2. Desirably, the cleavage site includes a polypeptide having the sequence of SEQ ID NO: 401.

In particular embodiments, the cleavage site is recognized by yeast aspartic protease (Yap3), Type IV dipeptidyl aminopeptidase (DPAP), yeast glycosyl-phosphatidylinositol-linked aspartyl protease (Mkc 7), pepsin, trypsin, chymotrypsin, or subtilisin.

In particular embodiments, the ITF polypeptide used in the vector of the invention is $hITF_{15-73}$. Desirably, the vector includes a nucleic acid having the sequence of SEQ ID NO: 111. Desirably, the vector includes a nucleic acid having the sequence of SEQ ID NO: 3.

In particular embodiments, the ITF polypeptide used in the vector of the invention is $hITF_{1-73}$. Desirably, the vector includes a nucleic acid having the sequence of SEQ ID NO: 116. Desirably, the vector includes a nucleic acid having the sequence of SEQ ID NO: 4.

In particular embodiments, the ITF polypeptide used in the vector of the invention is $hITF_{21-62}$, $hITF_{21-70}$, $hITF_{21-72}$, $hITF_{21-73}$, $hITF_{22-62}$, $hITF_{22-70}$, $hITF_{22-72}$, $hITF_{22-73}$, $hITF_{25-62}$, $hITF_{25-70}$, $hITF_{25-72}$, or $hITF_{25-73}$.

In particular embodiments, the ITF polypeptide used in the vector of the invention is $pITF_{22-80}$ or $pITF_{1-80}$. Desirably, the vector includes a nucleic acid having the sequence of SEQ ID NO: 112 or SEQ ID NO: 117.

In particular embodiments, the ITF polypeptide used in the vector of the invention is $dITF_{22-80}$ or $dITF_{1-80}$. Desirably, the vector includes a nucleic acid having the sequence of SEQ ID NO: 113 or SEQ ID NO: 118.

In particular embodiments, the ITF polypeptide used in the vector of the invention is $rITF_{23-81}$ or $rITF_{1-81}$. Desirably, the vector includes a nucleic acid having the sequence of SEQ ID NO: 114 or SEQ ID NO: 119.

In particular embodiments, the ITF polypeptide used in the vector of the invention is $mITF_{23-81}$ or $mITF_{1-81}$. Desirably, the vector includes a nucleic acid having the sequence of SEQ ID NO: 115 or SEQ ID NO: 120.

In a second aspect, the invention features an expression vector that includes a nucleic acid having at least 90% sequence identity to nucleotides 1 to 1,191 of SEQ ID NO: 2, a nucleic acid encoding a biologically active ITF polypeptide, and a nucleic acid having at least 90% sequence identity to nucleotides 1,218 to 8,001 of SEQ ID NO: 2.

In a third aspect, the invention features an expression vector that includes a nucleic acid having at least 90% sequence identity to nucleotides 1 to 1,008 of SEQ ID NO: 5, a nucleic acid encoding a biologically active ITF polypeptide, and a nucleic acid having at least 90% sequence identity to nucleotides 1,035 to 7,818 of SEQ ID NO: 5.

In a fourth aspect, the invention features a cell transformed with the vector of any of the previous aspects.

In a fifth aspect, the invention features a composition that includes a cell transformed with the vector of any of the previous aspects and a cell culture medium. In particular embodiments of the above aspect, the cell is *Pichia pastoris*. Desirably, the cell is a (Mut+) GS115 strain or a (his4-) GS115 strain.

In a sixth aspect, the invention features a method of culturing a cell of the fourth aspect so as to express the encoded ITF polypeptide and recover this polypeptide from the culture medium. In particular embodiments of the above aspect, the ITF polypeptide is secreted from the cell. Desirably, the expressed polypeptide is proteolytically processed in vivo prior to secretion from said cell, resulting in secretion of the ITF polypeptide substantially free of extraneous residues. Alternatively, the secreted polypeptide is contacted with a purified proteolytic enzyme in a reaction chamber, thereby producing the ITF polypeptide substantially free of extraneous residues.

In a seventh aspect, the invention features a method of culturing a cell of the fourth aspect so as to express the encoded ITF polypeptide and recover this polypeptide from the culture medium. In particular embodiments of the above aspect, the ITF polypeptide is secreted from the cell. Desirably, the expressed polypeptide is proteolytically processed in vivo prior to secretion from said cell. Alternatively, the secreted polypeptide is contacted with a purified proteolytic enzyme in a reaction chamber.

In an eighth aspect, the invention features a method for producing a biologically active ITF polypeptide. This method includes the step of culturing yeast transformants containing recombinant plasmids encoding a polypeptide that includes a ITF polypeptide, such that the yeast produce and secrete the ITF polypeptide unaccompanied by an extraneous EA amino acid sequence. The method also includes steps of isolating and purifying the ITF polypeptide. In particular embodiments, the ITF polypeptide is $hITF_{15-73}$, $hITF_{1-73}$, $hITF_{21-62}$, $hITF_{21-70}$, $hITF_{21-72}$, $hITF_{21-73}$, $hITF_{22-62}$, $hITF_{22-70}$, $hITF_{22-72}$, $hITF_{22-73}$, $hITF_{25-62}$, $hITF_{25-70}$, $hITF_{25-72}$, $hITF_{25-73}$, $pITF_{1-80}$, $pITF_{22-80}$, $dITF_{1-80}$, $dITF_{22-80}$, $rITF_{1-81}$, $rITF_{23-81}$, $mITF_{1-81}$, or $mITF_{22-81}$.

In a ninth aspect, the invention features a polypeptide that includes an N-terminal fusion sequence, a protease cleavage site, and the ITF polypeptide, such that the cleavage site is contiguous with the ITF polypeptide and is recognized by a protease that cleaves immediately C-terminal to the cleavage site. In particular embodiments, the sequence of the polypeptide comprises SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, or SEQ ID NO: 320.

In a tenth aspect, the invention features an expression vector that includes a nucleic acid having the sequence of SEQ ID NO: 2.

In an eleventh aspect, the invention features an expression vector that includes a nucleic acid having the sequence of SEQ ID NO: 5.

By "intestinal trefoil factor" ("ITF") is meant any protein that is substantially homologous to human ITF (FIG. 14A) and that is expressed in the large intestine, small intestine, or colon to a greater extent than it is expressed in tissues other than the small intestine, large intestine, or colon. Also included are: allelic variations; natural mutants; induced mutants; proteins encoded by DNA that hybridizes under high or low stringency conditions to ITF encoding nucleic acids retrieved from naturally occurring material; and polypeptides or proteins retrieved by antisera to ITF, especially by antisera to the active site or binding domain of ITF. The term also includes other chimeric polypeptides that include an ITF.

In addition to substantially full-length polypeptides, the term ITF, as used herein, includes biologically active fragments of the polypeptides. As used herein, the term "fragment," which applies to a polypeptide unless otherwise indicated, will ordinarily be at least 10 contiguous amino acids, typically at least 20 contiguous amino acids, more typically at least 30 contiguous amino acids, usually at least 40 contiguous amino acids, preferably at least 50 contiguous amino acids, and most preferably 59 or more contiguous amino acids in length. Fragments of ITF can be generated by methods known to those skilled in the art and described herein. The ability of a candidate fragment to exhibit a biological activity of ITF can be assessed by methods known to those skilled in the art and are described herein. Also included in the term "fragment" are biologically active ITF polypeptides containing amino acids that are normally removed during protein processing, including additional amino acids that are not required for the biological activity of the polypeptide, or including additional amino acids that result from alternative mRNA splicing or alternative protein processing events.

An ITF polypeptide, fragment, or analog is biologically active if it exhibits a biological activity of a naturally occurring ITF, e.g., the ability to alter gastrointestinal motility in a mammal, the ability to restitute gastrointestinal, respiratory, or uterine epithelium, or the ability to enhance dermal or corneal epithelial wound healing.

Particularly useful ITF polypeptides that retain biological activity include the polypeptides corresponding to amino acid residues 1-73 of SEQ ID NO: 301 (full-length human ITF, also designated hITF$_{1-73}$), amino acid residues 15-73 of SEQ ID NO: 301 (hITF$_{15-73}$), amino acid residues 21-62 of SEQ ID NO: 301 (hITF$_{21-62}$), amino acid residues 21-70 of SEQ ID NO: 301 (hITF$_{21-70}$), amino acid residues 21-72 of SEQ ID NO: 301 (hITF$_{21-72}$), amino acid residues 21-73 of SEQ ID NO: 301 (hITF$_{21-73}$), amino acid residues 22-62 of SEQ ID NO: 301 (hITF$_{22-62}$), amino acid residues 22-70 of SEQ ID NO: 301 (hITF$_{22-70}$), amino acid residues 22-72 of SEQ ID NO: 301 (hITF$_{22-72}$), amino acid residues 22-73 of SEQ ID NO: 301 (hITF$_{22-73}$), amino acid residues 25-62 of SEQ ID NO: 301 (hITF$_{25-62}$), amino acid residues 25-70 of SEQ ID NO: 301 (hITF$_{25-70}$), amino acid residues 25-72 of SEQ ID NO: 301 (hITF$_{25-72}$), amino acid residues 25-73 of SEQ ID NO: 301 (hITF$_{25-73}$), amino acid residues 1-80 of SEQ ID NO: 302 (full-length pig ITF, also designated pITF$_{1-80}$), amino acid residues 22-80 of SEQ ID NO: 302 (pITF$_{22-80}$), amino acid residues 1-80 of SEQ ID NO: 303 (full-length dog ITF, also designated dITF$_{1-80}$), amino acid residues 22-80 of SEQ ID NO: 303 (dITF$_{22-80}$), amino acid residues 1-81 of SEQ ID NO: 304 (full-length rat ITF, also designated rITF$_{1-81}$), amino acid residues 23-81 of SEQ ID NO: 304 (rITF$_{23-81}$), amino acid residues 1-81 of SEQ ID NO: 305 (full-length mouse ITF, also designated mITF$_{1-81}$), and amino acid residues 23-81 of SEQ ID NO: 305 (mITF$_{23-81}$).

By "MFα prepropeptide sequence" or "MFα signal sequence" is meant the DNA sequence spanned by nucleotides 949 to 1,191 of SEQ ID NO: 2 or the protein sequence encoded therein.

By "MFα presequence" is meant the DNA sequence spanned by nucleotides 949 to 1,008 of SEQ ID NO: 5 or the protein sequence encoded therein.

By "modify," when applied to an expression vector, is meant to alter the sequence of such a vector by addition, deletion, or mutation of nucleotides. A modified vector will generally exhibit at least 70%, more preferably 80%, more preferably 90%, and most preferably 95% or even 99% sequence identity with the unmodified vector.

By "N-terminal fusion sequence" is meant an amino acid sequence fused to the N terminus of a protein of interest, or a nucleotide sequence encoding such an amino acid sequence. This could include the MFα signal sequence, the MFα presequence, or other signal or leader sequences. The term also encompasses fusion partners that enhance size, solubility, or other desirable characteristics of the expressed fusion protein.

By "polypeptide" or "peptide" or "protein" is meant any chain of at least two naturally-occurring amino acids, or unnatural amino acids (e.g., those amino acids that do not occur in nature) regardless of post-translational modification (e.g., glycosylation or phosphorylation), constituting all or part of a naturally-occurring or unnatural polypeptide or peptide, as is described herein.

Polypeptides or derivatives thereof may be fused or attached to another protein or peptide, for example, as an α-Factor signal sequence fusion polypeptide.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications. Conservative substitutions typically include substitutions within the following groups: glycine, alanine, valine, isoleucine, leucine; aspartic acid, glutamic acid, asparagine, glutamine; serine, threonine; lysine, arginine; and phenylalanine, tyrosine.

By "protease" or "proteolytic enzyme" is meant an enzyme that catalyzes the cleavage, or proteolysis, of proteins into smaller peptide fractions and amino acids. Some proteases recognize and bind to particular amino acid sequences and cleave specific peptide bonds within or outside the recognition sequence, while other proteases cleave nonspecifically.

By "protease cleavage site" or "protease recognition site" is meant an amino acid sequence to which a protease is capable of binding, thereby leading to proteolysis. Desirably, a protease will bind specifically to a corresponding recognition site.

By "vector" or "plasmid" is meant a DNA molecule into which fragments of DNA may be inserted or cloned. A vector will contain one or more unique restriction sites, and may be capable of autonomous replication in a defined host or vehicle organism such that the cloned sequence is reproducible.

By "expression vector" or "construct" is meant any autonomous element capable of replicating in a host independently of the host's chromosome, after additional sequences of DNA have been incorporated into the autonomous element's genome.

All nucleotide sequences presented herein should be understood to read from the 5' end to the 3' end unless otherwise indicated. Likewise, all amino acid sequences should be understood to read from the N-terminal end to the C-terminal end unless otherwise indicated.

BRIEF DESCRIPTION OF THE DRAWINGS

FIG. 4 is the nucleotide sequence of the yeast vector pPIC9 (SEQ ID NO: 1). The multiple cloning site is shown in bold.

FIG. 5 is the nucleotide sequence of the yeast vector pPICGIco (SEQ ID NO: 2). The modified multiple cloning site is shown in bold.

FIG. 6 is the nucleotide sequence of the yeast vector pPICGIco-$hITF_{15-73}$ (SEQ ID NO: 3), which encodes an $MF\alpha$-$hITF_{15-73}$ fusion polypeptide lacking a Glu-Ala sequence between the $MF\alpha$ signal sequence and the $hITF_{15-73}$ sequence. A KEX2 recognition and processing site, LEKR (SEQ ID NO: 401), directly precedes the $hITF_{15-73}$ sequence. The restriction endonuclease sites XhoI (CTCGAG) and EcoRI (GAATTC) used for subcloning are underlined. The sequence encoding $hITF_{15-73}$ is shown in bold.

FIG. 7 is the nucleotide sequence of the yeast vector pPICGIco-$hITF_{1-73}$ (SEQ ID NO: 4), which encodes an $MF\alpha$-$ITF_{1-73}$ fusion polypeptide lacking a Glu-Ala sequence between the $MF\alpha$ signal sequence and the $ITF_{1-73}$ sequence. A KEX2 recognition and processing site directly precedes the $hITF_{1-73}$ sequence.

The restriction endonuclease sites XhoI (CTCGAG) and EcoRI (GAATTC) used for subcloning are underlined. The sequence encoding $hITF_{1-73}$ is shown in bold.

FIG. 8 is the nucleotide sequence of the yeast vector pPICpre (SEQ ID NO: 5). The multiple cloning site is shown in bold.

FIG. 9 is the nucleotide sequence of the yeast vector pPICpre-$hITF_{15-73}$ (SEQ ID NO: 6), which encodes an $MF\alpha$pre-$ITF_{15-73}$ fusion polypeptide lacking a Glu-Ala sequence between the $MF\alpha$ presequence and the $ITF_{15-73}$ sequence. A KEX2 recognition and processing site directly precedes the $hITF_{15-73}$ sequence. The restriction endonuclease sites XhoI (CTCGAG) and EcoRI (GAATTC) used for subcloning are underlined. The sequence encoding $hITF_{15-73}$ is shown in bold.

FIG. 10 is the nucleotide sequence of the yeast vector pPICGIco-$hITF_{15-73}$ (SEQ ID NO: 7), which encodes an $MF\alpha$-$hITF_{15-73}$ fusion polypeptide containing a Glu-Ala sequence between the $MF\alpha$ signal sequence and the $hITF_{15-73}$ sequence. A KEX2 recognition and processing site directly precedes the $hITF_{15-73}$ sequence. The sequence encoding $hITF_{15-73}$ is shown in bold.

FIG. 11A shows vector maps of pPIC9 and pPICGIco and describes the construction of pPICGIco.

FIG. 11B shows the multiple cloning site of pPICGIco.

Figures 12A, 12B, 12C:
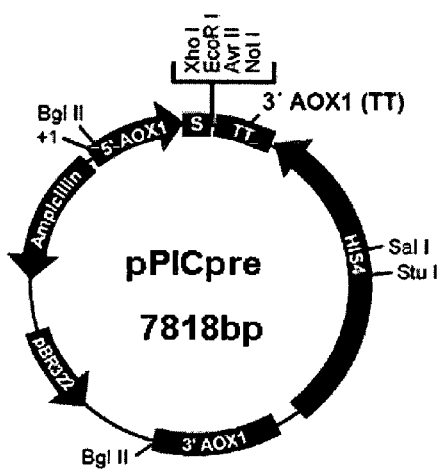

FIG. 12A is a vector map of pPICpre.

FIG. 12B is the nucleotide sequence of a PCR-amplified DNA region that is designed for insertion into pPICGIco linearized at BamH I and Xho I sites, resulting in pPICpre. The PCR-amplified region corresponds to SEQ ID NO: 131.

FIG. 12C shows the multiple cloning site of pPICpre.

FIG. 13A is the nucleotide sequence of the human ITF cDNA (Genbank Accession No: BC017859) (SEQ ID NO: 101). Primer sequences are underlined. The sequence encoding $hITF_{1-73}$ is shown in bold.

FIG. 13B is the nucleotide sequence of the pig ITF cDNA (Genbank Accession No: F14493) (SEQ ID NO: 102). Primer sequences are underlined. The sequence encoding $pITF_{1-80}$ is shown in bold.

FIG. 13C is the nucleotide sequence of the dog ITF cDNA (Genbank Accession No: NM_001002990) (SEQ ID NO: 103). Primer sequences are underlined. The sequence encoding $dITF_{1-80}$ is shown in bold.

FIG. 13D is the nucleotide sequence of the rat ITF cDNA (Genbank Accession No: NM_013042) (SEQ ID NO: 104). Primer sequences are underlined. The sequence encoding $rITF_{1-81}$ is shown in bold.

FIG. 13E is the nucleotide sequence of the mouse ITF cDNA (Genbank Accession No: NM_011575) (SEQ ID NO: 105). Primer sequences are underlined. The sequence encoding $mITF_{1-81}$ is shown in bold.

FIG. 14A is the amino acid sequence of full-length human ITF (SEQ ID NO: 301). Particular residues are indicated by superscripts.

FIG. 14B is the amino acid sequence of full-length pig ITF (SEQ ID NO: 302). Particular residues are indicated by superscripts.

FIG. 14C is the amino acid sequence of full-length dog ITF (SEQ ID NO: 303). Particular residues are indicated by superscripts.

FIG. 14D is the amino acid sequence of full-length rat ITF (SEQ ID NO: 304). Particular residues are indicated by superscripts.

FIG. 14E is the amino acid sequence of full-length mouse ITF (SEQ ID NO: 305). Particular residues are indicated by superscripts.

Figure 15A:
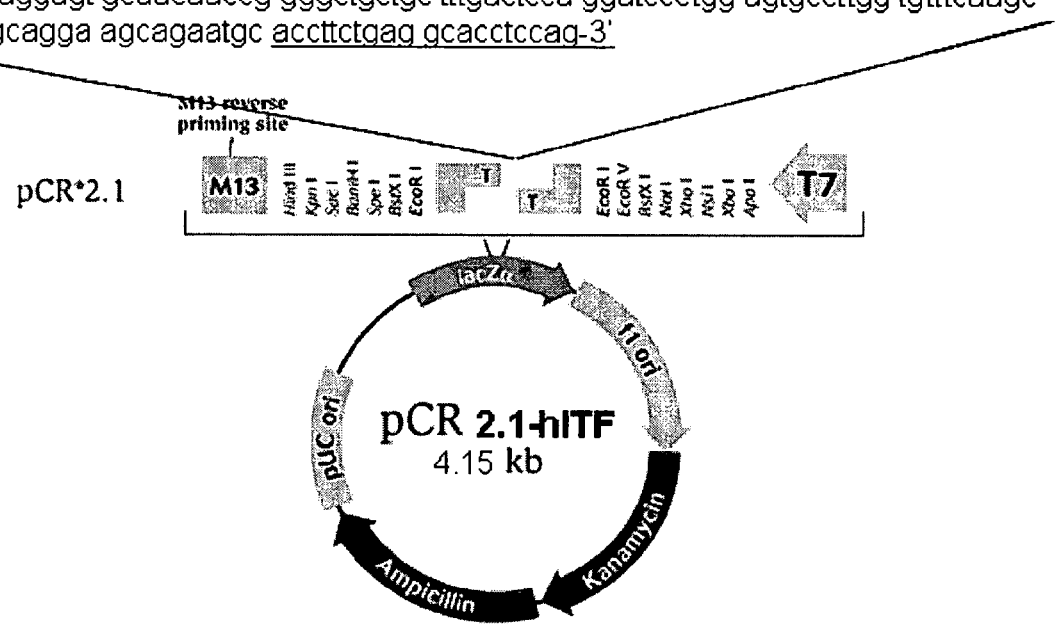

FIG. 15A shows the subcloning into pCR2.1 of a PCR-amplified DNA region that includes the nucleotide sequence encoding full-length human ITF, resulting in pCR2.1-hITF. The PCR-amplified region corresponds to SEQ ID NO: 106.

Figure 15B:
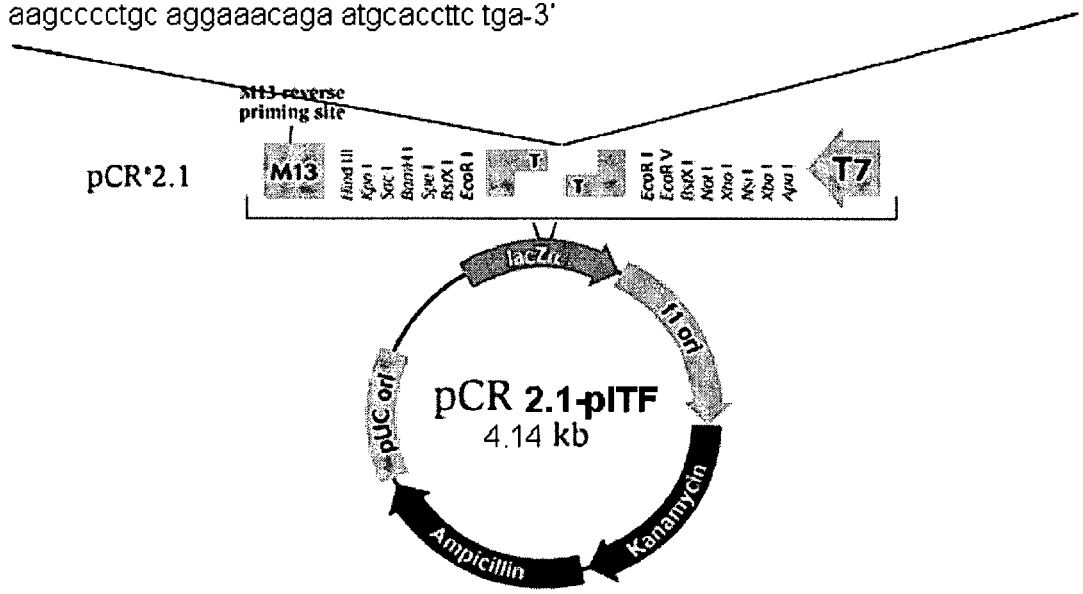

FIG. 15B shows the subcloning into pCR2.1 of a PCR-amplified DNA region that includes the nucleotide sequence encoding full-length pig ITF, resulting in pCR2.1-pITF. The PCR-amplified region corresponds to SEQ ID NO: 107.

FIG. 15C shows the subcloning into pCR2.1 of a PCR-amplified DNA region that includes the nucleotide sequence encoding full-length dog ITF, resulting in pCR2.1-dITF. The PCR-amplified region corresponds to SEQ ID NO: 108.

FIG. 15D shows the subcloning into pCR2.1 of a PCR-amplified DNA region that includes the nucleotide sequence encoding full-length human ITF, resulting in pCR2.1-rITF. The PCR-amplified region corresponds to SEQ ID NO: 109.

FIG. 15E shows the subcloning into pCR2.1 of a PCR-amplified DNA region that includes the nucleotide sequence encoding full-length mouse ITF, resulting in pCR2.1-mITF. The PCR-amplified region corresponds to SEQ ID NO: 110.

Figure 16A:
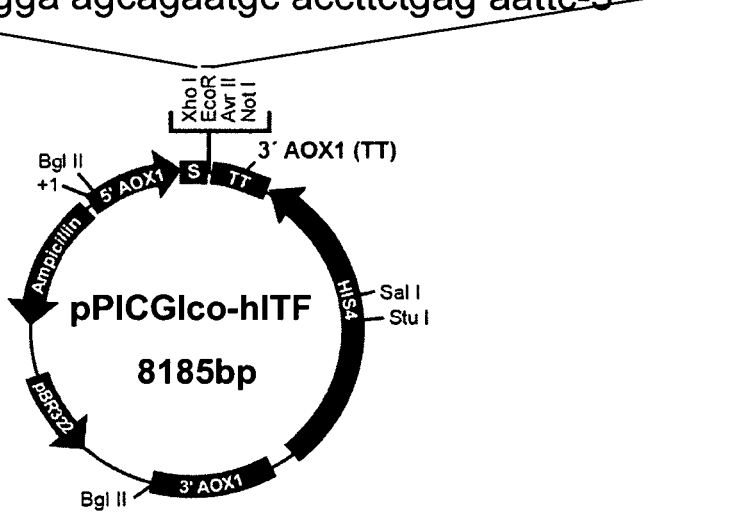

FIG. 16A shows the subcloning into pPICGIco of a PCR-amplified DNA region that includes the nucleotide sequence encoding $hITF_{15-73}$, resulting in pPICGIco-$hITF_{15-73}$ (also referred to as pPICGIco-hITF). The PCR-amplified region corresponds to SEQ ID NO: 111.

Figure 16B:
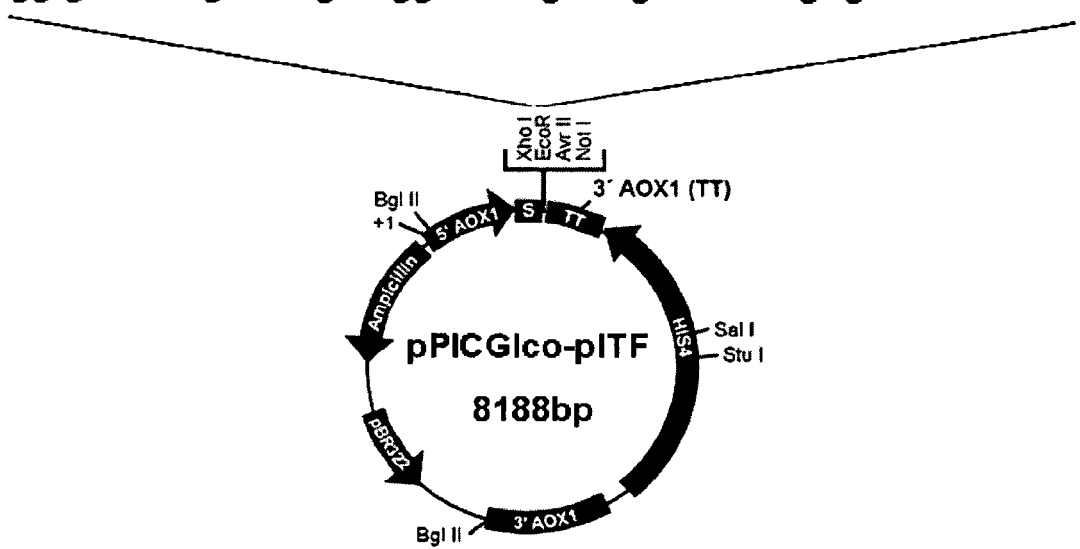

FIG. 16B shows the subcloning into pPICGIco of a PCR-amplified DNA region that includes the nucleotide sequence encoding pITF$_{22-80}$, resulting in pPICGIco-pITF$_{22-80}$ (also referred to as pPICGIco-pITF). The PCR-amplified region corresponds to SEQ ID NO: 112.

Figure 16C:
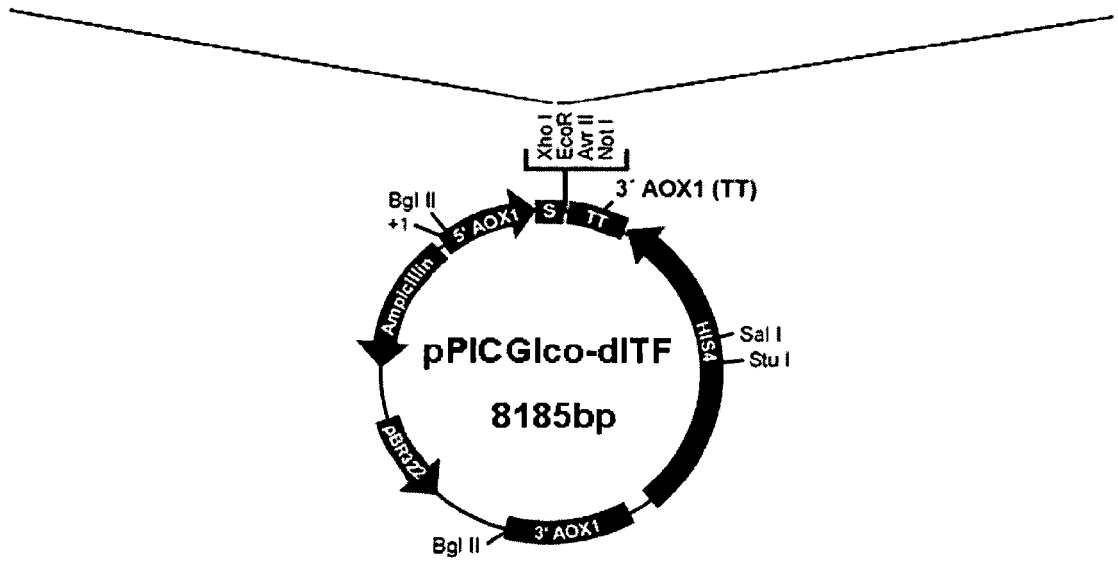

FIG. 16C shows the subcloning into pPICGIco of a PCR-amplified DNA region that includes the nucleotide sequence encoding dITF$_{22-80}$, resulting in pPICGIco-dITF$_{22-80}$ (also referred to as pPICGIco-dITF). The PCR-amplified region corresponds to SEQ ID NO: 113.

Figure 16D:
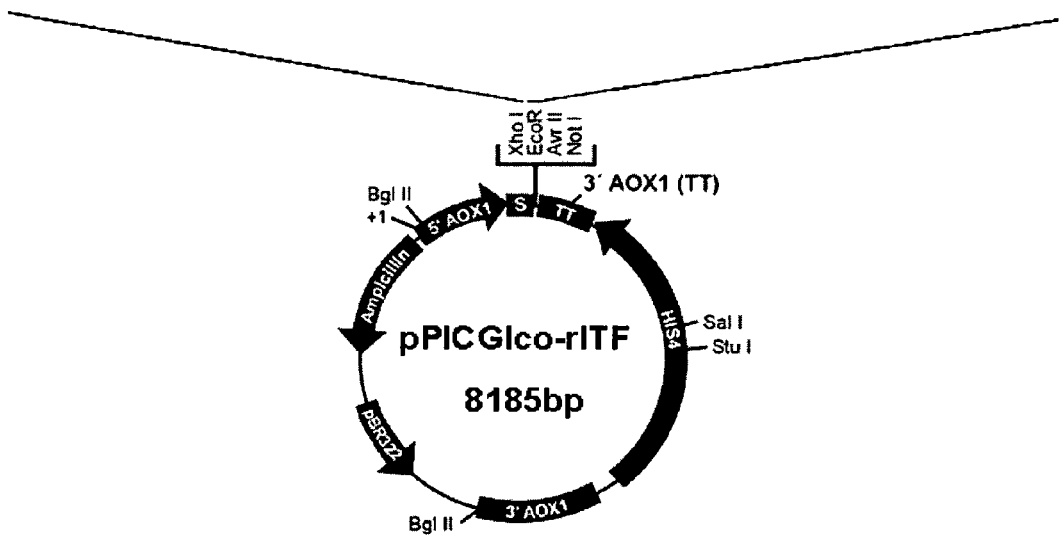

FIG. 16D shows the subcloning into pPICGIco of a PCR-amplified DNA region that includes the nucleotide sequence encoding rITF$_{23-81}$, resulting in pPICGIco-rITF$_{23-81}$ (also referred to as pPICGIco-rITF). The PCR-amplified region corresponds to SEQ ID NO: 114.

Figure 16E:
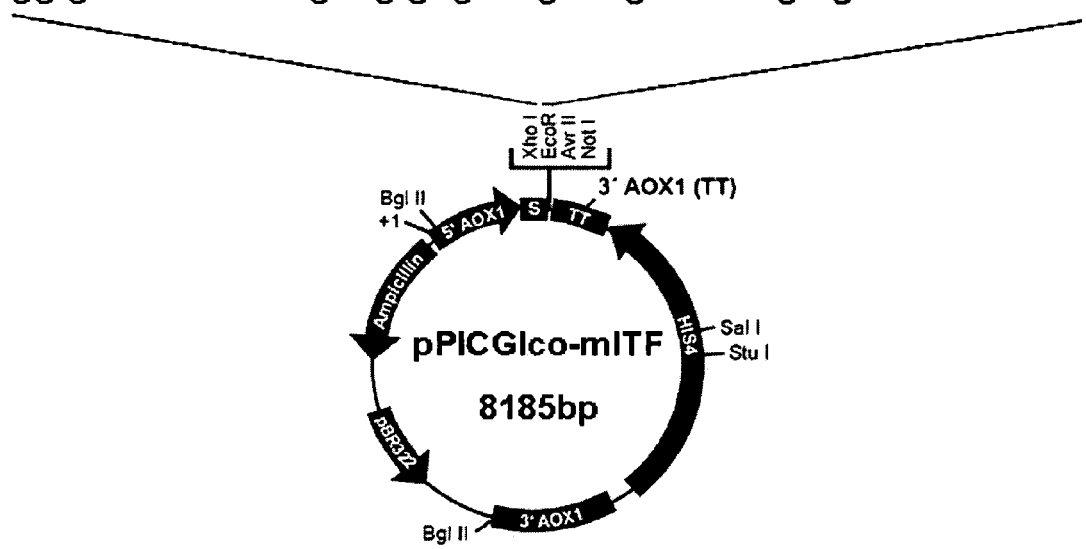

FIG. 16E shows the subcloning into pPICGIco of a PCR-amplified DNA region that includes the nucleotide sequence encoding mITF$_{23-81}$, resulting in pPICGIco-mITF$_{23-81}$ (also referred to as pPICGIco-mITF). The PCR-amplified region corresponds to SEQ ID NO: 115.

FIG. 17A is the amino acid sequence of the MFα signal sequence-hITF$_{15-73}$ fusion (also referred to as MFα-hITF$_{15-73}$) (SEQ ID NO: 306). The MFα signal sequence is shown in italics, the KEX2 proteolytic cleavage site is underlined, and hITF$_{15-73}$ is shown in bold.

FIG. 17B is the amino acid sequence of the MFα signal sequence-pITF$_{22-80}$ fusion (also referred to as MFα-pITF$_{22-80}$) (SEQ ID NO: 307). The MFα signal sequence is shown in italics, the KEX2 proteolytic cleavage site is underlined, and pITF$_{22-80}$ is shown in bold.

FIG. 17C is the amino acid sequence of the MFα signal sequence-dITF$_{22-80}$ fusion (also referred to as MFα-dITF$_{22-80}$) (SEQ ID NO: 308). The MFα signal sequence is shown in italics, the KEX2 proteolytic cleavage site is underlined, and dITF$_{22-80}$ is shown in bold.

FIG. 17D is the amino acid sequence of the MFα signal sequence-rITF$_{23-81}$ fusion (also referred to as MFα-rITF$_{23-81}$) (SEQ ID NO: 309). The MFα signal sequence is shown in italics, the KEX2 proteolytic cleavage site is underlined, and rITF$_{23-81}$ is shown in bold.

FIG. 17E is the amino acid sequence of the MFα signal sequence-mITF$_{23-81}$ fusion (also referred to as MFα-mITF$_{23-81}$) (SEQ ID NO: 310). The MFα signal sequence is shown in italics, the KEX2 proteolytic cleavage site is underlined, and mITF$_{23-81}$ is shown in bold.

Figure 18A:
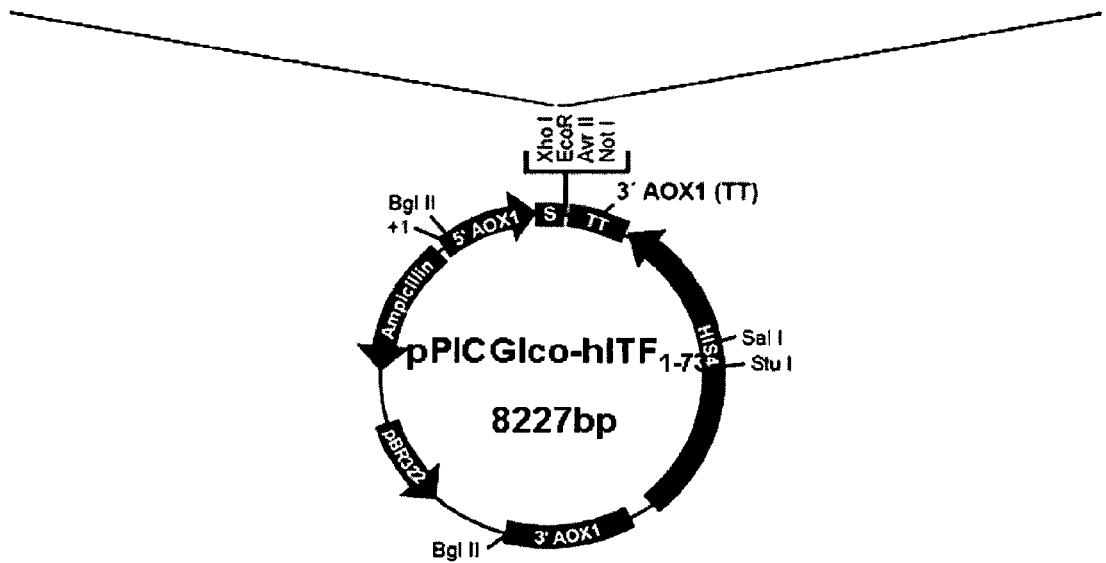

FIG. 18A shows the subcloning into pPICGIco of a PCR-amplified DNA region that includes the nucleotide sequence encoding hITF$_{1-73}$, resulting in pPICGIco-hITF$_{1-73}$. The PCR-amplified region corresponds to SEQ ID NO: 116.

FIG. 18B shows the subcloning into pPICGIco of a PCR-amplified DNA region that includes the nucleotide sequence encoding pITF$_{1-80}$, resulting in pPICGIco-pITF$_{1-80}$. The PCR-amplified region corresponds to SEQ ID NO: 117.

FIG. 18C shows the subcloning into pPICGIco of a PCR-amplified DNA region that includes the nucleotide sequence encoding dITF$_{1-80}$, resulting in pPICGIco-dITF$_{1-80}$. The PCR-amplified region corresponds to SEQ ID NO: 118.

FIG. 18D shows the subcloning into pPICGIco of a PCR-amplified DNA region that includes the nucleotide sequence encoding rITF$_{1-81}$, resulting in pPICGIco-rITF$_{1-81}$. The PCR-amplified region corresponds to SEQ ID NO: 119.

FIG. 18E shows the subcloning into pPICGIco of a PCR-amplified DNA region that includes the nucleotide sequence encoding mITF$_{1-81}$, resulting in pPICGIco-mITF$_{1-81}$. The PCR-amplified region corresponds to SEQ ID NO: 120.

FIG. 19A is the amino acid sequence of the MFα signal sequence-hITF$_{1-73}$ fusion (also referred to as MFα-hITF$_{1-73}$) (SEQ ID NO: 311). The MFα signal sequence is shown in italics, the KEX2 proteolytic cleavage site is underlined, and hITF$_{1-73}$ is shown in bold.

FIG. 19B is the amino acid sequence of the MFα signal sequence-pITF$_{1-80}$ fusion (also referred to as MFα-pITF$_{1-80}$) (SEQ ID NO: 312). The MFα signal sequence is shown in italics, the KEX2 proteolytic cleavage site is underlined, and pITF$_{1-80}$ is shown in bold.

FIG. 19C is the amino acid sequence of the MFα signal sequence-dITF$_{1-80}$ fusion (also referred to as MFα-dITF$_{1-80}$) (SEQ ID NO: 313). The MFα signal sequence is shown in italics, the KEX2 proteolytic cleavage site is underlined, and dITF$_{1-80}$ is shown in bold.

FIG. 19D is the amino acid sequence of the MFα signal sequence-rITF$_{1-81}$ fusion (also referred to as MFα-rITF$_{1-81}$) (SEQ ID NO: 314). The MFα signal sequence is shown in italics, the KEX2 proteolytic cleavage site is underlined, and rITF$_{1-81}$ is shown in bold.

FIG. 19E is the amino acid sequence of the MFα signal sequence-mITF$_{1-81}$ fusion (also referred to as MFα-mITF$_{1-81}$) (SEQ ID NO: 315). The MFα signal sequence is shown in italics, the KEX2 proteolytic cleavage site is underlined, and mITF$_{1-81}$ is shown in bold.

Figure 20A:
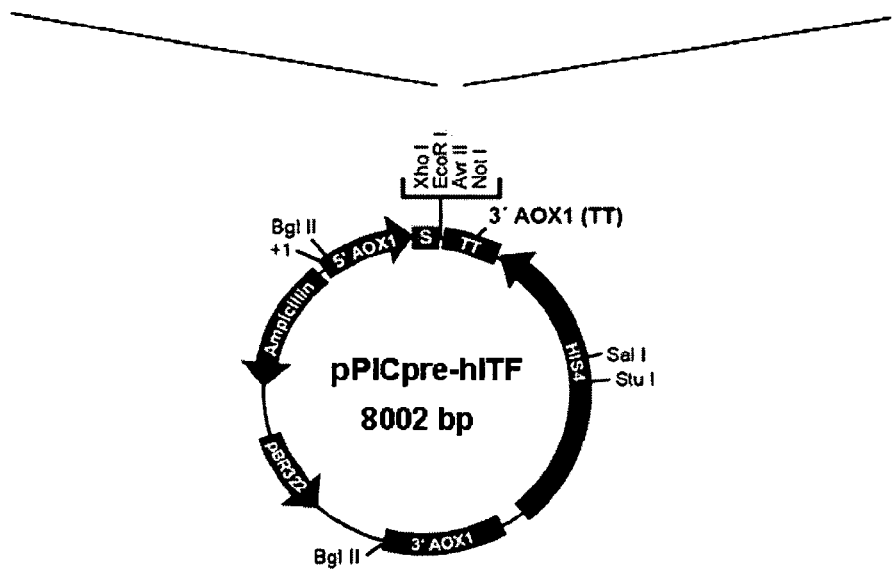

FIG. 20A shows the subcloning into pPICpre of a PCR-amplified DNA region that includes the nucleotide sequence encoding hITF$_{15-73}$, resulting in pPICpre-hITF$_{15-73}$ (also referred to as pPICpre-hITF). The PCR-amplified region corresponds to SEQ ID NO: 121.

Figure 20B:
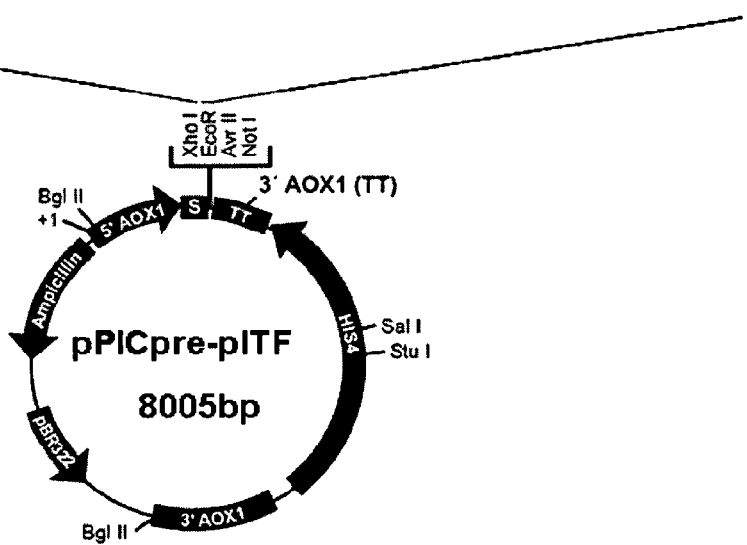

FIG. 20B shows the subcloning into pPICpre of a PCR-amplified DNA region that includes the nucleotide sequence encoding pITF$_{22-80}$, resulting in pPICpre-pITF$_{22-80}$ (also referred to as pPICpre-pITF). The PCR-amplified region corresponds to SEQ ID NO: 122.

Figure 20C:
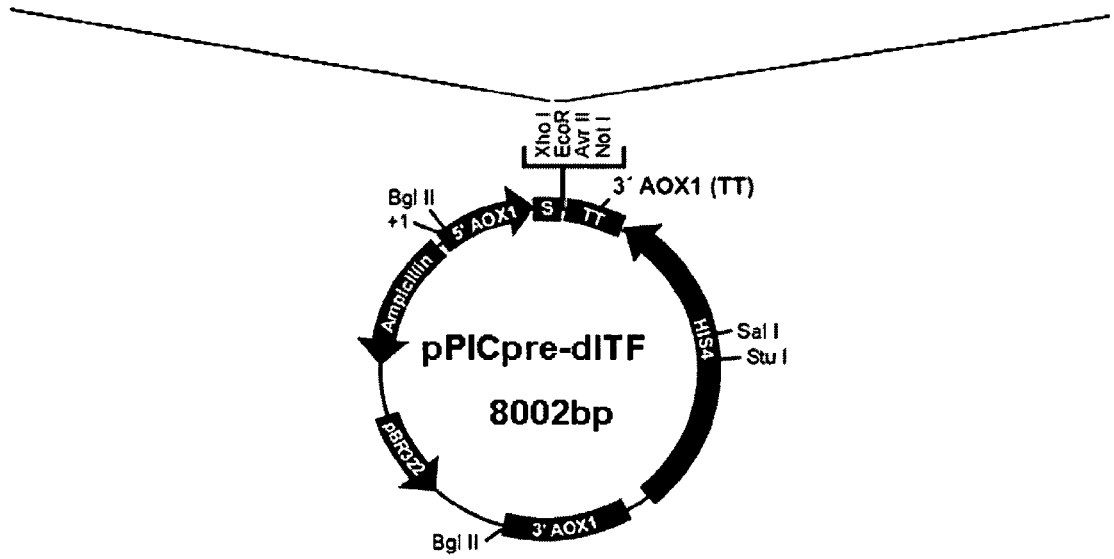

FIG. 20C shows the subcloning into pPICpre of a PCR-amplified DNA region that includes the nucleotide sequence encoding dITF$_{22-80}$, resulting in pPICpre-dITF$_{22-80}$ (also referred to as pPICpre-dITF). The PCR-amplified region corresponds to SEQ ID NO: 123.

Figure 20D:
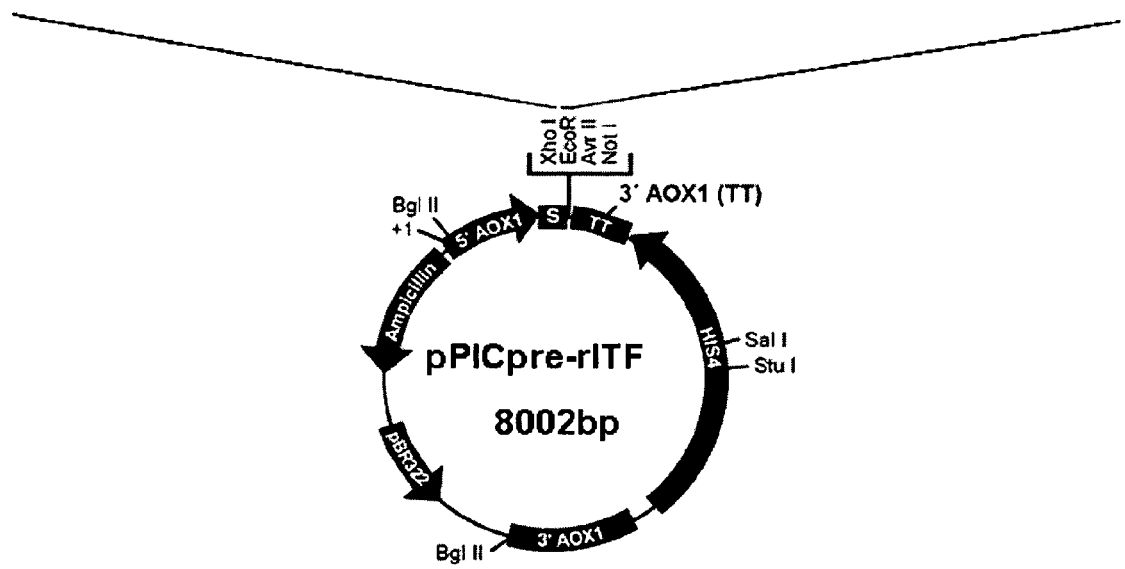

FIG. 20D shows the subcloning into pPICpre of a PCR-amplified DNA region that includes the nucleotide sequence encoding rITF$_{23-81}$, resulting in pPICpre-rITF$_{23-81}$ (also referred to as pPICpre-rITF). The PCR-amplified region corresponds to SEQ ID NO: 124.

Figure 20E:
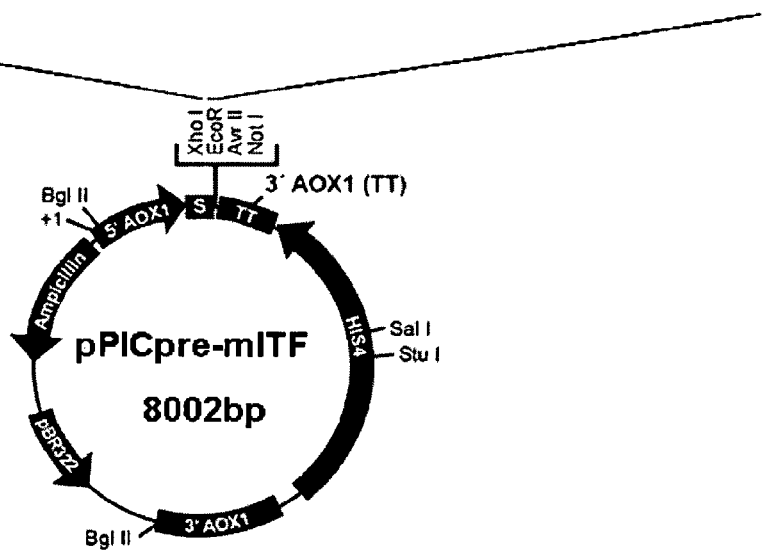

FIG. 20E shows the subcloning into pPICpre of a PCR-amplified DNA region that includes the nucleotide sequence encoding mITF$_{23-81}$, resulting in pPICpre-mITF$_{23-81}$ (also referred to as pPICpre-mITF). The PCR-amplified region corresponds to SEQ ID NO: 125.

FIG. 21A is the amino acid sequence of the MFα presequence-hITF$_{15-73}$ fusion (also referred to as MFαpre-hITF$_{15-73}$ or MFαpre-hITF) (SEQ ID NO: 316). The MFα presequence is shown in italics, the KEX2 proteolytic cleavage site is underlined, and hITF$_{15-73}$ is shown in bold.

FIG. 21B is the amino acid sequence of the MFα presequence-pITF$_{22-80}$ fusion (also referred to as MFαpre-pITF$_{22-80}$ or MFαpre-pITF) (SEQ ID NO: 317). The MFα presequence is shown in italics, the KEX2 proteolytic cleavage site is underlined, and pITF$_{22-80}$ is shown in bold.

FIG. 21C is the amino acid sequence of the MFα presequence-dITF$_{22-80}$ fusion (also referred to as MFαpre-dITF$_{22-80}$ or MFαpre-dITF) (SEQ ID NO: 318). The MFα presequence is shown in italics, the KEX2 proteolytic cleavage site is underlined, and dITF$_{22-80}$ is shown in bold.

FIG. 21D is the amino acid sequence of the MFα presequence-rITF$_{23-81}$ fusion (also referred to as MFαpre-rITF$_{23-81}$ or MFαpre-rITF) (SEQ ID NO: 319). The MFα presequence is shown in italics, the KEX2 proteolytic cleavage site is underlined, and rITF$_{23-81}$ is shown in bold.

FIG. 21E is the amino acid sequence of the MFα presequence-mITF$_{23-81}$ fusion (also referred to as MFαpre-mITF$_{23-81}$ or MFαpre-mITF) (SEQ ID NO: 320). The MFα presequence is shown in italics, the KEX2 proteolytic cleavage site is underlined, and mITF$_{23-81}$ is shown in bold.

Figure 22:
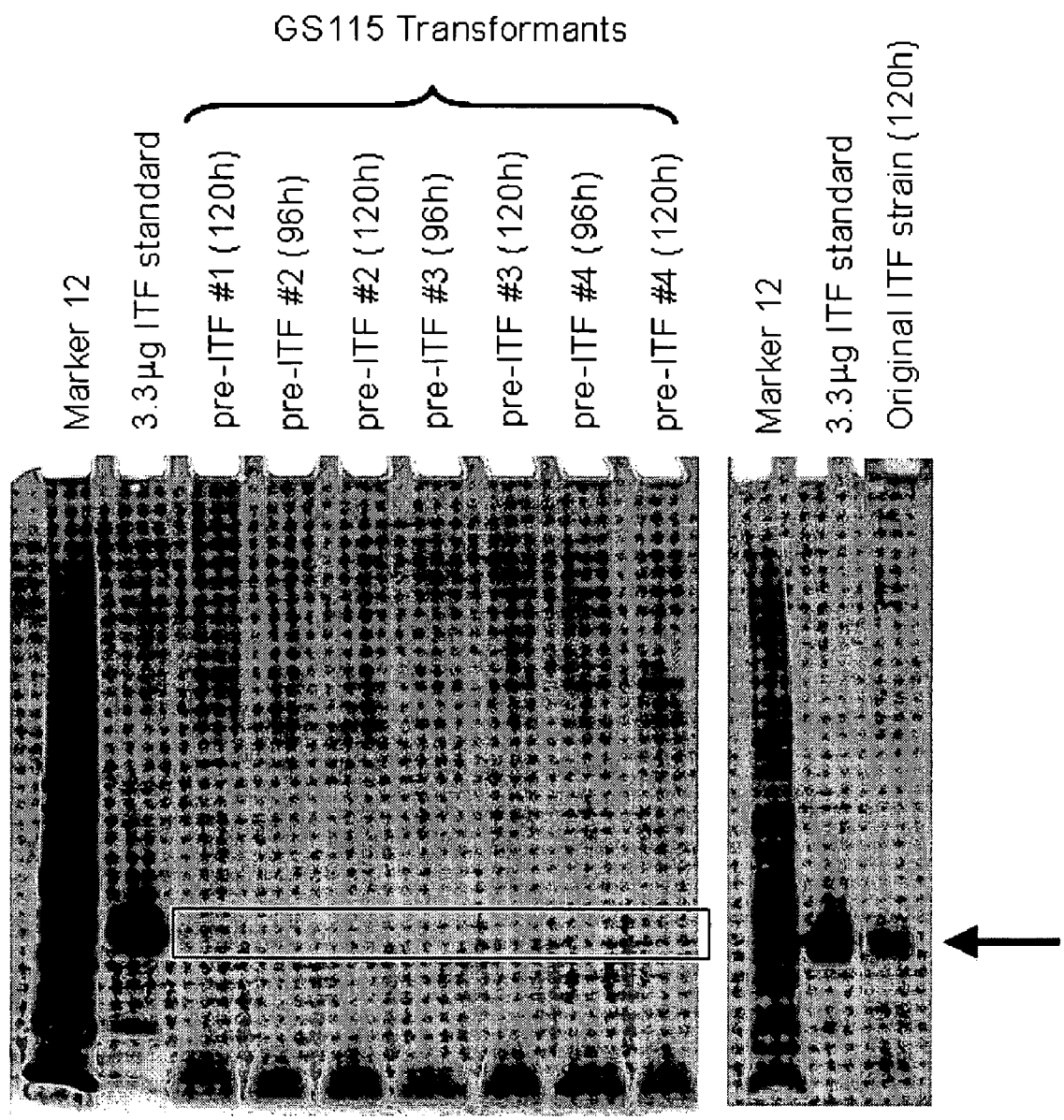

FIG. 22 is an image of a silver-stained SDS-PAGE gel characterizing four pPICpre-hITF$_{15-73}$ transformants in the *Pichia pastoris* GS115 strain. The position of hITF$_{15-73}$ is indicated by an arrow.

FIG. 23A is an image of a Coomassie-stained SDS-PAGE gel characterizing nine pPICGIco-hITF$_{15-73}$ transformants in the *Pichia pastoris* GS115 strain.

FIG. 23B is an image of a Western blot characterizing nine pPICGIco-hITF$_{15-73}$ transformants in the *Pichia pastoris* GS115 strain. The position of hITF$_{15-73}$ is indicated by an arrow.

FIG. 24A is an image of a Coomassie-stained SDS-PAGE gel characterizing the pPICGIco-hITF$_{15-73}$ transformant clone 3-24 in the *Pichia pastoris* GS115 strain.

FIG. 24B is an image of a Western blot characterizing the pPICGIco-hITF$_{15-73}$ transformant clone 3-24 in the *Pichia pastoris* GS115 strain. The position of hITF$_{15-73}$ is indicated by an arrow.

DETAILED DESCRIPTION OF THE INVENTION

Figure 1:
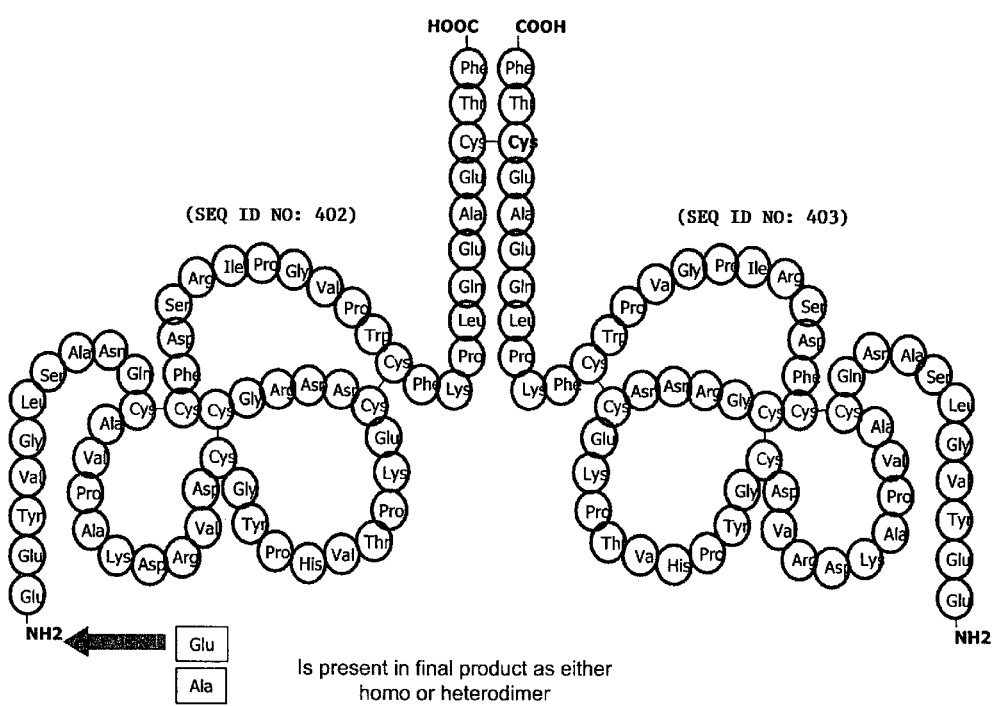
FIG. 1 is a schematic representation of the $hITF_{15-73}$ dimer including the extraneous N-terminal residues Glu-Ala shown for one of the two molecules of the dimer.
Figure 2:
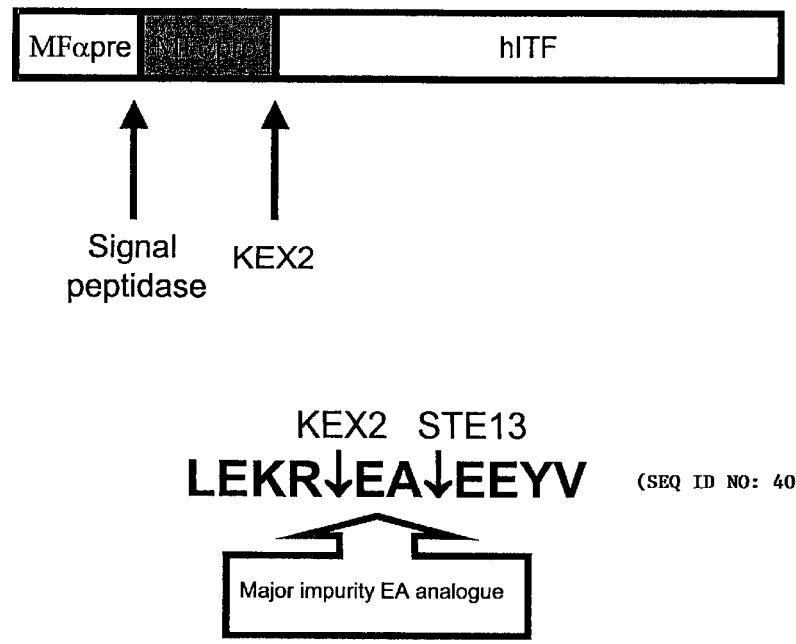
FIG. 2 is a representation of an $MF\alpha$-$hITF_{15-73}$ construct that includes the extraneous residues Glu-Ala, with cleavage sites for signal peptidase, KEX2, and STE13 indicated.
Figure 3:
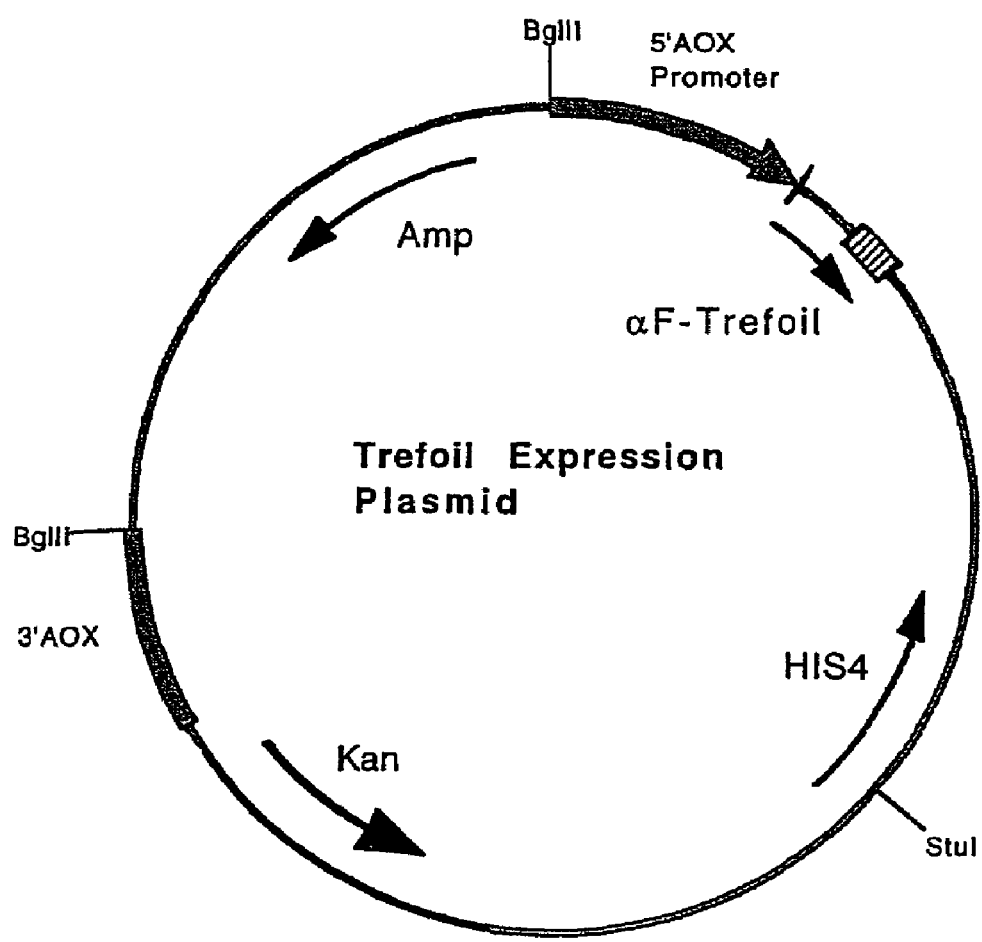
FIG. 3 is a map of an $MF\alpha$-$hITF_{15-73}$ construct.

A vector designed for expression in *P. pastoris* is shown in FIG. 3, and the corresponding protein product is shown in FIG. 2. This construct includes an N-terminal mating factor α (MFα) signal sequence fused to residues 15-73 of human ITF. The MFα signal sequence is cleaved in vivo, and the cleaved protein is secreted from the cell into the expression medium. Signal peptidase cleaves at the junction between the MFα pre sequence and the MFα pro sequence, while KEX2 cleaves near the N-terminal end of the hITF$_1$ 573 polypeptide, between residues Arg and Glu (FIG. 2). The protease STE13 cleaves the remaining Glu-Ala sequence from the ITF$_{15-73}$ polypeptide, but it does so only with approximately 70% efficiency, resulting in approximately 30% of the expression product containing an extraneous dipeptide fusion at the N-terminal end (FIG. 1). These extraneous residues result in greater heterogeneity and potentially greater antigenicity of the expression product. In addition, because hITF has a cysteine residue near the C-terminal end, causing the peptide to form dimers by disulfide-bonding, the complexity in the resulting preparation is increased by the presence of two homodimers (hITF$_{15-73}$:hITF$_{15-73}$ and EA-hITF$_{15-73}$:EA-hITF$_{15-73}$) and a heterodimer (EA-hITF$_{15-73}$:hITF$_{15-73}$). This reduces the yield of the native homodimeric hITF$_{15-73}$.

In order to facilitate the preparation of expression vectors capable of producing ITF free of extraneous residues, the vector pPICGIco is created (FIGS. 5 and 11A-11B). pPICGIco, which encodes the MFα signal sequence and has the sequence of SEQ ID NO: 2, is generated by linearizing the plasmid pPIC9 (Invitrogen) (FIG. 4) with the restriction endonucleases Xho I and SnaB I in accordance with the vendor's instructions (New England Biolabs, Inc.). This reaction eliminates the DNA segment between the Xho I sites and the SnaB I sites that code for the KEX2 recognition sequence and the Glu-Ala (EA) spacer. The 5'-overhang is filled in with DNA polymerase in the presence of dNTPs to produce blunt ends. The blunt-ended vector is circularized by blunt-end ligation in the presence of DNA ligase (New England Biolabs, Inc.). The DNA preparation is then transformed into a bacterial host (*E. coli* HB101) and transformants selected from LB agar plates containing ampicillin. The resulting vector, pPICGIco, is isolated from these transformants and identified by restriction endonuclease analysis, in which the loss of the SnaB I site and retention of the Xho I and EcoR I sites in the multiple cloning site are tested.

It is also desirable to create fusion proteins in which the MFα presequence is fused to the protein of interest, rather than the full MFα prepropeptide sequence. Thus, a second expression vector encoding the MFα presequence, pPICpre, is created based on pPICGIco (FIGS. 8 and 12A-12C). pPICpre, which has the sequence of SEQ ID NO: 5, is generated by linearizing pPICGIco with the restriction endonucleases BamH I and Xho I in accordance with the vendor's instructions (New England Biolabs, Inc.). This reaction eliminates the DNA segment between the BamH I and Xho I sites that code for the MFα signal sequence. An insert containing the MFα presequence is prepared by PCR reaction using primers having the sequences of SEQ ID NO: 241 and SEQ ID NO: 242, with pPICGIco used as a template (FIG. 12B). The resulting fragment has the sequence of SEQ ID NO: 131. This PCR fragment is cleaved with the restriction enzymes BamH I and Xho I to generate ends compatible with subcloning into pPICGIco previously cleaved with BamH I and Xho I. The linearized pPICGIco vector and PCR insert are ligated in the presence of DNA ligase. The DNA preparation is transformed into a bacterial host (*E. coli* HB101) and transformants selected from LB agar plates containing ampicillin. The resulting vector, pPICpre, is isolated from these transformants.

Below, examples are described in which the vectors pPICGIco or pPICpre are utilized to prepare numerous improved ITF expression vectors of the invention. The examples are provided for the purpose of illustrating the invention and are not meant to limit the invention in any way.

EXAMPLE 1

Yeast Expression Vectors for Production of Mammalian ITF

In order to generate an expression vector encoding MFα-hITF$_{15-73}$, the following protocol is followed. Total RNA isolated from human intestine, which includes RNA molecules having the sequence of SEQ ID NO: 101, is used as a template in an RT-PCR reaction including Taq polymerase (New England Biolabs, Inc.) and primers having the sequence of SEQ ID NO: 201 and SEQ ID NO: 202. This reaction results in a PCR product having the sequence of SEQ ID NO: 106.

The resulting PCR product is then subcloned into the bacterial plasmid vector pCR2.1 (Invitrogen) using standard ligation reaction conditions in the presence of T4 DNA ligase (New England Biolabs, Inc.). The resulting clone, pCR2.1-hITF, may be sequenced using standard M13 primers adjacent to the cloning site.

Next, using pCR2.1-hITF as the template, a nucleotide sequence encoding hITF$_{15-73}$, with a KEX2 recognition sequence operably linked to the N terminus of hITF$_{15-73}$, may be obtained by performing a PCR reaction using Taq polymerase and primers having the sequence of SEQ ID NO: 211 and SEQ ID NO: 212. This reaction results in a PCR product having the sequence of SEQ ID NO: 111.

The resulting PCR product includes a Xho I site and KEX2 recognition sequence at its 5' end, and an EcoR I site at its 3' end. This PCR product is then digested with the restriction endonucleases Xho I and EcoR I. In a separate reaction, the vector pPICGIco is similarly digested with Xho I and EcoR I. The digested PCR product is subcloned into the linearized pPICGIco vector using standard ligation reaction conditions in the presence of T4 DNA ligase. The resulting clone, pPICGIco-hITF$_{15-73}$ (FIG. 6), is identified by restriction endonuclease mapping and DNA sequencing.

Other embodiments of the invention may be generated by following a similar protocol (see, e.g., FIGS. 7, 9, and 10). For example, vectors expressing fusion proteins containing alternative fragments of human ITF may be created. In addition, ITF from different species may be used. Desirable embodiments include, but are not limited to, vectors expression fusion proteins containing the following: hITF$_{1-73}$, hITF$_{21-62}$, hITF$_{21-70}$, hITF$_{21-72}$, hITF$_{21-73}$, hITF$_{22-62}$, hITF$_{22-70}$, hITF$_{22-72}$, hITF$_{22-73}$, hITF$_{25-62}$, hITF$_{25-70}$, hITF$_{25-72}$, hITF$_{25-73}$, pITF$_{1-80}$, pITF$_{22-80}$, dITF$_{1-80}$, dITF$_{22-80}$, rITF$_{1-81}$, rITF$_{23-81}$, mITF$_{1-81}$, and mITF$_{22-81}$.

Table 1 lists DNA sequences used in generating several desirable embodiments of the invention (see FIGS. 13A-21E). For each embodiment represented therein, the sequences shown may be substituted into the protocol described above for generating a vector expressing MFα-hITF$_{15-73}$. Embodiments 1-10 make use of the pPICGIco vector in the final subcloning step, while embodiments 11-15 instead make use of the pPICpre vector in the final subcloning step.

TABLE 1

| A Embodiment # | B Template | C 1$^{st}$ 5' primer | D 1$^{st}$ 3' primer | E 1$^{st}$ PCR product | F 2$^{nd}$ 5' primer | G 2$^{nd}$ 3' primer | H 2$^{nd}$ PCR product | I Resulting vector expresses: |
|---|---|---|---|---|---|---|---|---|
| 1 | SEQ ID NO: 101 | SEQ ID NO: 201 | SEQ ID NO: 202 | SEQ ID NO: 106 | SEQ ID NO: 211 | SEQ ID NO: 212 | SEQ ID NO: 111 | MFα-hITF$_{15-73}$ |
| 2 | SEQ ID NO: 102 | SEQ ID NO: 203 | SEQ ID NO: 204 | SEQ ID NO: 107 | SEQ ID NO: 213 | SEQ ID NO: 214 | SEQ ID NO: 112 | MFα-pITF$_{22-80}$ |
| 3 | SEQ ID NO: 103 | SEQ ID NO: 205 | SEQ ID NO: 206 | SEQ ID NO: 108 | SEQ ID NO: 215 | SEQ ID NO: 216 | SEQ ID NO: 113 | MFα-dITF$_{22-80}$ |
| 4 | SEQ ID NO: 104 | SEQ ID NO: 207 | SEQ ID NO: 208 | SEQ ID NO: 109 | SEQ ID NO: 217 | SEQ ID NO: 218 | SEQ ID NO: 114 | MFα-rITF$_{23-81}$ |
| 5 | SEQ ID NO: 105 | SEQ ID NO: 209 | SEQ ID NO: 210 | SEQ ID NO: 110 | SEQ ID NO: 219 | SEQ ID NO: 220 | SEQ ID NO: 115 | MFα-mITF$_{23-81}$ |
| 6 | SEQ ID NO: 101 | SEQ ID NO: 201 | SEQ ID NO: 202 | SEQ ID NO: 106 | SEQ ID NO: 221 | SEQ ID NO: 222 | SEQ ID NO: 116 | MFα-hITF$_{1-73}$ |
| 7 | SEQ ID NO: 102 | SEQ ID NO: 203 | SEQ ID NO: 204 | SEQ ID NO: 107 | SEQ ID NO: 223 | SEQ ID NO: 224 | SEQ ID NO: 117 | MFα-pITF$_{1-80}$ |
| 8 | SEQ ID NO: 103 | SEQ ID NO: 205 | SEQ ID NO: 206 | SEQ ID NO: 108 | SEQ ID NO: 225 | SEQ ID NO: 226 | SEQ ID NO: 118 | MFα-dITF$_{1-80}$ |
| 9 | SEQ ID NO: 104 | SEQ ID NO: 207 | SEQ ID NO: 208 | SEQ ID NO: 109 | SEQ ID NO: 227 | SEQ ID NO: 228 | SEQ ID NO: 119 | MFα-rITF$_{1-81}$ |
| 10 | SEQ ID NO: 105 | SEQ ID NO: 209 | SEQ ID NO: 210 | SEQ ID NO: 110 | SEQ ID NO: 229 | SEQ ID NO: 230 | SEQ ID NO: 120 | MFα-mITF$_{1-81}$ |
| 11 | SEQ ID NO: 101 | SEQ ID NO: 201 | SEQ ID NO: 202 | SEQ ID NO: 106 | SEQ ID NO: 231 | SEQ ID NO: 232 | SEQ ID NO: 121 | MFαpre-hITF$_{15-73}$ |
| 12 | SEQ ID NO: 102 | SEQ ID NO: 203 | SEQ ID NO: 204 | SEQ ID NO: 107 | SEQ ID NO: 233 | SEQ ID NO: 234 | SEQ ID NO: 122 | MFαpre-pITF$_{22-80}$ |
| 13 | SEQ ID NO: 103 | SEQ ID NO: 205 | SEQ ID NO: 206 | SEQ ID NO: 108 | SEQ ID NO: 235 | SEQ ID NO: 236 | SEQ ID NO: 123 | MFαpre-dITF$_{22-80}$ |
| 14 | SEQ ID NO: 104 | SEQ ID NO: 207 | SEQ ID NO: 208 | SEQ ID NO: 109 | SEQ ID NO: 237 | SEQ ID NO: 238 | SEQ ID NO: 124 | MFαpre-rITF$_{23-81}$ |
| 15 | SEQ ID NO: 105 | SEQ ID NO: 209 | SEQ ID NO: 210 | SEQ ID NO: 110 | SEQ ID NO: 239 | SEQ ID NO: 240 | SEQ ID NO: 125 | MFαpre-mITF$_{23-81}$ |

Table 2 lists primer sequences used in the protocols described above.

TABLE 2

| Primer ID | Sequence (5' to 3') |
|---|---|
| SEQ ID NO: 201 | CTGCCAGAGCGCTCTGCATG |
| SEQ ID NO: 202 | CTGGAGGTGCCTCAGAAGGT |
| SEQ ID NO: 203 | ATGGAGGCCAGGATGTTCTG |
| SEQ ID NO: 204 | TCAGAAGGTGCATTCTGTTT |
| SEQ ID NO: 205 | AACGATCTCTGAGCGGTCGG |
| SEQ ID NO: 206 | TGCTTCAAAATCTGCATTCT |
| SEQ ID NO: 207 | TGCTGCCATGGAGACCAGAG |
| SEQ ID NO: 208 | CTGGAGCCTGGACAGCTTCA |
| SEQ ID NO: 209 | AGCTTGCCTGCTGCCATGGA |
| SEQ ID NO: 210 | TCCTGGAGCCTGGACAGCTT |
| SEQ ID NO: 211 | CTCGAGAAAAGAGAGGAGTACGTGGGCCTGT |
| SEQ ID NO: 212 | GAATTCTCAGAAGGTGCATTCTGCT |
| SEQ ID NO: 213 | CTCGAGAAAAGAGCCGGGGAGTATGTGGGC |
| SEQ ID NO: 214 | GAATTCTCAGAAGGTGCATTCTGTTT |
| SEQ ID NO: 215 | CTCGAGAAAAGAGTGGCTTACCAGGGCCTG |
| SEQ ID NO: 216 | GAATTCTCAAAATCTGCATTCTGT |
| SEQ ID NO: 217 | CTCGAGAAAAGACAGGAATTTGTTGGCCTA |
| SEQ ID NO: 218 | GAATTCTCAAAATGTACATTCTGT |
| SEQ ID NO: 219 | CTCGAGAAAAGAGCAGATTACGTTGGCCTG |

TABLE 2-continued

| Primer ID | Sequence (5' to 3') |
|---|---|
| SEQ ID NO: 220 | GAATTCTCAAAATGTGCATTCTGT |
| SEQ ID NO: 221 | CTCGAGAAAAGAATGCTGGGGCTGGTCCTGGC |
| SEQ ID NO: 222 | GAATTCTCAGAAGGTGCATTCTGCT |
| SEQ ID NO: 223 | CTCGAGAAAAGAATGGAGGCCAGGATGTTC |
| SEQ ID NO: 224 | GAATTCTCAGAAGGTGCATTCTGTTT |
| SEQ ID NO: 225 | CTCGAGAAAAGAATGGAGGCCAGAGTGCT |
| SEQ ID NO: 226 | GAATTCTCAAAATCTGCATTCTGT |
| SEQ ID NO: 227 | CTCGAGAAAAGAATGGAGACCAGAGCCTTC |
| SEQ ID NO: 228 | GAATTCTCAAAATGTACATTCTGT |
| SEQ ID NO: 229 | CTCGAGAAAAGAGCAGATTACGTTGGCCTG |
| SEQ ID NO: 230 | GAATTCTCAAAATGTGCATTCTGT |
| SEQ ID NO: 231 | CTCGAGAAAAGAGAGGAGTACGTGGGCCTGT |
| SEQ ID NO: 232 | GAATTCTCAGAAGGTGCATTCTGCT |
| SEQ ID NO: 233 | CTCGAGAAAAGAGCCGGGGAGTATGTGGGC |
| SEQ ID NO: 234 | GAATTCTCAGAAGGTGCATTCTGTTT |
| SEQ ID NO: 235 | CTCGAGAAAAGAGTGGCTTACCAGGGCCTG |
| SEQ ID NO: 236 | GAATTCTCAAAATCTGCATTCTGT |
| SEQ ID NO: 237 | CTCGAGAAAAGACAGGAATTTGTTGGCCTA |
| SEQ ID NO: 238 | GAATTCTCAAAATGTACATTCTGT |
| SEQ ID NO: 239 | CTCGAGAAAAGAGCAGATTACGTTGGCCTG |
| SEQ ID NO: 240 | GAATTCTCAAAATGTGCATTCTGT |
| SEQ ID NO: 241 | GGATCCAAACGATGAGA |
| SEQ ID NO: 242 | CTCGAGAGCAGCTAATGCGGATGC |

Variants of the above-described embodiments of the invention are possible. For example, alternative protease cleavage sites may be used in place of the KEX2 site. Cleavage sites recognized by any of the following enzymes would be useful: yeast aspartic protease (Yap3), Type IV dipeptidyl aminopeptidase (DPAP), yeast glycosyl-phosphatidylinositol-linked aspartyl protease (Mkc7), pepsin, trypsin, chymotrypsin, and subtilisin. Yap3 cleaves immediately C-terminal to Arg residues (Bourbonnais et al., Biochimie, 76:226-233, 1994) and cleaves following Arg-Arg and Lys-Arg sites, though it cleaves poorly after three or more consecutive basic residues (Ledgerwood et al., FEBS Lett., 383:67-71, 1996); DPAP cleaves immediately C-terminal to Ala or Pro residues, including Leu-Pro and Val-Pro sites (Brenner et al., Proc Natl Acad Sci U.S.A., 89:922-926, 1992); Mkc7 cleaves immediately C-terminal to Lys-Arg (Komano et al., Proc Natl Acad Sci USA, 92:10752-10756, 1995); pepsin cleaves immediately C-terminal to Tyr, Phe, or Trp residues; trypsin cleaves immediately C-terminal to Arg or Lys residues; and chymotrypsin cleaves immediately C-terminal to Tyr, Phe, or Trp residues.

Vectors of the invention are designed so that, as with the KEX2 site in the vectors described above, no extraneous residues are present between an alternative protease cleavage site and the sequence encoding the ITF polypeptide to be expressed. Cleavage of the resulting MFα-ITF fusion protein may occur in vivo prior to secretion; for example, this could occur with cleavage sites recognized by proteases that occur naturally in the host, such as Yap3, DPAP, or Mkc7. Alternatively, uncleaved fusion protein may be secreted by the host cell if no endogenous enzyme recognizes the cleavage site of the fusion construct; in this case, cleavage may be achieved in vitro in a reaction chamber by contacting purified secreted fusion protein with a purified endoprotease such as pepsin, trypsin, chymotrypsin, subtilisin, or other enzymes. Mature ITF is known to be resistant to the action of such proteases in solution (Kinoshita et al., Mol Cell Biol., 20:4680-4690, 2000) and so will remain intact following the reaction. Subsequently, the resulting ITF polypeptide may be purified away from protease and reaction products.

Additionally, alternative embodiments are possible in which an N-terminal fusion sequence other than an MFα signal sequence or an MFα presequence is used. Any N-terminal fusion sequence that results in secretion of the expressed ITF polypeptide is useful in the methods of the invention. N-terminal fusion sequences that do not result in secretion are also possible; in such cases, the cells in which expression occurs would be lysed prior to protein extraction and purification. Signal and leader sequences for yeast expression include the yeast K28 virus preprotoxin secretion signal sequence (Eiden-Plach et al., Appl Environ Microbiol., 70:961-966, 2004), Sacchromyces cerevisiae acid phosphatase signal sequence (Akeboshi et al., Biosci Biotechnol Biochem., 67:1149-1153, 2003), *Aspergillus niger* isopullulanase signal sequence (Akeboshi et al., Biosci Biotechnol Biochem., 67:1149-1153, 2003), chimeric yeast alpha factor and *streptomyces* mobaraensis transglataminase propeptide (Yurimoto et al., Biosci Biotechnol Biochem., 68:2058-2069, 2004), modified signal peptide for *rhizopus oryzae* glucoamylase (Liu et al, Biochem Biophys Res Commun., 326: 817-824, 2005), *Kluyveromyces lactis* killer toxin signal sequence (Tokunaga et al., Yeast, 9:379-397, 1993), and Map2 secretion sequence (Giga-Hama et al., Biotech Appl Biochem., 30:235-244, 1999).

In each instance described above, as well as in other embodiments of the invention, standard methods of protein purification may be used. See, for example, the purification methods and activity assays described in Thim et al., Biochemistry, 34:4757-4764, 1995, and U.S. Ser. No. 10/698, 572, each of which are hereby incorporated by reference.

Host organisms for yeast expression vectors may be chosen, e.g., from among *Pichia pastoris, Saccharomyces cerevisiae, Schizosaccharomyces pombe, Candida boidinii*, and *Candida glabrata* (Yurimoto et al., Biosci Biotechnol Biochem., 68:2058-2069, 2004; Eiden-Plach et al., Appl Environ Microbiol., 70:961-966, 2004). Desirably, the *Pichia pastoris* GS115 (his4-) strain is used. Other host organisms may also be used.

Organisms produced according to the invention may be employed in industrial scale production of human ITF, yielding product in quantities and for applications hitherto unattainable.

EXAMPLE 2

Expression Of pPICpre-hITF$_{15-73}$

The pPICpre-hITF$_{15-73}$ construct was transformed into *Pichia pastoris* strain GS115(Mut+), and transformants were selected. Expression of hITF$_{15-73}$ (mol weight: ~6.5 KDa) secreted into the media after 96-120 hours of growth in shake flasks was assessed using SDS-PAGE (FIG. 22). A construct expressing EA-hITF$_{15-73}$ was used as a control. Four GS115 clones were tested, and clone pre-ITF #1 showed expression of a band comparable in size to that of hITF$_{15-73}$. These data demonstrate that the pPICpre-hITF$_{15-73}$ construct directs expression of hITF$_{15-73}$.

EXAMPLE 3

Expression of pPICGIco-hITF$_{15-73}$

The pPICGIco-hITF$_{15-73}$ construct was transformed into *Pichia pastoris* strains GS115(Mut+), and transformants were selected. Expression of hITF$_{15-73}$ (mol weight: ~6.5 KDa) secreted into the media after 120 hours of growth in shake flasks was assessed using SDS-PAGE (FIGS. 23A and 24A) and Western blot (FIGS. 23B and 24B). A construct expressing EA-hITF$_{15-73}$ was used as a control. Nine GS115 clones were tested; clones 3-19, 3-24, 3-25, and 3-26 showed expression of a band comparable in size to that of hITF$_{15-73}$, and Western blotting confirmed that this band contained hITF. The data demonstrate that the pPICGIco-hITF$_{15-73}$ construct directs expression of hITF$_{15-73}$.

Use

The invention provides ITF expression vectors and methods of their use for treating epithelial cell lesions. Lesions amenable to treatment using the expression products and methods of this invention include epithelial lesions of the dermis and epidermis (skin), alimentary canal including the epithelia of the oral cavity, esophagus, stomach, small and large intestines (anal sphincter, rectum, and colon, particularly the sigmoid colon and the descending colon), genitourinary tract (particularly the vaginal canal, cervix, and uterus), trachea, lungs, nasal cavity, and the eye.

Other Embodiments

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An expression vector comprising a nucleic acid having the sequence of SEQ ID NO:2.

2. An expression vector comprising a nucleic acid having the sequence of SEQ ID NO: 5.

* * * * *

SEQUENCE LISTING

```
<160> NUMBER OF SEQ ID NOS: 405

<210> SEQ ID NO 1
<211> LENGTH: 8023
<212> TYPE: DNA
<213> ORGANISM: Artificial
<220> FEATURE:
<223> OTHER INFORMATION: synthetic

<400> SEQUENCE: 1
agatctaaca tccaaagacg aaaggttgaa tgaaaccttt ttgccatccg acatccacag      60
gtccattctc acacataagt gccaaacgca acaggagggg atacactagc agcagaccgt     120
tgcaaacgca ggacctccac tcctcttctc ctcaacaccc acttttgcca tcgaaaaacc    180
agcccagtta ttgggcttga ttggagctcg ctcattccaa ttccttctat taggctacta    240
acaccatgac tttattagcc tgtctatcct ggcccccctg gcgaggttca tgtttgttta    300
tttccgaatg caacaagctc cgcattacac ccgaacatca ctccagatga gggctttctg    360
agtgtggggt caaatagttt catgttcccc aaatggccca aaactgacag tttaaacgct    420
gtcttggaac ctaatatgac aaaagcgtga tctcatccaa gatgaactaa gtttggttcg    480
ttgaaatgct aacggccagt tggtcaaaaa gaaacttcca aaagtcgcca taccgtttgt    540
cttgtttggt attgattgac gaatgctcaa aaataatctc attaatgctt agcgcagtct    600
ctctatcgct tctgaacccc ggtgcacctg tgccgaaacg caaatgggga aacacccgct    660
ttttggatga ttatgcattg tctccacatt gtatgcttcc aagattctgg tgggaatact    720
gctgatagcc taacgttcat gatcaaaatt taactgttct aaccoctact tgacagcaat    780 atataaacag aaggaagctg ccctgtctta aacctttttt tttatcatca ttattagctt    840
actttcataa ttgcgactgg ttccaattga caagcttttg attttaacga cttttaacga    900
caacttgaga agatcaaaaa acaactaatt attcgaagga tccaaacgat gagatttcct    960
tcaattttta ctgcagtttt attcgcagca tcctccgcat tagctgctcc agtcaacact   1020
```

```
acaacagaag atgaaacggc acaaattccg gctgaagctg tcatcggtta ctcagattta   1080 gaagggatt tcgatgttgc tgttttgcca ttttccaaca gcacaaataa cgggttattg   1140
tttataaata ctactattgc cagcattgct gctaaagaag aagggtatc tctcgagaaa   1200 agagaggctg aagcttacgt agaattccct agggcggccg cgaattaatt cgccttagac   1260
atgactgttc ctcagttcaa gttgggcact tacgagaaga ccggtcttgc tagattctaa   1320
tcaagaggat gtcagaatgc catttgcctg agagatgcag gcttcatttt tgatactttt   1380
ttatttgtaa cctatatagt ataggatttt ttttgtcatt ttgtttcttc tcgtacgagc   1440
ttgctcctga tcagcctatc tcgcagctga tgaatatctt gtggtagggg tttgggaaaa   1500
tcattcgagt ttgatgtttt tcttggtatt tcccactcct cttcagagta cagaagatta   1560
agtgagaagt tcgtttgtgc aagcttatcg ataagcttta atgcggtagt ttatcacagt   1620
taaattgcta acgcagtcag gcaccgtgta tgaaatctaa caatgcgctc atcgtcatcc   1680
tcggcaccgt caccctggat gctgtaggca taggcttggt tatgccggta ctgccgggcc   1740
tcttgcggga tatcgtccat tccgacagca tcgccagtca ctatggcgtg ctgctagcgc   1800
tatatgcgtt gatgcaattt ctatgcgcac ccgttctcgg agcactgtcc gaccgctttg   1860
gccgccgccc agtcctgctc gcttcgctac ttggagccac tatcgactac gcgatcatgg   1920
cgaccacacc cgtcctgtgg atctatcgaa tctaaatgta agttaaaatc tctaaataat   1980
taaataagtc ccagtttctc catacgaacc ttaacagcat gcggtgagc atctagacct   2040 tcaacagcag ccagatccat cactgcttgg ccaatatgtt tcagtccctc aggagttacg   2100
tcttgtgaag tgatgaactt ctggaaggtt gcagtgttaa ctccgctgta ttgacgggca   2160
tatccgtacg ttggcaaagt gtggttggta ccggaggagt aatctccaca actctctgga   2220
gagtaggcac caacaaacac agatccagcg tgttgtactt gatcaacata agaagaagca   2280
ttctcgattt gcaggatcaa gtgttcagga gcgtactgat tggacatttc caaagcctgc   2340
tcgtaggttg caaccgatag ggttgtagag tgtgcaatac acttgcgtac aatttcaacc   2400
cttggcaact gcacagcttg gttgtgaaca gcatcttcaa ttctggcaag ctccttgtct   2460
gtcatatcga cagccaacag aatcacctgg gaatcaatac catgttcagc ttgagacaga   2520
aggtctgagg caacgaaatc tggatcagcg tatttatcag caataactag aacttcagaa   2580
ggcccagcag gcatgtcaat actacacagg gctgatgtgt cattttgaac catcatcttg   2640
gcagcagtaa cgaactggtt tcctggacca aatattttgt cacacttagg aacagtttct   2700
gttccgtaag ccatagcagc tactgcctgg gcgcctcctg ctagcacgat acacttagca   2760
ccaaccttgt gggcaacgta gatgacttct ggggtaaggg taccatcctt cttaggtgga   2820
gatgcaaaaa caatttcttt gcaaccagca actttggcag gaacacccag catcagggaa   2880
gtggaaggca gaattgcggt tccaccagga atatagaggc caactttctc aataggtctt   2940
gcaaaacgag agcagactac accagggcaa gtctcaactt gcaacgtctc cgttagttga   3000
gcttcatgga atttcctgac gttatctata gagagatcaa tggctctctt aacgttatct   3060
ggcaattgca taagttcctc tgggaaagga gcttctaaca caggtgtctt caaagcgact   3120
ccatcaaact tggcagttag ttctaaaagg gctttgtcac cattttgacg aacattgtcg   3180
acaattggtt tgactaattc cataatctgt tccgttttct ggataggacg acgaagggca   3240
tcttcaattt cttgtgagga ggccttagaa acgtcaattt tgcacaattc aatacgacct   3300
tcagaaggga cttctttagg tttggattct tctttaggtt gttccttggt gtatcctggc   3360
```

-continued

```
ttggcatctc ctttccttct agtgaccttt agggacttca tatccaggtt tctctccacc    3420
tcgtccaacg tcacaccgta cttggcacat ctaactaatg caaaataaaa taagtcagca    3480
cattcccagg ctatatcttc cttggattta gcttctgcaa gttcatcagc ttcctcccta    3540
attttagcgt tcaacaaaac ttcgtcgtca ataaccgtt  tggtataaga accttctgga    3600
gcattgctct tacgatccca caaggtggct ccatggctc  taagacccct tgattggcca    3660
aaacaggaag tgcgttccaa gtgacagaaa ccaacacctg tttgttcaac cacaaatttc    3720
aagcagtctc catcacaatc caattcgata cccagcaact tttgagttgc tccagatgta    3780
gcacctttat accacaaacc gtgacgacga gattggtaga ctccagtttg tgtcctata    3840 gcctccggaa tagactttt  ggacgagtac accaggccca acgagtaatt agaagagtca    3900
gccaccaaag tagtgaatag accatcgggg cggtcagtag tcaaagacgc caacaaaatt    3960
tcactgacag ggactttttt gacatcttca gaaagttcgt attcagtagt caattgccga    4020
gcatcaataa tggggattat accagaagca acagtggaag tcacatctac caactttgcg    4080
gtctcagaaa aagcataaac agttctacta ccgccattag tgaaactttt caaatcgccc    4140
agtggagaag aaaaaggcac agcgatacta gcattagcgg caaggatgc  aactttatca    4200 accagggtcc tatagataac cctagcgcct gggatcatcc tttggacaac tctttctgcc    4260
aaatctaggt ccaaaatcac ttcattgata ccattattgt acaacttgag caagttgtcg    4320
atcagctcct caaattggtc ctctgtaacg gatgactcaa cttgcacatt aacttgaagc    4380
tcagtcgatt gagtgaactt gatcaggttg tgcagctggt cagcagcata gggaaacacg    4440
gcttttccta ccaaactcaa ggaattatca aactctgcaa cacttgcgta tgcaggtagc    4500
aagggaaatg tcatacttga agtcggacag tgagtgtagt cttgagaaat tctgaagccg    4560 tattttatt  atcagtgagt cagtcatcag gagatcctct acgccggacg catcgtggcc    4620
ggcatcaccg gcgccacagg tgcggttgct ggcgcctata tcgccgacat caccgatggg    4680
gaagatcggg ctcgccactt cgggctcatg agcgcttgtt tcggcgtggg tatggtggca    4740
ggccccgtgg ccgggggact gttgggcgcc atctccttgc atgcaccatt ccttgcggcg    4800
gcggtgctca acggcctcaa cctactactg ggctgcttcc taatgcagga gtcgcataag    4860
ggagagcgtc gagtatctat gattggaagt atgggaatgg tgatacccgc attcttcagt    4920
gtcttgaggt ctcctatcag attatgccca actaaagcaa ccggaggagg agatttcatg    4980
gtaaatttct ctgacttttg gtcatcagta gactcgaact gtgagactat ctcggttatg    5040
acagcagaaa tgtccttctt ggagacagta atgaagtcc  caccaataaa gaatccttg    5100 ttatcaggaa caaacttctt gtttcgaact ttttcggtgc cttgaactat aaaatgtaga    5160
gtggatatgt cgggtaggaa tggagcgggc aaatgcttac cttctggacc ttcaagaggt    5220
atgtagggtt tgtagatact gatgccaact tcagtgacaa cgttgctatt tcgttcaaac    5280
cattccgaat ccagagaaat caaagttgtt tgtctactat tgatccaagc cagtgcggtc    5340
ttgaaactga caatagtgtg ctcgtgtttt gaggtcatct ttgtatgaat aaatctagtc    5400
tttgatctaa ataatcttga cgagccaagg cgataaatac ccaaatctaa aactcttta    5460 aaacgttaaa aggacaagta tgtctgcctg tattaaaccc caaatcagct cgtagtctga    5520
tcctcatcaa cttgagggc  actatcttgt tttagagaaa tttgcggaga tgcgatatcg    5580
agaaaaaggt acgctgattt taaacgtgaa atttatctca agatctctgc ctcgcgcgtt    5640
tcggtgatga cggtgaaaac ctctgacaca tgcagctccc ggagacgtc  acagcttgtc    5700 tgtaagcgga tgccgggagc agacaagccc gtcagggcgc gtcagcgggt gttggcgggt    5760
```

```
gtcggggcgc agccatgacc cagtcacgta gcgatagcgg agtgtatact ggcttaacta    5820
tgcggcatca gagcagattg tactgagagt gcaccatatg cggtgtgaaa taccgcacag    5880
atgcgtaagg agaaaatacc gcatcaggcg ctcttccgct tcctcgctca ctgactcgct    5940
gcgctcggtc gttcggctgc ggcgagcggt atcagctcac tcaaaggcgg taatacggtt    6000
atccacagaa tcaggggata acgcaggaaa gaacatgtga gcaaaaggcc agcaaaaggc    6060
caggaaccgt aaaaaggccg cgttgctggc gtttttccat aggctccgcc cccctgacga    6120
gcatcacaaa aatcgacgct caagtcagag gtggcgaaac ccgacaggac tataaagata    6180
ccaggcgttt ccccctggaa gctccctcgt gcgctctcct gttccgaccc tgccgcttac    6240
cggatacctg tccgcctttc tcccttcggg aagcgtggcg ctttctcaat gctcacgctg    6300
taggtatctc agttcggtgt aggtcgttcg ctccaagctg ggctgtgtgc acgaaccccc    6360
cgttcagccc gaccgctgcg ccttatccgg taactatcgt cttgagtcca acccggtaag    6420
acacgactta tcgccactgg cagcagccac tggtaacagg attagcagag cgaggtatgt    6480
aggcggtgct acagagttct tgaagtggtg gcctaactac ggctacacta aggacagt    6540 atttggtatc tgcgctctgc tgaagccagt taccttcgga aaaagagttg gtagctcttg    6600
atccggcaaa caaaccaccg ctggtagcgg tggttttttt gtttgcaagc agcagattac    6660
gcgcagaaaa aaaggatctc aagaagatcc tttgatcttt tctacggggt ctgacgctca    6720
gtggaacgaa aactcacgtt aagggatttt ggtcatgaga ttatcaaaaa ggatcttcac    6780
ctagatcctt ttaaattaaa aatgaagttt taaatcaatc taaagtatat atgagtaaac    6840
ttggtctgac agttaccaat gcttaatcag tgaggcacct atctcagcga tctgtctatt    6900
tcgttcatcc atagttgcct gactccccgt cgtgtagata actacgatac gggagggctt    6960
accatctggc cccagtgctg caatgatacc gcgagaccca cgctcaccgg ctccagattt    7020
atcagcaata aaccagccag ccggaagggc cgagcgcaga agtggtcctg caactttatc    7080
cgcctccatc cagtctatta attgttgccg ggaagctaga gtaagtagtt cgccagttaa    7140
tagtttgcgc aacgttgttg ccattgctgc aggcatcgtg gtgtcacgct cgtcgtttgg    7200
tatggcttca ttcagctccg gttcccaacg atcaaggcga gttacatgat cccccatgtt    7260
gtgcaaaaaa gcggttagct ccttcggtcc tccgatcgtt gtcagaagta agttggccgc    7320
agtgttatca ctcatggtta tggcagcact gcataattct cttactgtca tgccatccgt    7380
aagatgcttt tctgtgactg gtgagtactc aaccaagtca ttctgagaat agtgtatgcg    7440
gcgaccgagt tgctcttgcc cggcgtcaac acgggataat accgcgccac atagcagaac    7500
tttaaaagtg ctcatcattg gaaaacgttc ttcgggcga aaactctcaa ggatcttacc    7560
gctgttgaga tccagttcga tgtaacccac tcgtgcaccc aactgatctt cagcatcttt    7620
tactttcacc agcgtttctg ggtgagcaaa aacaggaagg caaaatgccg caaaaaggg    7680 aataagggcg acacggaaat gttgaatact catactcttc ctttttcaat attattgaag    7740
catttatcag ggttattgtc tcatgagcgg atacatattt gaatgtattt agaaaaataa    7800
acaaataggg gttccgcgca catttccccg aaaagtgcca cctgacgtct aagaaaccat    7860
tattatcatg acattaacct ataaaaatag gcgtatcacg aggccctttc gtcttcaaga    7920
attaattctc atgtttgaca gcttatcatc gataagctga ctcatgttgg tattgtgaaa    7980
tagacgcaga tcgggaacac tgaaaaataa cagttattat tcg                      8023
```

<210> SEQ ID NO 2

<211> LENGTH: 8001
<212> TYPE: DNA
<213> ORGANISM: Artificial
<220> FEATURE:
<223> OTHER INFORMATION: synthetic

<400> SEQUENCE: 2

| | | | | | |
|---|---|---|---|---|---|
| agatctaaca | tccaaagacg | aaaggttgaa | tgaaaccttt | ttgccatccg | acatccacag | 60 |
| gtccattctc | acacataagt | gccaaacgca | acaggagggg | atacactagc | agcagaccgt | 120 |
| tgcaaacgca | ggacctccac | tcctcttctc | ctcaacaccc | acttttgcca | tcgaaaaacc | 180 |
| agcccagtta | ttgggcttga | ttggagctcg | ctcattccaa | ttccttctat | taggctacta | 240 |
| acaccatgac | tttattagcc | tgtctatcct | ggccccctg | gcgaggttca | tgtttgttta | 300 |
| tttccgaatg | caacaagctc | cgcattacac | ccgaacatca | ctccagatga | gggctttctg | 360 |
| agtgtggggt | caaatagttt | catgttcccc | aaatggccca | aaactgacag | tttaaacgct | 420 |
| gtcttggaac | ctaatatgac | aaaagcgtga | tctcatccaa | gatgaactaa | gtttggttcg | 480 |
| ttgaaatgct | aacggccagt | tggtcaaaaa | gaaacttcca | aaagtcgcca | taccgtttgt | 540 |
| cttgtttggt | attgattgac | gaatgctcaa | aaataatctc | attaatgctt | agcgcagtct | 600 |
| ctctatcgct | tctgaacccc | ggtgcacctg | tgccgaaacg | caaatgggga | acacccgct | 660 |
| ttttggatga | ttatgcattg | tctccacatt | gtatgcttcc | aagattctgg | tgggaatact | 720 |
| gctgatagcc | taacgttcat | gatcaaaatt | taactgttct | aacccctact | tgacagcaat | 780 |
| atataaacag | aaggaagctg | ccctgtctta | aacctttttt | tttatcatca | ttattagctt | 840 |
| actttcataa | ttgcgactgg | ttccaattga | caagcttttg | attttaacga | cttttaacga | 900 |
| caacttgaga | agatcaaaaa | acaactaatt | attcgaagga | tccaaacgat | gagatttcct | 960 |
| tcaattttta | ctgcagtttt | attcgcagca | tcctccgcat | tagctgctcc | agtcaacact | 1020 |
| acaacagaag | atgaaacggc | acaaattccg | gctgaagctg | tcatcggtta | ctcagattta | 1080 |
| gaagggggatt | tcgatgttgc | tgttttgcca | ttttccaaca | gcacaaataa | cgggttattg | 1140 |
| tttataaata | ctactattgc | cagcattgct | gctaaagaag | aagggggtatc | tctcgagtag | 1200 |
| aattccctag | ggcggccgcg | aattaattcg | ccttagacat | gactgttcct | cagttcaagt | 1260 |
| tgggcactta | cgagaagacc | ggtcttgcta | gattctaatc | aagaggatgt | cagaatgcca | 1320 |
| tttgcctgag | agatgcaggc | ttcatttttg | atactttttt | atttgtaacc | tatatagtat | 1380 |
| aggattttt | ttgtcatttt | gtttcttctc | gtacgagctt | gctcctgatc | agcctatctc | 1440 |
| gcagctgatg | aatatcttgt | ggtaggggtt | tgggaaaatc | attcgagttt | gatgttttc | 1500 |
| ttggtatttc | ccactcctct | tcagagtaca | aagattaag | tgagaagttc | gtttgtgcaa | 1560 |
| gcttatcgat | aagctttaat | gcggtagttt | atcacagtta | aattgctaac | gcagtcaggc | 1620 |
| accgtgtatg | aaatctaaca | atgcgctcat | cgtcatcctc | ggcaccgtca | ccctggatgc | 1680 |
| tgtaggcata | ggcttggtta | tgccggtact | gccgggcctc | ttgcgggata | tcgtccattc | 1740 |
| cgacagcatc | gccagtcact | atggcgtgct | gctagcgcta | tatgcgttga | tgcaatttct | 1800 |
| atgcgcaccc | gttctcggag | cactgtccga | ccgctttggc | cgccgccag | tcctgctcgc | 1860 |
| ttcgctactt | ggagccacta | tcgactacgc | gatcatggcg | accacacccg | tcctgtggat | 1920 |
| ctatcgaatc | taaatgtaag | ttaaaatctc | taaataatta | aataagtccc | agtttctcca | 1980 |
| tacgaacctt | aacagcattg | cggtgagcat | ctagaccttc | aacagcagcc | agatccatca | 2040 |
| ctgcttggcc | aatatgtttc | agtccctcag | gagttacgtc | ttgtgaagtg | atgaacttct | 2100 |
| ggaaggttgc | agtgttaact | ccgctgtatt | gacgggcata | tccgtacgtt | ggcaaagtgt | 2160 |

```
ggttggtacc ggaggagtaa tctccacaac tctctggaga gtaggcacca acaaacacag    2220
atccagcgtg ttgtacttga tcaacataag aagaagcatt ctcgatttgc aggatcaagt    2280
gttcaggagc gtactgattg gacatttcca agcctgctc gtaggttgca accgataggg     2340
ttgtagagtg tgcaatacac ttgcgtacaa tttcaaccct tggcaactgc acagcttggt    2400
tgtgaacaga tcttcaatt ctggcaagct ccttgtctgt catatcgaca gccaacagaa     2460
tcacctggga atcaatacca tgttcagctt gagacagaag gtctgaggca acgaaatctg    2520
gatcagcgta tttatcagca ataactagaa cttcagaagg cccagcaggc atgtcaatac    2580
tacacagggc tgatgtgtca ttttgaacca tcatcttggc agcagtaacg aactggtttc    2640
ctggaccaaa tattttgtca cacttaggaa cagtttctgt tccgtaagcc atagcagcta    2700
ctgcctgggc gcctcctgct agcacgatac acttagcacc aaccttgtgg gcaacgtaga    2760
tgacttctgg ggtaagggta ccatccttct taggtggaga tgcaaaaaca atttctttgc    2820
aaccagcaac tttggcagga cacccagca tcagggaagt ggaaggcaga attgcggttc      2880
caccaggaat atagaggcca actttctcaa taggtcttgc aaaacgagag cagactacac    2940
cagggcaagt ctcaacttgc aacgtctccg ttagttgagc ttcatggaat ttcctgacgt    3000
tatctataga gagatcaatg gctctcttaa cgttatctgg caattgcata agttcctctg    3060
ggaaaggagc ttctaacaca ggtgtcttca aagcgactcc atcaaacttg gcagttagtt    3120 ctaaagggc tttgtcacca ttttgacgaa cattgtcgac aattggtttg actaattcca     3180
taatctgttc cgttttctgg ataggacgac gaagggcatc ttcaatttct tgtgaggagg    3240
ccttagaaac gtcaattttg cacaattcaa tacgaccttc agaagggact tctttaggtt    3300
tggattcttc tttaggttgt tccttggtgt atcctggctt ggcatctcct ttccttctag    3360
tgacctttag ggacttcata tccaggtttc tctccacctc gtccaacgtc acccgtact     3420 tggcacatct aactaatgca aaataaaata agtcagcaca ttcccaggct atatcttcct    3480
tggatttagc ttctgcaagt tcatcagctt cctccctaat tttagcgttc aacaaaactt    3540
cgtcgtcaaa taaccgtttg gtataagaac cttctggagc attgctctta cgatcccaca    3600
aggtggcttc catggctcta agacccttg attggccaaa acaggaagtg cgttccaagt     3660
gacagaaacc aacacctgtt tgttcaacca caaatttcaa gcagtctcca tcacaatcca    3720
attcgatacc cagcaacttt tgagttgctc cagatgtagc acctttatac cacaaaccgt    3780
gacgacgaga ttggtagact ccagtttgtg tccttatagc ctccggaata gacttttgg     3840 acgagtacac caggcccaac gagtaattag aagagtcagc caccaaagta gtgaatagac    3900
catcggggcg gtcagtagtc aaagacgcca acaaaatttc actgacaggg aacttttga    3960 catcttcaga aagttcgtat tcagtagtca attgccgagc atcaataatg gggattatac    4020
cagaagcaac agtggaagtc acatctacca actttgcggt ctcagaaaaa gcataaacag    4080
ttctactacc gccattagtg aaactttca atcgcccag tggagaagaa aaaggcacag      4140
cgatactagc attagcgggc aaggatgcaa ctttatcaac cagggtccta tagataaccc    4200
tagcgcctgg gatcatcctt tggacaactc tttctgccaa atctaggtcc aaaatcactt    4260
cattgatacc attattgtac aacttgagca agttgtcgat cagctcctca aattggtcct    4320
ctgtaacgga tgactcaact tgcacattaa cttgaagctc agtcgattga gtgaacttga    4380
tcaggttgtg cagctggtca gcagcatagg gaaacacggc ttttcctacc aaactcaagg    4440
aattatcaaa ctctgcaaca cttgcgtatg caggtagcaa gggaaatgtc atacttgaag    4500
```

```
tcggacagtg agtgtagtct tgagaaattc tgaagccgta ttttattat cagtgagtca    4560
gtcatcagga gatcctctac gccggacgca tcgtggccgg catcaccggc gccacaggtg    4620
cggttgctgg cgcctatatc gccgacatca ccgatgggga agatcgggct cgccacttcg    4680
ggctcatgag cgcttgtttc ggcgtgggta tggtggcagg ccccgtggcc ggggactgt    4740
tgggcgccat ctccttgcat gcaccattcc ttgcggcggc ggtgctcaac ggcctcaacc    4800
tactactggg ctgcttccta atgcaggagt cgcataaggg agagcgtcga gtatctatga    4860
ttggaagtat gggaatggtg atacccgcat tcttcagtgt cttgaggtct cctatcagat    4920
tatgcccaac taaagcaacc ggaggaggag atttcatggt aaatttctct gacttttggt    4980
catcagtaga ctcgaactgt gagactatct cggttatgac agcagaaatg tccttcttgg    5040
agacagtaaa tgaagtccca ccaataaaga aatccttgtt atcaggaaca aacttcttgt    5100
ttcgaacttt ttcggtgcct tgaactataa aatgtagagt ggatatgtcg ggtaggaatg    5160
gagcgggcaa atgcttacct tctggacctt caagaggtat gtagggtttg tagatactga    5220
tgccaacttc agtgacaacg ttgctatttc gttcaaacca ttccgaatcc agagaaatca    5280
aagttgtttg tctactattg atccaagcca gtgcggtctt gaaactgaca atagtgtgct    5340
cgtgttttga ggtcatcttt gtatgaataa atctagtctt tgatctaaat aatcttgacg    5400
agccaaggcg ataaataccc aaatctaaaa ctcttttaaa acgttaaaag acaagtatg    5460
tctgcctgta ttaaacccca aatcagctcg tagtctgatc ctcatcaact tgagggcac    5520
tatcttgttt tagagaaatt tgcggagatg cgatatcgag aaaaaggtac gctgatttta    5580
aacgtgaaat ttatctcaag atctctgcct cgcgcgtttc ggtgatgacg gtgaaaacct    5640
ctgacacatg cagctcccgg agacggtcac agcttgtctg taagcggatg ccgggagcag    5700
acaagcccgt cagggcgcgt cagcgggtgt tggcgggtgt cggggcgcag ccatgaccca    5760
gtcacgtagc gatagcggag tgtatactgg cttaactatg cggcatcaga gcagattgta    5820
ctgagagtgc accatatgcg gtgtgaaata ccgcacagat gcgtaaggag aaaataccgc    5880
atcaggcgct cttccgcttc ctcgctcact gactcgctgc gctcggtcgt tcggctgcgg    5940
cgagcggtat cagctcactc aaaggcggta atacggttat ccacagaatc aggggataac    6000
gcaggaaaga acatgtgagc aaaaggccag caaaaggcca ggaaccgtaa aaaggccgcg    6060
ttgctggcgt ttttccatag gctccgcccc cctgacgagc atcacaaaaa tcgacgctca    6120
agtcagaggt ggcgaaaccc gacaggacta taaagatacc aggcgtttcc ccctggaagc    6180
tccctcgtgc gctctcctgt tccgaccctg ccgcttaccg gatacctgtc cgcctttctc    6240
ccttcgggaa gcgtggcgct ttctcaatgc tcacgctgta ggtatctcag ttcggtgtag    6300
gtcgttcgct ccaagctggg ctgtgtgcac gaaccccccg ttcagcccga ccgctgcgcc    6360
ttatccggta actatcgtct tgagtccaac ccggtaagac acgacttatc gccactggca    6420
gcagccactg gtaacaggat tagcagagcg aggtatgtag cggtgctac agagttcttg    6480
aagtggtggc ctaactacgg ctacactaga aggacagtat ttggtatctg cgctctgctg    6540
aagccagtta ccttcggaaa aagagttggt agctcttgat ccggcaaaca aaccaccgct    6600
ggtagcggtg gtttttttgt ttgcaagcag cagattacgc gcagaaaaaa aggatctcaa    6660
gaagatcctt tgatcttttc tacggggtct gacgctcagt ggaacgaaaa ctcacgttaa    6720
gggattttgg tcatgagatt atcaaaaagg atcttcacct agatcctttt aaattaaaaa    6780
tgaagtttta aatcaatcta agtatatat gagtaaactt ggtctgacag ttaccaatgc    6840
ttaatcagtg aggcacctat ctcagcgatc tgtctatttc gttcatccat agttgcctga    6900
```

```
ctccccgtcg tgtagataac tacgatacgg gagggcttac catctggccc cagtgctgca        6960
atgataccgc gagacccacg ctcaccggct ccagatttat cagcaataaa ccagccagcc        7020
ggaagggccg agcgcagaag tggtcctgca actttatccg cctccatcca gtctattaat        7080
tgttgccggg aagctagagt aagtagttcg ccagttaata gtttgcgcaa cgttgttgcc        7140
attgctgcag gcatcgtggt gtcacgctcg tcgtttggta tggcttcatt cagctccggt        7200
tcccaacgat caaggcgagt tacatgatcc cccatgttgt gcaaaaaagc ggttagctcc        7260
ttcggtcctc cgatcgttgt cagaagtaag ttggccgcag tgttatcact catggttatg        7320
gcagcactgc ataattctct tactgtcatg ccatccgtaa gatgcttttc tgtgactggt        7380
gagtactcaa ccaagtcatt ctgagaatag tgtatgcggc gaccgagttg ctcttgcccg        7440
gcgtcaacac gggataatac cgcgccacat agcagaactt taaaagtgct catcattgga        7500
aaacgttctt cggggcgaaa actctcaagg atcttaccgc tgttgagatc cagttcgatg        7560
taacccactc gtgcacccaa ctgatcttca gcatctttta ctttcaccag cgtttctggg        7620
tgagcaaaaa caggaaggca aaatgccgca aaaagggaa taaggcgac acggaaatgt        7680 tgaatactca tactcttcct ttttcaatat tattgaagca tttatcaggg ttattgtctc        7740
atgagcggat acatatttga atgtatttag aaaaataaac aaataggggt tccgcgcaca        7800
tttccccgaa aagtgccacc tgacgtctaa gaaaccatta ttatcatgac attaacctat        7860
aaaaataggc gtatcacgag gccctttcgt cttcaagaat taattctcat gtttgacagc        7920
ttatcatcga taagctgact catgttggta ttgtgaaata gacgcagatc gggaacactg        7980
aaaaataaca gttattattc g                                                  8001

<210> SEQ ID NO 3
<211> LENGTH: 8185
<212> TYPE: DNA
<213> ORGANISM: Artificial
<220> FEATURE:
<223> OTHER INFORMATION: Synthetic

<400> SEQUENCE: 3
agatctaaca tccaaagacg aaaggttgaa tgaaaccttt ttgccatccg acatccacag          60
gtccattctc acacataagt gccaaacgca acaggagggg atacactagc agcagaccgt         120
tgcaaacgca ggacctccac tcctcttctc ctcaacaccc acttttgcca tcgaaaaacc         180
agcccagtta ttgggcttga ttggagctcg ctcattccaa ttccttctat taggctacta         240
acaccatgac tttattagcc tgtctatcct ggcccccctg gcgaggttca tgtttgttta         300
tttccgaatg caacaagctc cgcattacac ccgaacatca ctccagatga gggctttctg         360
agtgtggggt caaatagttt catgttcccc aaatggccca aaactgacag tttaaacgct         420
gtcttggaac ctaatatgac aaaagcgtga tctcatccaa gatgaactaa gtttggttcg         480
ttgaaatgct aacggccagt tggtcaaaaa gaaacttcca aaagtcgcca taccgtttgt         540
cttgtttggt attgattgac gaatgctcaa aaataatctc attaatgctt agcgcagtct         600
ctctatcgct tctgaacccc ggtgcacctg tgccgaaacg caaatgggga acacccgct         660 ttttggatga ttatgcattg tctccacatt gtatgcttcc aagattctgg tgggaatact         720
gctgatagcc taacgttcat gatcaaaatt taactgttct aaccctact tgacagcaat         780 atataaacag aaggaagctg ccctgtctta aaccttttt tttatcatca ttattagctt         840
actttcataa ttgcgactgg ttccaattga caagcttttg attttaacga ctttaacga         900
```

```
caacttgaga agatcaaaaa acaactaatt attcgaagga tccaaacgat gagatttcct    960
tcaattttta ctgcagtttt attcgcagca tcctccgcat tagctgctcc agtcaacact   1020
acaacagaag atgaaacggc acaaattccg gctgaagctg tcatcggtta ctcagattta   1080
gaagggatt tcgatgttgc tgttttgcca ttttccaaca gcacaaataa cgggttattg    1140
tttataaata ctactattgc cagcattgct gctaaagaag aagggtatc tctcgagaaa    1200
agagaggagt acgtgggcct gtctgcaaac cagtgtgccg tgccagccaa ggacagggtg   1260
gactgcggct acccccatgt caccccccaag gagtgcaaca accggggctg ctgctttgac  1320
tccaggatcc ctggagtgcc ttggtgtttc aagcccctgc aggaagcaga atgcaccttc   1380
tgagaattcc ctagggcggc cgcgaattaa ttcgccttag acatgactgt tcctcagttc   1440
aagttgggca cttacgagaa gaccggtctt gctagattct aatcaagagg atgtcagaat   1500
gccatttgcc tgagagatgc aggcttcatt tttgatactt ttttatttgt aacctatata   1560
gtataggatt tttttgtca ttttgtttct tctcgtacga gcttgctcct gatcagccta    1620
tctcgcagct gatgaatatc ttgtggtagg ggtttgggaa atcattcga gtttgatgtt    1680
tttcttggta tttcccactc ctcttcagag tacagaagat taagtgagaa gttcgtttgt   1740
gcaagcttat cgataagctt taatgcggta gtttatcaca gttaaattgc taacgcagtc   1800
aggcaccgtg tatgaaatct aacaatgcgc tcatcgtcat cctcggcacc gtcaccctgg   1860
atgctgtagg cataggcttg gttatgccgg tactgccggg cctcttgcgg gatatcgtcc   1920
attccgacag catcgccagt cactatggcg tgctgctagc gctatatgcg ttgatgcaat   1980
ttctatgcgc acccgttctc ggagcactgt ccgaccgctt tggccgccgc ccagtcctgc   2040
tcgcttcgct acttggagcc actatcgact acgcgatcat ggcgaccaca cccgtcctgt   2100
ggatctatcg aatctaaatg taagttaaaa tctctaaata attaaataag tcccagtttc   2160
tccatacgaa ccttaacagc attgcggtga gcatctagac cttcaacagc agccagatcc   2220
atcactgctt ggccaatatg tttcagtccc tcaggagtta cgtcttgtga agtgatgaac   2280
ttctggaagg ttgcagtgtt aactccgctg tattgacggg catatccgta cgttggcaaa   2340
gtgtggttgg taccggagga gtaatctcca caactctctg gagagtaggc accaacaaac   2400
acagatccag cgtgttgtac ttgatcaaca taagaagaag cattctcgat ttgcaggatc   2460
aagtgttcag gagcgtactg attggacatt tccaaagcct gctcgtaggt tgcaaccgat   2520
agggttgtag agtgtgcaat acacttgcgt acaatttcaa cccttggcaa ctgcacagct   2580
tggttgtgaa cagcatcttc aattctggca agctccttgt ctgtcatatc gacagccaac   2640
agaatcacct gggaatcaat accatgttca gcttgagaca gaaggtctga ggcaacgaaa   2700
tctggatcag cgtatttatc agcaataact agaacttcag aaggcccagc aggcatgtca   2760
atactacaca gggctgatgt gtcattttga accatcatct tggcagcagt aacgaactgg   2820
tttcctggac caaatatttt gtcacactta ggaacagttt ctgttccgta agccatagca   2880
gctactgcct gggcgcctcc tgctagcacg atacacttag caccaacctt gtgggcaacg   2940
tagatgactt ctggggtaag ggtaccatcc ttcttaggtg gagatgcaaa acaatttct    3000
ttgcaaccag caactttggc aggaacaccc agcatcaggg aagtggaagg cagaattgcg   3060
gttccaccag gaatatagag gccaactttc tcaataggtc ttgcaaaacg agagcagact   3120
acaccagggc aagtctcaac ttgcaacgtc tccgttagtt gagcttcatg gaatttcctg   3180
acgttatcta tagagagatc aatggctctc ttaacgttat ctggcaattg cataagttcc   3240
tctgggaaag gagcttctaa cacaggtgtc ttcaaagcga ctccatcaaa cttggcagtt   3300
```

```
agttctaaaa gggctttgtc accattttga cgaacattgt cgacaattgg tttgactaat    3360
tccataatct gttccgtttt ctggatagga cgacgaaggg catcttcaat ttcttgtgag    3420
gaggccttag aaacgtcaat tttgcacaat tcaatacgac cttcagaagg gacttcttta    3480
ggtttggatt cttctttagg ttgttccttg gtgtatcctg gcttggcatc tcctttcctt    3540
ctagtgacct ttagggactt catatccagg tttctctcca cctcgtccaa cgtcacaccg    3600
tacttggcac atctaactaa tgcaaaataa aataagtcag cacattccca ggctatatct    3660
tccttggatt tagcttctgc aagttcatca gcttcctccc taattttagc gttcaacaaa    3720
acttcgtcgt caaataaccg tttggtataa gaaccttctg gagcattgct cttacgatcc    3780
cacaaggtgg cttccatggc tctaagaccc tttgattggc caaaacagga agtgcgttcc    3840
aagtgacaga accaacacc tgtttgttca accacaaatt tcaagcagtc tccatcacaa     3900
tccaattcga tacccagcaa cttttgagtt gctccagatg tagcaccttt ataccacaaa    3960
ccgtgacgac gagattggta gactccagtt tgtgtcctta tagcctccgg aatagacttt    4020
ttggacgagt acaccaggcc caacgagtaa ttagaagagt cagccaccaa agtagtgaat    4080
agaccatcgg ggcggtcagt agtcaaagac gccaacaaaa tttcactgac agggaacttt    4140
ttgacatctt cagaaagttc gtattcagta gtcaattgcc gagcatcaat aatggggatt    4200
ataccagaag caacagtgga agtcacatct accaactttg cggtctcaga aaaagcataa    4260
acagttctac taccgccatt agtgaaactt tcaaatcgc ccagtggaga agaaaaaggc     4320
acagcgatac tagcattagc gggcaaggat gcaactttat caaccagggt cctatagata    4380
accctagcgc ctgggatcat cctttggaca actctttctg ccaaatctag gtccaaaatc    4440
acttcattga taccattatt gtacaacttg agcaagttgt cgatcagctc ctcaaattgg    4500
tcctctgtaa cggatgactc aacttgcaca ttaacttgaa gctcagtcga ttgagtgaac    4560
ttgatcaggt tgtgcagctg gtcagcagca tagggaaaca cggcttttcc taccaaactc    4620
aaggaattat caaactctgc aacacttgcg tatgcaggta gcaagggaaa tgtcatactt    4680
gaagtcggac agtgagtgta gtcttgagaa attctgaagc cgtatttta ttatcagtga     4740
gtcagtcatc aggagatcct ctacgccgga cgcatcgtgg ccggcatcac cggcgccaca    4800
ggtgcggttg ctggcgccta tatcgccgac atcaccgatg gggaagatcg ggctcgccac    4860
ttcgggctca tgagcgcttg tttcggcgtg gtatggtgg caggccccgt ggccggggga     4920
ctgttgggcg ccatctcctt gcatgcacca ttccttgcgg cggcggtgct caacggcctc    4980
aacctactac tgggctgctt cctaatgcag gagtcgcata agggagagcg tcgagtatct    5040
atgattggaa gtatgggaat ggtgataccc gcattcttca gtgtcttgag gtctcctatc    5100
agattatgcc caactaaagc aaccggagga ggagatttca tggtaaattt ctctgacttt    5160
tggtcatcag tagactcgaa ctgtgagact atctcggtta tgacagcaga aatgtccttc    5220
ttggagacag taaatgaagt cccaccaata aagaaatcct tgttatcagg aacaaacttc    5280
ttgtttcgaa cttttcggt gccttgaact ataaaatgta gagtggatat gtcgggtagg     5340
aatggagcgg gcaaatgctt accttctgga ccttcaagag gtatgtaggg tttgtagata    5400
ctgatgccaa cttcagtgac aacgttgcta tttcgttcaa accattccga atccagagaa    5460
atcaaagttg tttgtctact attgatccaa gccagtgcgg tcttgaaact gacaatagtg    5520
tgctcgtgtt ttgaggtcat cttttgtatga ataaatctag tctttgatct aaataatctt   5580
gacgagccaa ggcgataaat acccaaatct aaaactcttt taaaacgtta aaaggacaag    5640
```

```
tatgtctgcc tgtattaaac cccaaatcag ctcgtagtct gatcctcatc aacttgaggg    5700
gcactatctt gttttagaga aatttgcgga gatgcgatat cgagaaaaag gtacgctgat    5760
tttaaacgtg aaatttatct caagatctct gcctcgcgcg tttcggtgat gacggtgaaa    5820
acctctgaca catgcagctc ccggagacgg tcacagcttg tctgtaagcg gatgccggga    5880
gcagacaagc ccgtcagggc gcgtcagcgg gtgttggcgg gtgtcggggc gcagccatga    5940
cccagtcacg tagcgatagc ggagtgtata ctggcttaac tatgcggcat cagagcagat    6000
tgtactgaga gtgcaccata tgcggtgtga ataccgcac agatgcgtaa ggagaaaata    6060
ccgcatcagg cgctcttccg cttcctcgct cactgactcg ctgcgctcgg tcgttcggct    6120
gcggcgagcg gtatcagctc actcaaaggc ggtaatacgg ttatccacag aatcagggga    6180
taacgcagga aagaacatgt gagcaaaagg ccagcaaaag gccaggaacc gtaaaaaggc    6240
cgcgttgctg gcgtttttcc ataggctccg cccccctgac gagcatcaca aaaatcgacg    6300
ctcaagtcag aggtggcgaa acccgacagg actataaaga taccaggcgt ttccccctgg    6360
aagctccctc gtgcgctctc ctgttccgac cctgccgctt accggatacc tgtccgcctt    6420
tctcccttcg ggaagcgtgg cgctttctca atgctcacgc tgtaggtatc tcagttcggt    6480
gtaggtcgtt cgctccaagc tgggctgtgt gcacgaaccc cccgttcagc ccgaccgctg    6540
cgccttatcc ggtaactatc gtcttgagtc caacccggta agacacgact tatcgccact    6600
ggcagcagcc actggtaaca ggattagcag agcgaggtat gtaggcggtg ctacagagtt    6660
cttgaagtgg tggcctaact acggctacac tagaaggaca gtatttggta tctgcgctct    6720
gctgaagcca gttaccttcg gaaaaagagt tggtagctct tgatccggca aacaaaccac    6780
cgctggtagc ggtggttttt tgtttgcaa gcagcagatt acgcgcagaa aaaaaggatc    6840
tcaagaagat cctttgatct tttctacggg gtctgacgct cagtggaacg aaaactcacg    6900
ttaagggatt ttggtcatga gattatcaaa aaggatcttc acctagatcc ttttaaatta    6960
aaaatgaagt tttaaatcaa tctaaagtat atatgagtaa acttggtctg acagttacca    7020
atgcttaatc agtgaggcac ctatctcagc gatctgtcta tttcgttcat ccatagttgc    7080
ctgactcccc gtcgtgtaga taactacgat acgggagggc ttaccatctg gccccagtgc    7140
tgcaatgata ccgcgagacc cacgctcacc ggctccagat ttatcagcaa taaaccagcc    7200
agccggaagg gccgagcgca gaagtggtcc tgcaacttta tccgcctcca tccagtctat    7260
taattgttgc cgggaagcta gagtaagtag ttcgccagtt aatagtttgc gcaacgttgt    7320
tgccattgct gcaggcatcg tggtgtcacg ctcgtcgttt ggtatggctt cattcagctc    7380
cggttcccaa cgatcaaggc gagttacatg atccccatg ttgtgcaaaa aagcggttag    7440
ctccttcggt cctccgatcg ttgtcagaag taagttggcc gcagtgttat cactcatggt    7500
tatggcagca ctgcataatt ctcttactgt catgccatcc gtaagatgct tttctgtgac    7560
tggtgagtac tcaaccaagt cattctgaga atagtgtatg cggcgaccga gttgctcttg    7620
cccggcgtca acacgggata ataccgcgcc acatagcaga actttaaaag tgctcatcat    7680
tggaaaacgt tcttcgggc gaaaactctc aaggatctta ccgctgttga gatccagttc    7740
gatgtaaccc actcgtgcac ccaactgatc ttcagcatct tttactttca ccagcgtttc    7800
tgggtgagca aaaacaggaa ggcaaaatgc cgcaaaaaag ggaataaggg cgacacggaa    7860
atgttgaata ctcatactct tccttttca atattattga agcatttatc agggttattg    7920
tctcatgagc ggatacatat ttgaatgtat ttagaaaaat aaacaaatag gggttccgcg    7980
cacatttccc cgaaaagtgc cacctgacgt ctaagaaacc attattatca tgacattaac    8040
```

```
ctataaaaat aggcgtatca cgaggccctt tcgtcttcaa gaattaattc tcatgtttga    8100
cagcttatca tcgataagct gactcatgtt ggtattgtga aatagacgca gatcgggaac    8160
actgaaaaat aacagttatt attcg                                          8185

<210> SEQ ID NO 4
<211> LENGTH: 8227
<212> TYPE: DNA
<213> ORGANISM: Artificial
<220> FEATURE:
<223> OTHER INFORMATION: synthetic

<400> SEQUENCE: 4
agatctaaca tccaaagacg aaaggttgaa tgaaaccttt ttgccatccg acatccacag      60
gtccattctc acacataagt gccaaacgca acaggagggg atacactagc agcagaccgt     120
tgcaaacgca ggacctccac tcctcttctc ctcaacaccc acttttgcca tcgaaaaacc     180
agcccagtta ttgggcttga ttggagctcg ctcattccaa ttccttctat taggctacta     240
acaccatgac tttattagcc tgtctatcct ggcccccctg cgaggttca tgtttgttta      300 tttccgaatg caacaagctc cgcattacac ccgaacatca ctccagatga gggctttctg     360
agtgtgtggt caaatagttt catgttcccc aaatggccca aaactgacag ttttaaacgct    420 gtcttggaac ctaatatgac aaaagcgtga tctcatccaa gatgaactaa gtttggttcg     480
ttgaaatgct aacggccagt tggtcaaaaa gaaacttcca aaagtcgcca taccgttttgt    540 cttgtttggt attgattgac gaatgctcaa aaataatctc attaatgctt agcgcagtct     600
ctctatcgct tctgaacccc ggtgcacctg tgccgaaacg caaatgggga aacacccgct     660
ttttggatga ttatgcattg tctccacatt gtatgcttcc aagattctgg tgggaatact     720
gctgatagcc taacgttcat gatcaaaatt taactgttct aacccctact tgacagcaat     780
atataaacag aaggaagctg ccctgtctta aacctttttt tttatcatca ttattagctt     840
actttcataa ttgcgactgg ttccaattga caagcttttg attttaacga cttttaacga     900
caacttgaga agatcaaaaa acaactaatt attcgaagga tccaaacgat gagatttcct     960 tcaatttta ctgcagtttt attcgcagca tcctccgcat tagctgctcc agtcaacact     1020
acaacagaag atgaaacggc acaaattccg gctgaagctg tcatcggtta ctcagattta   1080
gaaggggatt tcgatgttgc tgttttgcca ttttccaaca gcacaaataa cgggttattg   1140
tttataaata ctactattgc cagcattgct gctaaagaag aagggggtatc tctcgagaaa   1200 agaatgctgg ggctggtcct ggccttgctg tcctccagct ctgctgagga gtacgtgggc   1260
ctgtctgcaa accagtgtgc cgtgccagcc aaggacaggg tggactgcgg ctaccccat    1320 gtcaccccca aggagtgcaa caaccggggc tgctgctttg actccaggat ccctggagtg   1380
ccttggtgtt tcaagcccct gcaggaagca gaatgcacct tctgagaatt ccctagggcg   1440
gccgcgaatt aattcgcctt agacatgact gttcctcagt tcaagttggg cacttacgag   1500
aagaccggtc ttgctagatt ctaatcaaga ggatgtcaga atgccatttg cctgagagat   1560
gcaggcttca tttttgatac ttttttattt gtaacctata tagtatagga ttttttttgt   1620
cattttgttt cttctcgtac gagcttgctc ctgatcagcc tatctcgcag ctgatgaata   1680
tcttgtggta gggtttggg aaaatcattc gagtttgatg ttttttcttgg tatttcccac   1740 tcctcttcag agtacagaag attaagtgag aagttcgttt gtgcaagctt atcgataagc   1800
tttaatgcgg tagtttatca cagttaaatt gctaacgcag tcaggcaccg tgtatgaaat   1860
```

```
ctaacaatgc gctcatcgtc atcctcggca ccgtcaccct ggatgctgta ggcataggct    1920
tggttatgcc ggtactgccg ggcctcttgc gggatatcgt ccattccgac agcatcgcca    1980
gtcactatgg cgtgctgcta gcgctatatg cgttgatgca atttctatgc gcacccgttc    2040
tcggagcact gtccgaccgc tttggccgcc gcccagtcct gctcgcttcg ctacttggag    2100
ccactatcga ctacgcgatc atggcgacca cacccgtcct gtggatctat cgaatctaaa    2160
tgtaagttaa aatctctaaa taattaaata agtcccagtt tctccatacg aaccttaaca    2220
gcattgcggt gagcatctag accttcaaca gcagccagat ccatcactgc ttggccaata    2280
tgtttcagtc cctcaggagt tacgtcttgt gaagtgatga acttctggaa ggttgcagtg    2340
ttaactccgc tgtattgacg ggcatatccg tacgttggca aagtgtggtt ggtaccggag    2400
gagtaatctc cacaactctc tggagagtag gcaccaacaa acacagatcc agcgtgttgt    2460
acttgatcaa cataagaaga agcattctcg atttgcagga tcaagtgttc aggagcgtac    2520
tgattggaca tttccaaagc ctgctcgtag gttgcaaccg atagggttgt agagtgtgca    2580
atacacttgc gtacaatttc aaccccttggc aactgcacag cttggttgtg aacagcatct    2640
tcaattctgg caagctcctt gtctgtcata tcgacagcca acagaatcac ctgggaatca    2700
ataccatgtt cagcttgaga cagaaggtct gaggcaacga aatctggatc agcgtattta    2760
tcagcaataa ctagaacttc agaaggccca gcaggcatgt caatactaca cagggctgat    2820
gtgtcatttt gaaccatcat cttggcagca gtaacgaact ggtttcctgg accaaatatt    2880
ttgtcacact taggaacagt ttctgttccg taagccatag cagctactgc ctgggcgcct    2940
cctgctagca cgatacactt agcaccaacc ttgtgggcaa cgtagatgac ttctggggta    3000
agggtaccat ccttcttagg tggagatgca aaaacaattt ctttgcaacc agcaactttg    3060
gcaggaacac ccagcatcag ggaagtggaa ggcagaattg cggttccacc aggaatatag    3120
aggccaactt tctcaatagg tcttgcaaaa cgagagcaga ctacaccagg gcaagtctca    3180
acttgcaacg tctccgttag ttgagcttca tggaatttcc tgacgttatc tatagagaga    3240
tcaatggctc tcttaacgtt atctggcaat tgcataagtt cctctgggaa aggagcttct    3300
aacacaggtg tcttcaaagc gactccatca aacttggcag ttagttctaa aagggctttg    3360
tcaccatttt gacgaacatt gtcgacaatt ggtttgacta attccataat ctgttccgtt    3420
ttctggatag gacgacgaag ggcatcttca atttcttgtg aggaggcctt agaaacgtca    3480
attttgcaca attcaatacg accttcagaa gggacttctt taggtttgga ttcttcttta    3540
ggttgttcct tggtgtatcc tggcttgca tctccttttcc ttctagtgac ctttagggac    3600
ttcatatcca ggtttctctc cacctcgtcc aacgtcacac cgtacttggc acatctaact    3660
aatgcaaaat aaaataagtc agcacattcc caggctatat cttccttgga tttagcttct    3720
gcaagttcat cagcttcctc cctaattta gcgttcaaca aaacttcgtc gtcaaataac    3780
cgtttggtat aagaaccttc tggagcattg ctcttacgat cccacaaggt ggcttccatg    3840
gctctaagac cctttgattg gccaaaacag gaagtgcgtt ccaagtgaca gaaaccaaca    3900
cctgtttgtt caaccacaaa tttcaagcag tctccatcac aatccaattc gatcccagc    3960 aacttttgag ttgctccaga tgtagcacct ttataccaca aaccgtgacg acgagattgg    4020
tagactccga tttgtgtcct tatagcctcc ggaatagact ttttggacga gtacaccagg    4080
cccaacgagt aattagaaga gtcagccacc aaagtagtga atagaccatc ggggcggtca    4140
gtagtcaaag acgccaacaa aatttccactg acagggaact ttttgacatc ttcagaaagt    4200
tcgtattcag tagtcaattg ccgagcatca ataatgggga ttataccaga agcaacagtg    4260
```

-continued

```
gaagtcacat ctaccaactt tgcggtctca gaaaaagcat aaacagttct actaccgcca    4320
ttagtgaaac ttttcaaatc gcccagtgga gaagaaaaag gcacagcgat actagcatta    4380
gcgggcaagg atgcaacttt atcaaccagg gtcctataga taaccctagc gcctgggatc    4440
atcctttgga caactctttc tgccaaatct aggtccaaaa tcacttcatt gataccatta    4500
ttgtacaact tgagcaagtt gtcgatcagc tcctcaaatt ggtcctctgt aacggatgac    4560
tcaacttgca cattaacttg aagctcagtc gattgagtga acttgatcag gttgtgcagc    4620
tggtcagcag catagggaaa cacggctttt cctaccaaac tcaaggaatt atcaaactct    4680
gcaacacttg cgtatgcagg tagcaaggga aatgtcatac ttgaagtcgg acagtgagtg    4740
tagtcttgag aaattctgaa gccgtatttt tattatcagt gagtcagtca tcaggagatc    4800
ctctacgccg gacgcatcgt ggccggcatc accggcgcca caggtgcggt tgctggcgcc    4860
tatatcgccg acatcaccga tggggaagat cgggctcgcc acttcgggct catgagcgct    4920
tgtttcggcg tgggtatggt ggcaggcccc gtggccgggg gactgttggg cgccatctcc    4980
ttgcatgcac cattccttgc ggcggcggtg ctcaacggcc tcaacctact actgggctgc    5040
ttcctaatgc aggagtcgca aagggagag cgtcgagtat ctatgattgg aagtatggga    5100
atggtgatac ccgcattctt cagtgtcttg aggtctccta tcagattatg cccaactaaa    5160
gcaaccggag gaggagattt catggtaaat ttctctgact tttggtcatc agtagactcg    5220
aactgtgaga ctatctcggt tatgacagca gaaatgtcct tcttggagac agtaaatgaa    5280
gtcccaccaa taaagaaatc cttgttatca ggaacaaact tcttgtttcg aacttttcg    5340
gtgccttgaa ctataaaatg tagagtggat atgtcgggta ggaatggagc gggcaaatgc    5400
ttaccttctg gaccttcaag aggtatgtag ggtttgtaga tactgatgcc aacttcagtg    5460
acaacgttgc tatttcgttc aaaccattcc gaatccagag aaatcaaagt tgtttgtcta    5520
ctattgatcc aagccagtgc ggtcttgaaa ctgacaatag tgtgctcgtg ttttgaggtc    5580
atctttgtat gaataaatct agtctttgat ctaaataatc ttgacgagcc aaggcgataa    5640
atacccaaat ctaaaactct tttaaaacgt taaaaggaca agtatgtctg cctgtattaa    5700
accccaaatc agctcgtagt ctgatcctca tcaacttgag gggcactatc ttgttttaga    5760
gaaatttgcg gagatgcgat atcgagaaaa aggtacgctg attttaaacg tgaaatttat    5820
ctcaagatct ctgcctcgcg cgtttcggtg atgacggtga aaacctctga cacatgcagc    5880
tcccggagac ggtcacagct tgtctgtaag cggatgccgg gagcagacaa gcccgtcagg    5940
gcgcgtcagc gggtgttggc gggtgtcggg gcgcagccat gacccagtca cgtagcgata    6000
gcggagtgta tactggctta actatgcggc atcagagcag attgtactga gagtgcacca    6060
tatgcggtgt gaaataccgc acagatgcgt aaggagaaaa taccgcatca ggcgctcttc    6120
cgcttcctcg ctcactgact cgctgcgctc ggtcgttcgg ctgcggcgag cggtatcagc    6180
tcactcaaag gcggtaatac ggttatccac agaatcaggg ataacgcag aaagaacat    6240
gtgagcaaaa ggccagcaaa aggccaggaa ccgtaaaaag gccgcgttgc tggcgttttt    6300
ccataggctc cgcccccctg acgagcatca aaaaatcga cgctcaagtc agaggtggcg    6360
aaacccgaca ggactataaa gataccaggc gtttccccct ggaagctccc tcgtgcgctc    6420
tcctgttccg accctgccgc ttaccggata cctgtccgcc tttctccctt cgggaagcgt    6480
ggcgctttct caatgctcac gctgtaggta tctcagttcg gtgtaggtcg ttcgctccaa    6540
gctgggctgt gtgcacgaac cccccgttca gcccgaccgc tgcgccttat ccggtaacta    6600
```

| | |
|---|---:|
| tcgtcttgag tccaacccgg taagacacga cttatcgcca ctggcagcag ccactggtaa | 6660 |
| caggattagc agagcgaggt atgtaggcgg tgctacagag ttcttgaagt ggtggcctaa | 6720 |
| ctacggctac actagaagga cagtatttgg tatctgcgct ctgctgaagc cagttacctt | 6780 |
| cggaaaaaga gttggtagct cttgatccgg caaacaaacc accgctggta gcggtggttt | 6840 |
| ttttgtttgc aagcagcaga ttacgcgcag aaaaaaagga tctcaagaag atcctttgat | 6900 |
| cttttctacg gggtctgacg ctcagtggaa cgaaaactca cgttaaggga ttttggtcat | 6960 |
| gagattatca aaaaggatct cacctagatc cttttaaatt aaaaatgaag ttttaaatc | 7020 |
| aatctaaagt atatatgagt aaacttggtc tgacagttac caatgcttaa tcagtgaggc | 7080 |
| acctatctca gcgatctgtc tatttcgttc atccatagtt gcctgactcc ccgtcgtgta | 7140 |
| gataactacg atacgggagg gcttaccatc tggccccagt gctgcaatga taccgcgaga | 7200 |
| cccacgctca ccggctccag atttatcagc aataaaccag ccagccggaa gggccgagcg | 7260 |
| cagaagtggt cctgcaactt tatccgcctc catccagtct attaattgtt gccgggaagc | 7320 |
| tagagtaagt agttcgccag ttaatagttt gcgcaacgtt gttgccattg ctgcaggcat | 7380 |
| cgtggtgtca cgctcgtcgt ttggtatggc ttcattcagc tccggttccc aacgatcaag | 7440 |
| gcgagttaca tgatccccca tgttgtgcaa aaaagcggtt agctccttcg gtcctccgat | 7500 |
| cgttgtcaga agtaagttgg ccgcagtgtt atcactcatg gttatggcag cactgcataa | 7560 |
| ttctcttact gtcatgccat ccgtaagatg cttttctgtg actggtgagt actcaaccaa | 7620 |
| gtcattctga gaatagtgta tgcggcgacc gagttgctct tgcccggcgt caacacggga | 7680 |
| taataccgcg ccacatagca gaactttaaa agtgctcatc attggaaaac gttcttcggg | 7740 |
| gcgaaaactc tcaaggatct taccgctgtt gagatccagt tcgatgtaac ccactcgtgc | 7800 |
| acccaactga tcttcagcat cttttacttt caccagcgtt tctgggtgag caaaaacagg | 7860 |
| aaggcaaaat gccgcaaaaa agggaataag ggcgacacgg aaatgttgaa tactcatact | 7920 |
| cttcctttttt caatattatt gaagcattta tcagggttat tgtctcatga gcggatacat | 7980 |
| atttgaatgt atttagaaaa ataaacaaat aggggttccg cgcacatttc cccgaaaagt | 8040 |
| gccacctgac gtctaagaaa ccattattat catgacatta acctataaaa ataggcgtat | 8100 |
| cacgaggccc tttcgtcttc aagaattaat tctcatgttt gacagcttat catcgataag | 8160 |
| ctgactcatg ttggtattgt gaaatagacg cagatcggga acactgaaaa ataacagtta | 8220 |
| ttattcg | 8227 |

<210> SEQ ID NO 5
<211> LENGTH: 7818
<212> TYPE: DNA
<213> ORGANISM: Artificial
<220> FEATURE:
<223> OTHER INFORMATION: synthetic

<400> SEQUENCE: 5

| | |
|---|---:|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggccccctg gcgaggttca tgtttgttta | 300 |
| tttccgaatg caacaagctc cgcattacac ccgaacatca ctccagatga gggctttctg | 360 |
| agtgtggggt caaatagttt catgttcccc aaatggccca aaactgacag tttaaacgct | 420 |

```
gtcttggaac ctaatatgac aaaagcgtga tctcatccaa gatgaactaa gtttggttcg      480
ttgaaatgct aacggccagt tggtcaaaaa gaaacttcca aaagtcgcca taccgtttgt      540
cttgtttggt attgattgac gaatgctcaa aaataatctc attaatgctt agcgcagtct      600
ctctatcgct tctgaacccc ggtgcacctg tgccgaaacg caaatgggga aacacccgct      660
ttttggatga ttatgcattg tctccacatt gtatgcttcc aagattctgg tgggaatact      720
gctgatagcc taacgttcat gatcaaaatt taactgttct aaccccctact tgacagcaat      780 atataaacag aaggaagctg ccctgtctta aaccttttt tttatcatca ttattagctt      840
actttcataa ttgcgactgg ttccaattga caagcttttg attttaacga cttttaacga      900
caacttgaga agatcaaaaa acaactaatt attcgaagga tccaaacgat gagatttcct      960
tcaattttta ctgcagtttt attcgcagca tcctccgcat tagctgctct cgagtagaat     1020
tccctagggc ggccgcgaat taattcgcct tagacatgac tgttcctcag ttcaagttgg     1080
gcacttacga gaagaccggt cttgctagat tctaatcaag aggatgtcag aatgccattt     1140
gcctgagaga tgcaggcttc attttttgata cttttttatt tgtaacctat atagtatagg     1200 atttttttttg tcattttgtt tcttctcgta cgagcttgct cctgatcagc ctatctcgca     1260
gctgatgaat atcttgtggt aggggtttgg gaaaatcatt cgagtttgat gttttttcttg     1320 gtatttccca ctcctcttca gagtacagaa gattaagtga aagttcgtt tgtgcaagct     1380 tatcgataag ctttaatgcg gtagtttatc acagttaaat tgctaacgca gtcaggcacc     1440
gtgtatgaaa tctaacaatg cgctcatcgt catcctcggc accgtcaccc tggatgctgt     1500
aggcataggc ttggttatgc cggtactgcc gggcctcttg cgggatatcg tccattccga     1560
cagcatcgcc agtcactatg gcgtgctgct agcgctatat gcgttgatgc aatttctatg     1620
cgcacccgtt ctcggagcac tgtccgaccg ctttggccgc cgcccagtcc tgctcgcttc     1680
gctacttgga gccactatcg actacgcgat catggcgacc acacccgtcc tgtggatcta     1740
tcgaatctaa atgtaagtta aaatctctaa ataattaaat aagtcccagt ttctccatac     1800
gaaccttaac agcattgcgg tgagcatcta gaccttcaac agcagccaga tccatcactg     1860
cttggccaat atgtttcagt ccctcaggag ttacgtcttg tgaagtgatg aacttctgga     1920
aggttgcagt gttaactccg ctgtattgac gggcatatcc gtacgttggc aaagtgtggt     1980
tggtaccgga ggagtaatct ccacaactct ctggagagta ggcaccaaca aacacagatc     2040
cagcgtgttg tacttgatca acataagaag aagcattctc gatttgcagg atcaagtgtt     2100
caggagcgta ctgattggac atttccaaag cctgctcgta ggttgcaacc gatagggttg     2160
tagagtgtgc aatacacttg cgtacaattt caacccttgg caactgcaca gcttggttgt     2220
gaacagcatc ttcaattctg gcaagctcct tgtctgtcat atcgacagcc aacagaatca     2280
cctgggaatc aataccatgt tcagcttgag acagaaggtc tgaggcaacg aaatctggat     2340
cagcgtattt atcagcaata actagaactt cagaaggccc agcaggcatg tcaatactac     2400
acagggctga tgtgtcattt tgaaccatca tcttggcagc agtaacgaac tggtttcctg     2460
gaccaaatat tttgtcacac ttaggaacag tttctgttcc gtaagccata gcagctactg     2520
cctgggcgcc tcctgctagc acgatacact tagcaccaac cttgtgggca acgtagatga     2580
cttctggggt aagggtacca tccttcttag gtggagatgc aaaaacaatt tctttgcaac     2640
cagcaacttt ggcaggaaca cccagcatca gggaagtgga aggcagaatt gcggttccac     2700
caggaatata gaggccaact ttctcaatag gtcttgcaaa acgagagcag actacaccag     2760
```

```
ggcaagtctc aacttgcaac gtctccgtta gttgagcttc atggaatttc ctgacgttat   2820
ctatagagag atcaatggct ctcttaacgt tatctggcaa ttgcataagt tcctctggga   2880
aaggagcttc taacacaggt gtcttcaaag cgactccatc aaacttggca gttagttcta   2940
aaagggcttt gtcaccattt tgacgaacat tgtcgacaat tggtttgact aattccataa   3000
tctgttccgt tttctggata ggacgacgaa gggcatcttc aatttcttgt gaggaggcct   3060
tagaaacgtc aattttgcac aattcaatac gaccttcaga agggacttct ttaggtttgg   3120
attcttcttt aggttgttcc ttggtgtatc ctggcttggc atctcctttc cttctagtga   3180
cctttaggga cttcatatcc aggtttctct ccacctcgtc caacgtcaca ccgtacttgg   3240
cacatctaac taatgcaaaa taaaataagt cagcacattc ccaggctata tcttccttgg   3300
atttagcttc tgcaagttca tcagcttcct ccctaatttt agcgttcaac aaaacttcgt   3360
cgtcaaataa ccgtttggta taagaacctt ctggagcatt gctcttacga tcccacaagg   3420
tggcttccat ggctctaaga ccctttgatt ggccaaaaca ggaagtgcgt tccaagtgac   3480
agaaaccaac acctgtttgt tcaaccacaa atttcaagca gtctccatca caatccaatt   3540
cgatacccag caacttttga gttgctccag atgtagcacc tttataccac aaaccgtgac   3600
gacgagattg gtagactcca gtttgtgtcc ttatagcctc cggaatagac tttttggacg   3660
agtacaccag gcccaacgag taattagaag agtcagccac caaagtagtg aatagaccat   3720
cggggcggtc agtagtcaaa gacgccaaca aaatttcact gacagggaac ttttttgacat   3780 cttcagaaag ttcgtattca gtagtcaatt gccgagcatc aataatgggg attataccag   3840
aagcaacagt ggaagtcaca tctaccaact tgcggtctc agaaaaagca taaacagttc   3900
tactaccgcc attagtgaaa cttttcaaat cgcccagtgg agaagaaaaa ggcacagcga   3960
tactagcatt agcgggcaag gatgcaactt tatcaaccag ggtcctatag ataaccctag   4020
cgcctgggat catcctttgg acaactcttt ctgccaaatc taggtccaaa atcacttcat   4080
tgataccatt attgtacaac ttgagcaagt tgtcgatcag ctcctcaaat tggtcctctg   4140
taacggatga ctcaacttgc acattaactt gaagctcagt cgattgagtg aacttgatca   4200
ggttgtgcag ctggtcagca gcatagggaa acacggcttt tcctaccaaa ctcaaggaat   4260
tatcaaactc tgcaacactt gcgtatgcag gtagcaaggg aaatgtcata cttgaagtcg   4320
gacagtgagt gtagtcttga gaaattctga agccgtattt ttattatcag tgagtcagtc   4380
atcaggagat cctctacgcc ggacgcatcg tggccggcat caccggcgcc acaggtgcgg   4440
ttgctggcgc ctatatcgcc gacatcaccg atggggaaga tcgggctcgc cacttcgggc   4500
tcatgagcgc ttgtttcggc gtgggtatgg tggcaggccc cgtggccggg ggactgttgg   4560
gcgccatctc cttgcatgca ccattccttg cggcggcggt gctcaacggc ctcaacctac   4620
tactgggctg cttcctaatg caggagtcgc ataagggaga gcgtcgagta tctatgattg   4680
gaagtatggg aatggtgata cccgcattct tcagtgtctt gaggtctcct atcagattat   4740
gcccaactaa agcaaccgga ggaggagatt tcatggtaaa tttctctgac ttttggtcat   4800
cagtagactc gaactgtgag actatctcgg ttatgacagc agaaatgtcc ttcttggaga   4860
cagtaaatga agtcccacca ataaagaaat ccttgttatc aggaacaaac ttcttgtttc   4920
gaactttttc ggtgccttga actataaaat gtagagtgga tatgtcgggt aggaatggag   4980
cgggcaaatg cttaccttct ggaccttcaa gaggtatgta gggtttgtag atactgatgc   5040
caacttcagt gacaacgttg ctatttcgtt caaaccattc cgaatccaga gaaatcaaag   5100
ttgtttgtct actattgatc caagccagtg cggtcttgaa actgacaata gtgtgctcgt   5160
```

-continued

```
gttttgaggt catctttgta tgaataaatc tagtctttga tctaaataat cttgacgagc   5220
caaggcgata aatacccaaa tctaaaactc ttttaaaacg ttaaaaggac aagtatgtct   5280
gcctgtatta aacccaaat cagctcgtag tctgatcctc atcaacttga ggggcactat    5340
cttgttttag agaaatttgc ggagatgcga tatcgagaaa aaggtacgct gattttaaac   5400
gtgaaattta tctcaagatc tctgcctcgc gcgtttcggt gatgacggtg aaaacctctg   5460
acacatgcag ctcccggaga cggtcacagc ttgtctgtaa gcggatgccg ggagcagaca   5520
agcccgtcag ggcgcgtcag cgggtgttgg cgggtgtcgg ggcgcagcca tgacccagtc   5580
acgtagcgat agcggagtgt atactggctt aactatgcgg catcagagca gattgtactg   5640
agagtgcacc atatgcggtg tgaaataccg cacagatgcg taaggagaaa ataccgcatc   5700
aggcgctctt ccgcttcctc gctcactgac tcgctgcgct cggtcgttcg gctgcggcga   5760
gcggtatcag ctcactcaaa ggcggtaata cggttatcca cagaatcagg gataacgca   5820 ggaaagaaca tgtgagcaaa aggccagcaa aaggccagga accgtaaaaa ggccgcgttg   5880
ctggcgtttt tccataggct ccgcccccct gacgagcatc acaaaaatcg acgctcaagt   5940
cagaggtggc gaaacccgac aggactataa agataccagg cgtttccccc tggaagctcc   6000
ctcgtgcgct ctcctgttcc gaccctgccg cttaccggat acctgtccgc ctttctccct   6060
tcgggaagcg tggcgctttc tcaatgctca cgctgtaggt atctcagttc ggtgtaggtc   6120
gttcgctcca agctgggctg tgtgcacgaa ccccccgttc agcccgaccg ctgcgcctta   6180
tccggtaact atcgtcttga gtccaacccg gtaagcacg acttatcgcc actggcagca    6240
gccactggta acaggattag cagagcgagg tatgtaggcg gtgctacaga gttcttgaag   6300
tggtggccta actacggcta cactagaagg acagtatttg gtatctgcgc tctgctgaag   6360
ccagttacct tcggaaaaag agttggtagc tcttgatccg gcaaacaaac caccgctggt   6420
agcggtggtt tttttgtttg caagcagcag attacgcgca gaaaaaaagg atctcaagaa   6480
gatcctttga tcttttctac ggggtctgac gctcagtgga acgaaaactc acgttaaggg   6540
attttggtca tgagattatc aaaaaggatc ttcacctaga tccttttaaa ttaaaaatga   6600
agttttaaat caatctaaag tatatatgag taaacttggt ctgacagtta ccaatgctta   6660
atcagtgagg cacctatctc agcgatctgt ctatttcgtt catccatagt tgcctgactc   6720
cccgtcgtgt agataactac gatacgggag ggcttaccat ctggccccag tgctgcaatg   6780
ataccgcgag acccacgctc accggctcca gatttatcag caataaacca gccagccgga   6840
agggccgagc gcagaagtgg tcctgcaact ttatccgcct ccatccagtc tattaattgt   6900
tgccgggaag ctagagtaag tagttcgcca gttaatagtt tgcgcaacgt tgttgccatt   6960
gctgcaggca tcgtggtgtc acgctcgtcg tttggtatgg cttcattcag ctccggttcc   7020
caacgatcaa ggcgagttac atgatccccc atgttgtgca aaaaagcggt tagctccttc   7080
ggtcctccga tcgttgtcag aagtaagttg gccgcagtgt tatcactcat ggttatggca   7140
gcactgcata attctcttac tgtcatgcca tccgtaagat gcttttctgt gactggtgag   7200
tactcaacca agtcattctg agaatagtgt atgcggcgac cgagttgctc ttgcccggcg   7260
tcaacacggg ataataccgc gccacatagc agaactttaa aagtgctcat cattggaaaa   7320
cgttcttcgg ggcgaaaact ctcaaggatc ttaccgctgt tgagatccag ttcgatgtaa   7380
cccactcgtg cacccaactg atcttcagca tcttttactt tcaccagcgt ttctgggtga   7440
gcaaaaacag gaaggcaaaa tgccgcaaaa aagggaataa gggcgacacg gaaatgttga   7500
```

```
atactcatac tcttcctttt tcaatattat tgaagcattt atcagggtta ttgtctcatg    7560
agcggataca tatttgaatg tatttagaaa aataaacaaa taggggttcc gcgcacattt    7620
ccccgaaaag tgccacctga cgtctaagaa accattatta tcatgacatt aacctataaa    7680
aataggcgta tcacgaggcc ctttcgtctt caagaattaa ttctcatgtt tgacagctta    7740
tcatcgataa gctgactcat gttggtattg tgaaatagac gcagatcggg aacactgaaa    7800
aataacagtt attattcg                                                  7818

<210> SEQ ID NO 6
<211> LENGTH: 8002
<212> TYPE: DNA
<213> ORGANISM: Artificial
<220> FEATURE:
<223> OTHER INFORMATION: synthetic

<400> SEQUENCE: 6
agatctaaca tccaaagacg aaaggttgaa tgaaaccttt ttgccatccg acatccacag      60
gtccattctc acacataagt gccaaacgca acaggagggg atacactagc agcagaccgt     120
tgcaaacgca ggacctccac tcctcttctc ctcaacaccc acttttgcca tcgaaaaacc     180
agcccagtta ttgggcttga ttggagctcg ctcattccaa ttccttctat taggctacta     240
acaccatgac tttattagcc tgtctatcct ggccccctg gcgaggttca tgtttgttta      300
tttccgaatg caacaagctc cgcattacac ccgaacatca ctccagatga gggctttctg     360
agtgtggggt caaatagttt catgttcccc aaatggccca aaactgacag tttaaacgct     420
gtcttggaac ctaatatgac aaaagcgtga tctcatccaa gatgaactaa gtttggttcg     480
ttgaaatgct aacggccagt tggtcaaaaa gaaacttcca aaagtcgcca taccgtttgt     540
cttgtttggt attgattgac gaatgctcaa aaataatctc attaatgctt agcgcagtct     600
ctctatcgct tctgaacccc ggtgcacctg tgccgaaacg caaatgggga acacccgct      660 ttttggatga ttatgcattg tctccacatt gtatgcttcc aagattctgg tgggaatact     720
gctgatagcc taacgttcat gatcaaaatt taactgttct aaccccctact tgacagcaat     780 atataaacag aaggaagctg ccctgtctta aacctttttt tttatcatca ttattagctt     840
actttcataa ttgcgactgg ttccaattga caagcttttg attttaacga cttttaacga     900
caacttgaga agatcaaaaa acaactaatt attcgaagga tccaaacgat gagatttcct     960
tcaattttta ctgcagtttt attcgcagca tcctccgcat tagctgctct cgagaaaaga    1020
gaggagtacg tgggcctgtc tgcaaaccag tgtgccgtgc cagccaagga cagggtggac    1080
tgcggctacc cccatgtcac ccccaaggag tgcaacaacc ggggctgctg ctttgactcc    1140
aggatccctg gagtgcctg tgtttcaag ccctgcagg aagcagaatg caccttctga     1200
gaattcccta gggcggccgc gaattaattc gccttagaca tgactgttcc tcagttcaag    1260
ttgggcactt acgagaagac cggtcttgct agattctaat caagaggatg tcagaatgcc    1320
atttgcctga gagatgcagg cttcattttt gactttttt tatttgtaac ctatatagta    1380 taggatttt tttgtcattt tgtttcttct cgtacgagct tgctcctgat cagcctatct    1440
cgcagctgat gaatatcttg tggtaggggt ttgggaaaat cattcgagtt tgatgttttt    1500 cttggtatt cccactcctc ttcagagtac agaagattaa gtgagaagtt cgtttgtgca     1560
agcttatcga taagctttaa tgcggtagtt tatcacagtt aaattgctaa cgcagtcagg    1620
caccgtgtat gaaatctaac aatgcgctca tcgtcatcct cggcaccgtc acctggatg     1680 ctgtaggcat aggcttggtt atgccggtac tgccgggcct cttgcgggat atcgtccatt    1740
```

```
ccgacagcat cgccagtcac tatggcgtgc tgctagcgct atatgcgttg atgcaatttc      1800
tatgcgcacc cgttctcgga gcactgtccg accgctttgg ccgccgccca gtcctgctcg      1860
cttcgctact tggagccact atcgactacg cgatcatggc gaccacaccc gtcctgtgga      1920
tctatcgaat ctaaatgtaa gttaaaatct ctaaataatt aaataagtcc cagtttctcc      1980
atacgaacct taacagcatt gcggtgagca tctagacctt caacagcagc cagatccatc      2040
actgcttggc caatatgttt cagtccctca ggagttacgt cttgtgaagt gatgaacttc      2100
tggaaggttg cagtgttaac tccgctgtat tgacgggcat atccgtacgt tggcaaagtg      2160
tggttggtac cggaggagta atctccacaa ctctctggag agtaggcacc aacaaacaca      2220
gatccagcgt gttgtacttg atcaacataa gaagaagcat tctcgatttg caggatcaag      2280
tgttcaggag cgtactgatt ggacatttcc aaagcctgct cgtaggttgc aaccgatagg      2340
gttgtagagt gtgcaataca cttgcgtaca atttcaaccc ttggcaactg cacagcttgg      2400
ttgtgaacag catcttcaat tctggcaagc tccttgtctg tcatatcgac agccaacaga      2460
atcacctggg aatcaatacc atgttcagct tgagacagaa ggtctgaggc aacgaaatct      2520
ggatcagcgt atttatcagc aataactaga acttcagaag gcccagcagg catgtcaata      2580
ctacacaggg ctgatgtgtc attttgaacc atcatcttgg cagcagtaac gaactggttt      2640
cctggaccaa atattttgtc acacttagga acagttctg ttccgtaagc catagcagct       2700
actgcctggg cgcctcctgc tagcacgata cacttagcac caaccttgtg gcaacgtag       2760 atgacttctg gggtaagggt accatccttc ttaggtggag atgcaaaaac aatttctttg      2820
caaccagcaa ctttggcagg aacacccagc atcaggaag tggaaggcag aattgcggtt       2880
ccaccaggaa tatagaggcc aactttctca ataggtcttg caaaacgaga gcagactaca      2940
ccagggcaag tctcaacttg caacgtctcc gttagttgag cttcatggaa tttcctgacg      3000
ttatctatag agagatcaat ggctctctta acgttatctg gcaattgcat aagttcctct      3060
gggaaaggag cttctaacac aggtgtcttc aaagcgactc catcaaactt ggcagttagt      3120
tctaaaaggg ctttgtcacc attttgacga acattgtcga caattggttt gactaattcc      3180
ataatctgtt ccgttttctg gataggacga cgaagggcat cttcaatttc ttgtgaggag      3240
gccttagaaa cgtcaatttt gcacaattca atacgacctt cagaagggac ttctttaggt      3300
ttggattctt cttaggttg ttccttggtg tatcctggct tggcatctcc tttccttcta       3360
gtgaccttta gggacttcat atccaggttt ctctccacct cgtccaacgt cacaccgtac      3420
ttggcacatc taactaatgc aaaataaaat aagtcagcac attcccaggc tatatcttcc      3480
ttggatttag cttctgcaag ttcatcagct tcctccctaa ttttagcgtt caacaaaact      3540
tcgtcgtcaa ataaccgttt ggtataagaa ccttctggag cattgctctt acgatcccac      3600
aaggtggctt ccatggctct aagacccttt gattggccaa acaggaagt gcgttccaag       3660 tgacagaaac caacacctgt tgttcaacc acaaatttca agcagtctcc atcacaatcc       3720
aattcgatac ccagcaactt ttgagttgct ccagatgtag cacctttata ccacaaaccg      3780
tgacgacgag attggtagac tccagtttgt gtccttatag cctccggaat agacttttg       3840 gacgagtaca ccaggcccaa cgagtaatta gaagagtcag ccaccaaagt agtgaataga      3900 ccatcgggc ggtcagtagt caaagacgcc aacaaaattt cactgacagg gaactttttg       3960
acatcttcag aaagttcgta ttcagtagtc aattgccgag catcaataat ggggattata      4020
ccagaagcaa cagtggaagt cacatctacc aactttgcgg tctcagaaaa agcataaaca      4080
```

```
gttctactac cgccattagt gaaacttttc aaatcgccca gtggagaaga aaaaggcaca    4140
gcgatactag cattagcggg caaggatgca actttatcaa ccagggtcct atagataacc    4200
ctagcgcctg ggatcatcct ttggacaact ctttctgcca aatctaggtc caaaatcact    4260
tcattgatac cattattgta caacttgagc aagttgtcga tcagctcctc aaattggtcc    4320
tctgtaacgg atgactcaac ttgcacatta acttgaagct cagtcgattg agtgaacttg    4380
atcaggttgt gcagctggtc agcagcatag ggaaacacgg cttttcctac caaactcaag    4440
gaattatcaa actctgcaac acttgcgtat gcaggtagca agggaaatgt catacttgaa    4500
gtcggacagt gagtgtagtc ttgagaaatt ctgaagccgt atttttatta tcagtgagtc    4560
agtcatcagg agatcctcta cgccggacgc atcgtggccg gcatcaccgg cgccacaggt    4620
gcggttgctg gcgcctatat cgccgacatc accgatgggg aagatcgggc tcgccacttc    4680
gggctcatga gcgcttgttt cggcgtgggt atggtggcag gccccgtggc cgggggactg    4740
ttgggcgcca tctccttgca tgcaccattc cttgcggcgg cggtgctcaa cggcctcaac    4800
ctactactgg gctgcttcct aatgcaggag tcgcataagg gagagcgtcg agtatctatg    4860
attggaagta tgggaatggt gatacccgca ttcttcagtg tcttgaggtc tcctatcaga    4920
ttatgcccaa ctaaagcaac cggaggagga gatttcatgg taaatttctc tgacttttgg    4980
tcatcagtag actcgaactg tgagactatc tcggttatga cagcagaaat gtccttcttg    5040
gagacagtaa atgaagtccc accaataaag aaatccttgt tatcaggaac aaacttcttg    5100
tttcgaactt tttcggtgcc ttgaactata aatgtagag tggatatgtc gggtaggaat     5160
ggagcgggca aatgcttacc ttctggacct tcaagaggta tgtagggttt gtagatactg    5220
atgccaactt cagtgacaac gttgctattt cgttcaaacc attccgaatc cagagaaatc    5280
aaagttgttt gtctactatt gatccaagcc agtgcggtct tgaaactgac aatagtgtgc    5340
tcgtgttttg aggtcatctt tgtatgaata aatctagtct ttgatctaaa taatcttgac    5400
gagccaaggc gataaatacc caaatctaaa actcttttaa aacgttaaaa ggacaagtat    5460
gtctgcctgt attaaacccc aaatcagctc gtagtctgat cctcatcaac ttgaggggca    5520
ctatcttgtt ttagagaaat ttgcggagat gcgatatcga gaaaaggta cgctgatttt     5580 aaacgtgaaa tttatctcaa gatctctgcc tcgcgcgttt cggtgatgac ggtgaaaacc    5640
tctgacacat gcagctcccg gagacggtca cagcttgtct gtaagcggat gccgggagca    5700
gacaagcccg tcagggcgcg tcagcgggtg ttggcgggtg tcgggcgca gccatgaccc      5760 agtcacgtag cgatagcgga gtgtatactg gcttaactat gcggcatcag agcagattgt    5820
actgagagtg caccatatgc ggtgtgaaat accgcacaga tgcgtaagga gaaataccg     5880 catcaggcgc tcttccgctt cctcgctcac tgactcgctg cgctcggtcg ttcggctgcg    5940
gcgagcggta tcagctcact caaaggcggt aatacggtta ccacagaat caggggataa     6000 cgcaggaaag aacatgtgag caaaaggcca gcaaaaggcc aggaaccgta aaaaggccgc    6060
gttgctggcg tttttccata ggctccgccc ccctgacgag catcacaaaa atcgacgctc    6120
aagtcagagg tggcgaaacc cgacaggact ataaagatac caggcgtttc ccctggaag    6180 ctccctcgtg cgctctcctg ttccgaccct gccgcttacc ggatacctgt ccgcctttct    6240
cccttcggga agcgtggcgc tttctcaatg ctcacgctgt aggtatctca gttcggtgta    6300
ggtcgttcgc tccaagctgg gctgtgtgca cgaaccccc gttcagcccg accgctgcgc     6360
cttatccggt aactatcgtc ttgagtccaa cccggtaaga cacgacttat cgccactggc    6420
agcagccact ggtaacagga ttagcagagc gaggtatgta ggcggtgcta cagagttctt    6480
```

```
gaagtggtgg cctaactacg gctacactag aaggacagta tttggtatct gcgctctgct    6540
gaagccagtt accttcggaa aaagagttgg tagctcttga tccggcaaac aaaccaccgc    6600
tggtagcggt ggttttttg tttgcaagca gcagattacg cgcagaaaaa aaggatctca     6660
agaagatcct ttgatctttt ctacggggtc tgacgctcag tggaacgaaa actcacgtta    6720
agggattttg gtcatgagat tatcaaaaag gatcttcacc tagatccttt taaattaaaa    6780
atgaagtttt aaatcaatct aaagtatata tgagtaaact tggtctgaca gttaccaatg    6840
cttaatcagt gaggcaccta tctcagcgat ctgtctattt cgttcatcca tagttgcctg    6900
actccccgtc gtgtagataa ctacgatacg ggagggctta ccatctggcc ccagtgctgc    6960
aatgataccg cgagacccac gctcaccggc tccagattta tcagcaataa accagccagc    7020
cggaagggcc gagcgcagaa gtggtcctgc aactttatcc gcctccatcc agtctattaa    7080
ttgttgccgg gaagctagag taagtagttc gccagttaat agtttgcgca acgttgttgc    7140
cattgctgca ggcatcgtgg tgtcacgctc gtcgtttggt atggcttcat tcagctccgg    7200
ttcccaacga tcaaggcgag ttacatgatc ccccatgttg tgcaaaaaag cggttagctc    7260
cttcggtcct ccgatcgttg tcagaagtaa gttggccgca gtgttatcac tcatggttat    7320
ggcagcactg cataattctc ttactgtcat gccatccgta agatgctttt ctgtgactgg    7380
tgagtactca accaagtcat tctgagaata gtgtatgcgg cgaccgagtt gctcttgccc    7440
ggcgtcaaca cgggataata ccgcgccaca tagcagaact ttaaaagtgc tcatcattgg    7500
aaaacgttct cggggcgaaa actctcaag gatcttaccg ctgttgagat ccagttcgat     7560
gtaacccact cgtgcaccca actgatcttc agcatctttt actttcacca gcgtttctgg    7620
gtgagcaaaa acaggaaggc aaaatgccgc aaaaaaggga ataagggcga cacggaaatg    7680
ttgaatactc atactcttcc tttttcaata ttattgaagc atttatcagg gttattgtct    7740
catgagcgga tacatatttg aatgtattta gaaaaataaa caaatagggg ttccgcgcac    7800
atttccccga aaagtgccac ctgacgtcta agaaaccatt attatcatga cattaaccta    7860
taaaaatagg cgtatcacga ggccctttcg tcttcaagaa ttaattctca tgtttgacag    7920
cttatcatcg ataagctgac tcatgttggt attgtgaaat agacgcagat cgggaacact    7980
gaaaaataac agttattatt cg                                             8002

<210> SEQ ID NO 7
<211> LENGTH: 8189
<212> TYPE: DNA
<213> ORGANISM: Artificial
<220> FEATURE:
<223> OTHER INFORMATION: synthetic

<400> SEQUENCE: 7
agatctaaca tccaaagacg aaaggttgaa tgaaaccttt ttgccatccg acatccacag      60
gtccattctc acacataagt gccaaacgca acaggagggg atacactagc agcagaccgt     120
tgcaaacgca ggacctccac tcctcttctc ctcaacaccc acttttgcca tcgaaaaacc     180
agcccagtta ttgggcttga ttggagctcg ctcattccaa ttccttctat taggctacta     240
acaccatgac tttattagcc tgtctatcct ggcccccctg cgaggttcca tgtttgttta     300
tttccgaatg caacaagctc cgcattacac ccgaacatca ctccagatga gggctttctg     360 agtgtgggt caaatagttt catgttcccc aaatggccca aaactgacag tttaaacgct     420
gtcttggaac ctaatatgac aaaagcgtga tctcatccaa gatgaactaa gtttggttcg     480
```

```
ttgaaatgct aacggccagt tggtcaaaaa gaaacttcca aaagtcgcca taccgtttgt    540
cttgtttggt attgattgac gaatgctcaa aaataatctc attaatgctt agcgcagtct    600
ctctatcgct tctgaacccc ggtgcacctg tgccgaaacg caaatgggga acacccgct     660 ttttggatga ttatgcattg tctccacatt gtatgcttcc aagattctgg tgggaatact    720
gctgatagcc taacgttcat gatcaaaatt taactgttct aaccccctact tgacagcaat   780 atataaacag aaggaagctg ccctgtctta aaccttttt tttatcatca ttattagctt    840
actttcataa ttgcgactgg ttccaattga caagcttttg attttaacga cttttaacga    900
caacttgaga agatcaaaaa acaactaatt attcgaagga tccaaacgat gagatttcct    960
tcaattttta ctgcagtttt attcgcagca tcctccgcat tagctgctcc agtcaacact   1020
acaacagaag atgaaacggc acaaattccg gctgaagctg tcatcggtta ctcagattta   1080
gaagggattt cgatgttgc tgttttgcca ttttccaaca gcacaaataa cgggttattg    1140
tttataaata ctactattgc cagcattgct gctaaagaag aagggtatc tctcgagaaa    1200 agagaggctg aggagtacgt gggcctgtct gcaaaccagt gtgccgtgcc agccaaggac   1260
agggtggact gcggctaccc ccatgtcacc cccaaggagt gcaacaaccg gggctgctgc   1320
tttgactcca ggatccctgg agtgccttgg tgtttcaagc cctgcagga agcagaatgc    1380 accttctgag aattccctag gcggccgcg aattaattcg ccttagacat gactgttcct    1440
cagttcaagt tgggcactta cgagaagacc ggtcttgcta gattctaatc aagaggatgt   1500
cagaatgcca tttgcctgag agatgcaggc ttcattttg atacttttt atttgtaacc    1560 tatatagtat aggatttttt ttgtcatttt gtttcttctc gtacgagctt gctcctgatc   1620
agcctatctc gcagctgatg aatatcttgt ggtaggggtt tgggaaaatc attcgagttt   1680 gatgttttc ttggtatttc ccactcctct tcagagtaca aagattaag tgagaagttc    1740 gtttgtgcaa gcttatcgat aagctttaat gcggtagttt atcacagtta aattgctaac   1800
gcagtcaggc accgtgtatg aaatctaaca atgcgctcat cgtcatcctc ggcaccgtca   1860
ccctggatgc tgtaggcata ggcttggtta tgccggtact gccgggcctc ttgcgggata   1920
tcgtccattc cgacagcatc gccagtcact atggcgtgct gctagcgcta tatgcgttga   1980
tgcaatttct atgcgcaccc gttctcggag cactgtccga ccgctttggc cgccgcccag   2040
tcctgctcgc ttcgctactt ggagccacta tcgactacgc gatcatggcg accacacccg   2100
tcctgtggat ctatcgaatc taaatgtaag ttaaaatctc taaataatta aataagtccc   2160
agtttctcca tacgaacctt aacagcattg cggtgagcat ctagaccttc aacagcagcc   2220
agatccatca ctgcttggcc aatatgtttc agtccctcag gagttacgtc ttgtgaagtg   2280
atgaacttct ggaaggttgc agtgttaact ccgctgtatt gacgggcata tccgtacgtt   2340
ggcaaagtgt ggttggtacc ggaggagtaa tctccacaac tctctggaga gtaggcacca   2400
acaaacacag atccagcgtg ttgtacttga tcaacataag aagaagcatt ctcgatttgc   2460
aggatcaagt gttcaggagc gtactgattg acatttccaa agcctgctc gtaggttgca   2520 accgatagg ttgtagagtg tgcaatacac ttgcgtacaa tttcaaccct tggcaactgc   2580
acagcttggt tgtgaacagc atcttcaatt ctggcaagct ccttgtctgt catatcgaca   2640
gccaacagaa tcacctggga atcaatacca tgttcagctt gagacagaag gtctgaggca   2700
acgaaatctg gatcagcgta tttatcagca ataactagaa cttcagaagg cccagcaggc   2760
atgtcaatac tacacagggc tgatgtgtca ttttgaacca tcatcttggc agcagtaacg   2820
aactggtttc ctggaccaaa tattttgtca cacttaggaa cagtttctgt tccgtaagcc   2880
```

```
atagcagcta ctgcctgggc gcctcctgct agcacgatac acttagcacc aaccttgtgg    2940
gcaacgtaga tgacttctgg ggtaagggta ccatccttct taggtggaga tgcaaaaaca    3000
atttctttgc aaccagcaac tttggcagga acacccagca tcaggaagt  ggaaggcaga    3060
attgcggttc caccaggaat atagaggcca actttctcaa taggtcttgc aaaacgagag    3120
cagactacac cagggcaagt ctcaacttgc aacgtctccg ttagttgagc ttcatggaat    3180
ttcctgacgt tatctataga gagatcaatg gctctcttaa cgttatctgg caattgcata    3240
agttcctctg ggaaaggagc ttctaacaca ggtgtcttca aagcgactcc atcaaacttg    3300
gcagttagtt ctaaaagggc tttgtcacca ttttgacgaa cattgtcgac aattggtttg    3360
actaattcca taatctgttc cgttttctgg ataggacgac gaagggcatc ttcaatttct    3420
tgtgaggagg ccttagaaac gtcaattttg cacaattcaa tacgaccttc agaagggact    3480
tctttaggtt tggattcttc tttaggttgt tccttggtgt atcctggctt ggcatctcct    3540
ttccttctag tgacctttag ggacttcata tccaggtttc tctccacctc gtccaacgtc    3600
acaccgtact tggcacatct aactaatgca aataaaata  agtcagcaca ttcccaggct    3660
atatcttcct tggatttagc ttctgcaagt tcatcagctt cctccctaat tttagcgttc    3720
aacaaaactt cgtcgtcaaa taccgtttg  gtataagaac cttctggagc attgctctta    3780
cgatcccaca aggtggcttc catggctcta agacccttg  attggccaaa acaggaagtg    3840
cgttccaagt gacagaaacc aacacctgtt tgttcaacca caatttcaa  gcagtctcca    3900
tcacaatcca attcgatacc cagcaacttt tgagttgctc cagatgtagc acctttatac    3960
cacaaaccgt gacgacgaga ttggtagact ccagtttgtg tccttatagc ctccggaata    4020
gacttttgg  acgagtacac caggcccaac gagtaattag aagagtcagc caccaaagta    4080
gtgaatagac catcggggcg gtcagtagtc aaagacgcca acaaaatttc actgacaggg    4140
aacttttga  catcttcaga aagttcgtat tcagtagtca attgccgagc atcaataatg    4200
gggattatac cagaagcaac agtggaagtc acatctacca actttgcggt ctcagaaaaa    4260
gcataaacag ttctactacc gccattagtg aaacttttca aatcgcccag tggagaagaa    4320
aaaggcacag cgatactagc attagcgggc aaggatgcaa ctttatcaac cagggtccta    4380
tagataaccc tagcgcctgg gatcatcctt tggacaactc tttctgccaa atctaggtcc    4440
aaaatcactt cattgatacc attattgtac aacttgagca agttgtcgat cagctcctca    4500
aattggtcct ctgtaacgga tgactcaact tgcacattaa cttgaagctc agtcgattga    4560
gtgaacttga tcaggttgtg cagctggtca gcagcatagg gaaacacggc ttttcctacc    4620
aaactcaagg aattatcaaa ctctgcaaca cttgcgtatg caggtagcaa gggaaatgtc    4680
atacttgaag tcggacagtg agtgtagtct tgagaaattc tgaagccgta ttttattat    4740
cagtgagtca gtcatcagga gatcctctac gccggacgca tcgtggccgg catcaccggc    4800
gccacaggtg cggttgctgg cgcctatatc gccgacatca ccgatgggga agatcgggct    4860
cgccacttcg ggctcatgag cgcttgtttc ggcgtgggta tggtggcagg ccccgtggcc    4920
gggggactgt tgggcgccat ctccttgcat gcaccattcc ttgcggcggc ggtgctcaac    4980
ggcctcaacc tactactggg ctgcttccta atgcaggagt cgcataaggg agagcgtcga    5040
gtatctatga ttggaagtat gggaatggtg atacccgcat tcttcagtgt cttgaggtct    5100
cctatcagat tatgcccaac taaagcaacc ggaggaggag atttcatggt aaatttctct    5160
gacttttggt catcagtaga ctcgaactgt gagactatct cggttatgac agcagaaatg    5220
```

```
tccttcttgg agacagtaaa tgaagtccca ccaataaaga aatccttgtt atcaggaaca    5280
aacttcttgt ttcgaactttt ttcggtgcct tgaactataa aatgtagagt ggatatgtcg   5340
ggtaggaatg gagcgggcaa atgcttacct tctggacctt caagaggtat gtagggtttg   5400
tagatactga tgccaacttc agtgacaacg ttgctatttc gttcaaacca ttccgaatcc   5460
agagaaatca aagttgtttg tctactattg atccaagcca gtgcggtctt gaaactgaca   5520
atagtgtgct cgtgttttga ggtcatcttt gtatgaataa atctagtctt tgatctaaat   5580
aatcttgacg agccaaggcg ataaatacccc aaatctaaaa ctcttttaaa acgttaaaag   5640
gacaagtatg tctgcctgta ttaaacccca aatcagctcg tagtctgatc ctcatcaact   5700
tgaggggcac tatcttgttt tagagaaatt tgcggagatg cgatatcgag aaaaaggtac   5760
gctgatttta aacgtgaaat ttatctcaag atctctgcct cgcgcgtttc ggtgatgacg   5820
gtgaaaacct ctgacacatg cagctcccgg agacggtcac agcttgtctg taagcggatg   5880
ccgggagcag acaagcccgt cagggcgcgt cagcgggtgt tggcgggtgt cggggcgcag   5940
ccatgaccca gtcacgtagc gatagcggag tgtatactgg cttaactatg cggcatcaga   6000
gcagattgta ctgagagtgc accatatgcg gtgtgaaata ccgcacagat gcgtaaggag   6060
aaaataccgc atcaggcgct cttccgcttc ctcgctcact gactcgctgc gctcggtcgt   6120
tcggctgcgg cgagcggtat cagctcactc aaaggcggta atacggttat ccacagaatc   6180
aggggataac gcaggaaaga acatgtgagc aaaaggccag caaaaggcca ggaaccgtaa   6240
aaaggccgcg ttgctggcgt ttttccatag gctccgcccc cctgacgagc atcacaaaaa   6300
tcgacgctca agtcagaggt ggcgaaaccc gacaggacta taaagatacc aggcgtttcc   6360
ccctggaagc tccctcgtgc gctctcctgt tccgaccctg ccgcttaccg gatacctgtc   6420
cgcctttctc ccttcgggaa gcgtggcgct ttctcaatgc tcacgctgta ggtatctcag   6480
ttcggtgtag tcgttcgct ccaagctggg ctgtgtgcac gaaccccccg ttcagcccga   6540
ccgctgcgcc ttatccggta actatcgtct tgagtccaac ccggtaagac acgacttatc   6600
gccactggca gcagccactg gtaacaggat tagcagagcg aggtatgtag gcggtgctac   6660
agagttcttg aagtggtggc ctaactacgg ctacactaga aggacagtat ttggtatctg   6720
cgctctgctg aagccagtta ccttcggaaa aagagttggt agctcttgat ccggcaaaca   6780
aaccaccgct ggtagcggtg gtttttttgt ttgcaagcag cagattacgc gcagaaaaaa   6840
aggatctcaa gaagatcctt tgatcttttc tacggggtct gacgctcagt ggaacgaaaa   6900
ctcacgttaa gggattttgg tcatgagatt atcaaaaagg atcttcacct agatcctttt   6960
aaattaaaaa tgaagtttta atcaatcta aagtatatat gagtaaactt ggtctgacag   7020
ttaccaatgc ttaatcagtg aggcacctat ctcagcgatc tgtctatttc gttcatccat   7080
agttgcctga ctccccgtcg tgtagataac tacgatacgg gagggcttac catctggccc   7140
cagtgctgca atgataccgc gagacccacg ctcaccggct ccagatttat cagcaataaa   7200
ccagccagcc ggaagggccg agcgcagaag tggtcctgca actttatccg cctccatcca   7260
gtctattaat tgttgccggg aagctagagt aagtagttcg ccagttaata gtttgcgcaa   7320
cgttgttgcc attgctgcag gcatcgtggt gtcacgctcg tcgtttggta tggcttcatt   7380
cagctccggt tcccaacgat caaggcgagt tacatgatcc cccatgttgt gcaaaaaagc   7440
ggttagctcc ttcggtcctc cgatcgttgt cagaagtaag ttggccgcag tgttatcact   7500
catggttatg gcagcactgc ataattctct tactgtcatg ccatccgtaa gatgcttttc   7560
tgtgactggt gagtactcaa ccaagtcatt ctgagaatag tgtatgcggc gaccgagttg   7620
```

```
ctcttgcccg gcgtcaacac gggataatac cgcgccacat agcagaactt taaaagtgct    7680
catcattgga aaacgttctt cggggcgaaa actctcaagg atcttagctg ttgagatcca    7740
gttcgatgta acccactcgt gcacccaact gatcttcagc atcttttact ttcaccagcg    7800
tttctgggtg agcaaaaaca ggaaggcaaa atgccgcaaa aagggaata agggcgacac     7860 ggaaatgttg aatactcata ctcttccttt ttcaatatta ttgaagcatt tatcaggggtt   7920 attgtctcat gagcggatac atatttgaat gtatttagaa aaataaacaa ataggggttc    7980
cgcgcacatt tccccgaaaa gtgccacctg acgtctaaga aaccattatt atcatgacat    8040
taacctataa aataggcgt atcacgaggc cctttcgtct tcaagaatta attctcatgt     8100
ttgacagctt atcatcgata agctgactca tgttggtatt gtgaaataga cgcagatcgg    8160
gaacactgaa aataacagt tattattcg                                      8189
```

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

```
<400> SEQUENCE: 16
000

<210> SEQ ID NO 17
<400> SEQUENCE: 17
000

<210> SEQ ID NO 18
<400> SEQUENCE: 18
000

<210> SEQ ID NO 19
<400> SEQUENCE: 19
000

<210> SEQ ID NO 20
<400> SEQUENCE: 20
000

<210> SEQ ID NO 21
<400> SEQUENCE: 21
000

<210> SEQ ID NO 22
<400> SEQUENCE: 22
000

<210> SEQ ID NO 23
<400> SEQUENCE: 23
000

<210> SEQ ID NO 24
<400> SEQUENCE: 24
000

<210> SEQ ID NO 25
<400> SEQUENCE: 25
000

<210> SEQ ID NO 26
<400> SEQUENCE: 26
000

<210> SEQ ID NO 27
<400> SEQUENCE: 27
```

000

<210> SEQ ID NO 28
<400> SEQUENCE: 28
000

<210> SEQ ID NO 29
<400> SEQUENCE: 29
000

<210> SEQ ID NO 30
<400> SEQUENCE: 30
000

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

-continued

```
<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47
<400> SEQUENCE: 47
000

<210> SEQ ID NO 48
<400> SEQUENCE: 48
000

<210> SEQ ID NO 49
<400> SEQUENCE: 49
000
```

-continued

<210> SEQ ID NO 50
<400> SEQUENCE: 50
000

<210> SEQ ID NO 51
<400> SEQUENCE: 51
000

<210> SEQ ID NO 52
<400> SEQUENCE: 52
000

<210> SEQ ID NO 53
<400> SEQUENCE: 53
000

<210> SEQ ID NO 54
<400> SEQUENCE: 54
000

<210> SEQ ID NO 55
<400> SEQUENCE: 55
000

<210> SEQ ID NO 56
<400> SEQUENCE: 56
000

<210> SEQ ID NO 57
<400> SEQUENCE: 57
000

<210> SEQ ID NO 58
<400> SEQUENCE: 58
000

<210> SEQ ID NO 59
<400> SEQUENCE: 59
000

<210> SEQ ID NO 60
<400> SEQUENCE: 60
000

<210> SEQ ID NO 61

-continued

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

-continued

000

<210> SEQ ID NO 73
<400> SEQUENCE: 73
000

<210> SEQ ID NO 74
<400> SEQUENCE: 74
000

<210> SEQ ID NO 75
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

```
<210> SEQ ID NO 84
<400> SEQUENCE: 84
000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000

<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95
```

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101
<211> LENGTH: 491
<212> TYPE: DNA
<213> ORGANISM: Homo sapien

<400> SEQUENCE: 101

```
ggagtcctga gctgcgtccc ggagcccacg gtggtcatgg ctgccagagc gctctgcatg      60
ctggggctgg tcctggcctt gctgtcctcc agctctgctg aggagtacgt gggcctgtct     120
gcaaaccagt gtgccgtgcc agccaaggac agggtggact gcggctaccc ccatgtcacc     180
cccaaggagt gcaacaaccg gggctgctgc tttgactcca ggatccctgg agtgccttgg     240
tgtttcaagc ccctgcagga agcagaatgc accttctgag gcacctccag ctgccccgg      300 ccggggatg cgaggctcgg agcacccttg cccggctgtg attgctgcca ggcactgttc      360
atctcagctt ttctgtccct ttgctcccgg caagcgcttc tgctgaaagt tcatatctgg     420
agcctgatgt cttaacgaat aaaggtccca tgctccaccc taaaaaaaaa aaaaaaaaaa     480
aaaaaaaaaa a                                                          491
```

<210> SEQ ID NO 102
<211> LENGTH: 243
<212> TYPE: DNA
<213> ORGANISM: Porcine

<400> SEQUENCE: 102

```
atggaggcca ggatgttctg gctgctagtg gtgctcctgg ccttggcgtc ctccagctct      60
gccggggagt atgtgggcct gtcggcgaac cagtgtgccg tccctgccaa ggacagggtg     120
gactgcggct accccaggt caccccccgag cagtgcaaca accggggctg ctgcttcgac     180
```

```
tccagcatcc ccggggtgcc ctggtgcttc aagcccctgc aggaaacaga atgcaccttc      240
tga                                                                   243

<210> SEQ ID NO 103
<211> LENGTH: 320
<212> TYPE: DNA
<213> ORGANISM: Canine

<400> SEQUENCE: 103
aacgatctct gagcggtcgg gtccccagag cccacccgtg accatggagg ccagagtgct      60
ctggctgctg gtggtggtcc tggtcctggg gtcctccagc ttggcagtgg cttaccaggg      120
cctggcgacg aacctgtgcg aggtgccgcc caaggacagg gtggactgcg gctaccctga      180
gatcacctcc gagcagtgcg tcaatcgggg ctgctgcttc gactccagca tccacggggt      240
gccctggtgc ttcaagccgt tgcaggacac agaatgcaga ttttgaagca acgccctcga      300
ccccggacac cctgggaagc                                                 320

<210> SEQ ID NO 104
<211> LENGTH: 431
<212> TYPE: DNA
<213> ORGANISM: Rattus norvegicus

<400> SEQUENCE: 104
gaagtttgcg tgctgccatg gagaccagag ccttctggac aaccctgctg ctggtcctgg      60
ttgctgggtc ctcctgcaaa gcccaggaat tgttggcct atctccaagc caatgtatgg       120
ctccaacaaa tgtcagggtg gactgtaact accccactgt cacatcagag cagtgtaaca      180
accgtggttg ctgttttgac tccagcatcc caaatgtgcc ctggtgcttc aaacctctgc      240
aagagacaga atgtacattt tgaagctgtc caggctccag aagggagct  ccacaccctg      300 gactcttgct gatggtagtg gcccagggta acactcaccc ctgatctgct ccctcgcgcc      360
ggccaatata ggagctggga gtccagaaga ataaagacct acagtcagc  acaaggctgt      420 tctaattgcg g                                                          431

<210> SEQ ID NO 105
<211> LENGTH: 450
<212> TYPE: DNA
<213> ORGANISM: Mus musculus

<400> SEQUENCE: 105
atcctgtgca gtggtcctga agcttgcctg ctgccatgga gaccagagcc ctctggctaa      60
tgctgttggt ggtcctggtt gctgggtcct ctgggatagc tgcagattac gttggcctgt      120
ctccaagcca atgtatggtg ccggcaaatg tcagagtgga ctgtggctac ccctctgtca      180
catcggagca gtgtaacaac cgtggctgct gctttgactc agtatcccca atgtgccct       240 ggtgcttcaa acctctgcag gagacagaat gcacattttg aagctgtcca ggctccagga      300
agggagctct gcaccctgga ctcctgctgc tgatggtggt ccaagggtag caagcatccc      360
cgatctgctc cctgctgcag gccaataaag gagccaggag tcctgaagaa taaagacctc      420
acagccaaca caaggctgat ctgattgctg                                      450

<210> SEQ ID NO 106
<211> LENGTH: 250
<212> TYPE: DNA
<213> ORGANISM: Artificial
<220> FEATURE:
```

<223> OTHER INFORMATION: synthetic

<400> SEQUENCE: 106

```
ctgccagagc gctctgcatg ctggggctgg tcctggcctt gctgtcctcc agctctgctg      60
aggagtacgt gggcctgtct gcaaaccagt gtgccgtgcc agccaaggac agggtggact     120
gcggctaccc ccatgtcacc cccaaggagt gcaacaaccg gggctgctgc tttgactcca     180
ggatccctgg agtgccttgg tgtttcaagc ccctgcagga agcagaatgc accttctgag     240
gcacctccag                                                            250
```

<210> SEQ ID NO 107
<211> LENGTH: 243
<212> TYPE: DNA
<213> ORGANISM: Artificial
<220> FEATURE:
<223> OTHER INFORMATION: synthetic

<400> SEQUENCE: 107

```
atggaggcca ggatgttctg gctgctagtg gtgctcctgg ccttggcgtc ctccagctct      60
gccggggagt atgtgggcct gtcggcgaac cagtgtgccg tccctgccaa ggacagggtg     120
gactgcggct accccaggt cacccccgag cagtgcaaca accggggctg ctgcttcgac     180
tccagcatcc ccggggtgcc ctggtgcttc aagcccctgc aggaaacaga atgcaccttc     240
tga                                                                   243
```

<210> SEQ ID NO 108
<211> LENGTH: 290
<212> TYPE: DNA
<213> ORGANISM: Artificial
<220> FEATURE:
<223> OTHER INFORMATION: synthetic

<400> SEQUENCE: 108

```
aacgatctct gagcggtcgg gtccccagag cccacccgtg accatggagg ccagagtgct      60
ctggctgctg gtggtggtcc tggtcctggg gtcctccagc ttggcagtgg cttaccaggg     120
cctggcgacg aacctgtgcg aggtgccgcc caaggacagg gtggactgcg gctaccctga     180
gatcacctcc gagcagtgcg tcaatcgggg ctgctgcttc gactccagca tccacggggt     240
gccctggtgc ttcaagccgt tgcaggacac agaatgcaga ttttgaagca                290
```

<210> SEQ ID NO 109
<211> LENGTH: 270
<212> TYPE: DNA
<213> ORGANISM: Artificial
<220> FEATURE:
<223> OTHER INFORMATION: synthetic

<400> SEQUENCE: 109

```
tgctgccatg gagaccagag ccttctggac aaccctgctg ctggtcctgg ttgctgggtc      60
ctcctgcaaa gcccaggaat tgttggcct atctccaagc caatgtatgg ctccaacaaa     120
tgtcagggtg gactgtaact accccactgt cacatcagag cagtgtaaca accgtggttg     180
ctgttttgac tccagcatcc caaatgtgcc ctggtgcttc aaacctctgc aagagacaga     240
atgtacattt tgaagctgtc caggctccag                                      270
```

<210> SEQ ID NO 110
<211> LENGTH: 280
<212> TYPE: DNA
<213> ORGANISM: Artificial

```
<220> FEATURE:
<223> OTHER INFORMATION: synthetic

<400> SEQUENCE: 110
agcttgcctg ctgccatgga gaccagagcc ctctggctaa tgctgttggt ggtcctggtt      60
gctgggtcct ctgggatagc tgcagattac gttggcctgt ctccaagcca atgtatggtg     120
ccggcaaatg tcagagtgga ctgtggctac ccctctgtca catcggagca gtgtaacaac     180
cgtggctgct gctttgactc cagtatccca aatgtgccct ggtgcttcaa acctctgcag     240
gagacagaat gcacattttg aagctgtcca ggctccagga                            280

<210> SEQ ID NO 111
<211> LENGTH: 198
<212> TYPE: DNA
<213> ORGANISM: Artificial
<220> FEATURE:
<223> OTHER INFORMATION: synthetic

<400> SEQUENCE: 111
ctcgagaaaa gagaggagta cgtgggcctg tctgcaaacc agtgtgccgt gccagccaag      60
gacagggtgg actgcggcta cccccatgtc acccccaagg agtgcaacaa ccggggctgc     120
tgctttgact ccaggatccc tggagtgcct tggtgtttca gcccctgca ggaagcagaa      180 tgcaccttct gagaattc                                                    198

<210> SEQ ID NO 112
<211> LENGTH: 201
<212> TYPE: DNA
<213> ORGANISM: Artificial
<220> FEATURE:
<223> OTHER INFORMATION: synthetic

<400> SEQUENCE: 112
ctcgagaaaa gagccgggga gtatgtgggc ctgtcggcga accagtgtgc cgtccctgcc      60
aaggacaggg tggactgcgg ctaccccag gtcacccccg agcagtgcaa caaccggggc     120
tgctgcttcg actccagcat ccccgggtg ccctggtgct tcaagcccct gcaggaaaca      180
gaatgcacct tctgagaatt c                                                201

<210> SEQ ID NO 113
<211> LENGTH: 198
<212> TYPE: DNA
<213> ORGANISM: Artificial
<220> FEATURE:
<223> OTHER INFORMATION: synthetic

<400> SEQUENCE: 113
ctcgagaaaa gagtggctta ccagggcctg gcgacgaacc tgtgcgaggt gccgcccaag      60
gacagggtgg actgcggcta ccctgagatc acctccgagc agtgcgtcaa tcggggctgc     120
tgcttcgact ccagcatcca cggggtgccc tggtgcttca gccgttgca ggacacagaa      180 tgcagatttt gagaattc                                                    198

<210> SEQ ID NO 114
<211> LENGTH: 198
<212> TYPE: DNA
<213> ORGANISM: Artificial
<220> FEATURE:
<223> OTHER INFORMATION: synthetic

<400> SEQUENCE: 114
```

```
ctcgagaaaa gacaggaatt tgttggccta tctccaagcc aatgtatggc tccaacaaat    60
gtcagggtgg actgtaacta ccccactgtc acatcagagc agtgtaacaa ccgtggttgc   120
tgttttgact ccagcatccc aaatgtgccc tggtgcttca aacctctgca agagacagaa   180
tgtacatttt gagaattc                                                 198
```

<210> SEQ ID NO 115
<211> LENGTH: 198
<212> TYPE: DNA
<213> ORGANISM: Artificial
<220> FEATURE:
<223> OTHER INFORMATION: synthetic

<400> SEQUENCE: 115

```
ctcgagaaaa gagcagatta cgttggcctg tctccaagcc aatgtatggt gccggcaaat    60
gtcagagtgg actgtggcta cccctctgtc acatcggagc agtgtaacaa ccgtggctgc   120
tgctttgact ccagtatccc aaatgtgccc tggtgcttca acctctgca ggagacagaa    180 tgcacatttt gagaattc                                                 198
```

<210> SEQ ID NO 116
<211> LENGTH: 240
<212> TYPE: DNA
<213> ORGANISM: Artificial
<220> FEATURE:
<223> OTHER INFORMATION: synthetic

<400> SEQUENCE: 116

```
ctcgagaaaa gaatgctggg gctggtcctg gccttgctgt cctccagctc tgctgaggag    60
tacgtgggcc tgtctgcaaa ccagtgtgcc gtgccagcca aggacagggt ggactgcggc   120 taccccccatg tcaccccccaa ggagtgcaac aaccggggct gctgctttga ctccaggatc   180
cctggagtgc cttggtgttt caagcccctg caggaagcag aatgcacctt ctgagaattc   240
```

<210> SEQ ID NO 117
<211> LENGTH: 261
<212> TYPE: DNA
<213> ORGANISM: Artificial
<220> FEATURE:
<223> OTHER INFORMATION: synthetic

<400> SEQUENCE: 117

```
ctcgagaaaa gaatggaggc caggatgttc tggctgctag tggtgctcct ggccttggcg    60
tcctccagct ctgccgggga gtatgtgggc ctgtcggcga accagtgtgc cgtccctgcc   120
aaggacaggg tggactgcgg ctaccccccag gtcacccccg agcagtgcaa caaccggggc   180
tgctgcttcg actccagcat ccccggggtg ccctggtgct tcaagcccct gcaggaaaca   240
gaatgcacct tctgagaatt c                                            261
```

<210> SEQ ID NO 118
<211> LENGTH: 262
<212> TYPE: DNA
<213> ORGANISM: Artificial
<220> FEATURE:
<223> OTHER INFORMATION: synthetic

<400> SEQUENCE: 118

```
ctcgagaaaa gaatggaggc cagagtgctc tggctgctgg tggtggtcct ggtcctgggg    60
tcctccagct tggcagtggc ttaccagggc ctggcgacga acctgtgcga ggtgccgccc   120
aaggacaggg tggactgcgg ctaccctgag atcacctccg agcagtgcgt caatcggggc   180
```

```
tgctgcttcg actccagcat ccacggggtg ccctggtgct tcaagccgtt gcaggcacac    240
agaatgcaga ttttgagaat tc                                             262
```

<210> SEQ ID NO 119
<211> LENGTH: 264
<212> TYPE: DNA
<213> ORGANISM: Artificial
<220> FEATURE:
<223> OTHER INFORMATION: synthetic

<400> SEQUENCE: 119

```
ctcgagaaaa gaatggagac cagagccttc tggacaaccc tgctgctggt cctggttgct    60
gggtcctcct gcaaagccca ggaatttgtt ggcctatctc caagccaatg tatggctcca    120
acaaatgtca gggtggactg taactacccc actgtcacat cagagcagtg taacaaccgt    180
ggttgctgtt ttgactccag catcccaaat gtgccctggt gcttcaaacc tctgcaagag    240
acagaatgta cattttgaga attc                                           264
```

<210> SEQ ID NO 120
<211> LENGTH: 264
<212> TYPE: DNA
<213> ORGANISM: Artificial
<220> FEATURE:
<223> OTHER INFORMATION: synthetic

<400> SEQUENCE: 120

```
ctcgagaaaa gaatggagac cagagccctc tggctaatgc tgttggtggt cctggttgct    60
gggtcctctg ggatagctgc agattacgtt ggcctgtctc caagccaatg tatggtgccg    120
gcaaatgtca gagtggactg tggctacccc tctgtcacat cggagcagtg taacaaccgt    180
ggctgctgct ttgactccag tatcccaaat gtgccctggt gcttcaaacc tctgcaggag    240
acagaatgca cattttgaga attc                                           264
```

<210> SEQ ID NO 121
<211> LENGTH: 198
<212> TYPE: DNA
<213> ORGANISM: Artificial
<220> FEATURE:
<223> OTHER INFORMATION: synthetic

<400> SEQUENCE: 121

```
ctcgagaaaa gagaggagta cgtgggcctg tctgcaaacc agtgtgccgt gccagccaag    60
gacagggtgg actgcggcta ccccatgtc accccaagg agtgcaacaa ccggggctgc     120
tgctttgact ccaggatccc tggagtgcct tggtgtttca gcccctgca ggaagcagaa    180 tgcaccttct gagaattc                                                  198
```

<210> SEQ ID NO 122
<211> LENGTH: 200
<212> TYPE: DNA
<213> ORGANISM: Artificial
<220> FEATURE:
<223> OTHER INFORMATION: synthetic

<400> SEQUENCE: 122

```
ctcgagaaaa gagccgggga gtatgtgggc ctgtcggcga accagtgtgc cgtccctgcc    60
aaggacaggg tggactgcgg ctaccccag gtcaccccg agcagtgcaa caaccggggc     120
tgctgcttcg actccagcat cccgggggtg ccctggtgct tcaagcccct gcaggaaaca    180
```

```
<210> SEQ ID NO 123
<211> LENGTH: 198
<212> TYPE: DNA
<213> ORGANISM: Artificial
<220> FEATURE:
<223> OTHER INFORMATION: synthetic

<400> SEQUENCE: 123
ctcgagaaaa gagtggctta ccagggcctg gcgacgaacc tgtgcgaggt gccgcccaag    60
gacagggtgg actgcggcta ccctgagatc acctccgagc agtgcgtcaa tcggggctgc   120
tgcttcgact ccagcatcca cggggtgccc tggtgcttca agccgttgca ggacacagaa   180
tgcagatttt gagaattc                                                 198

<210> SEQ ID NO 124
<211> LENGTH: 198
<212> TYPE: DNA
<213> ORGANISM: Artificial
<220> FEATURE:
<223> OTHER INFORMATION: synthetic

<400> SEQUENCE: 124
ctcgagaaaa gacaggaatt tgttggccta tctccaagcc aatgtatggc tccaacaaat    60
gtcagggtgg actgtaacta ccccactgtc acatcagagc agtgtaacaa ccgtggttgc   120
tgttttgact ccagcatccc aaatgtgccc tggtgcttca aacctctgca agagacagaa   180
tgtacatttt gagaattc                                                 198

<210> SEQ ID NO 125
<211> LENGTH: 198
<212> TYPE: DNA
<213> ORGANISM: Artificial
<220> FEATURE:
<223> OTHER INFORMATION: synthetic

<400> SEQUENCE: 125
ctcgagaaaa gagcagatta cgttggcctg tctccaagcc aatgtatggt gccggcaaat    60
gtcagagtgg actgtggcta cccctctgtc acatcggagc agtgtaacaa ccgtggctgc   120
tgctttgact ccagtatccc aaatgtgccc tggtgcttca aacctctgca ggagacagaa   180
tgcacatttt gagaattc                                                 198

<210> SEQ ID NO 126

<400> SEQUENCE: 126

000

<210> SEQ ID NO 127

<400> SEQUENCE: 127

000

<210> SEQ ID NO 128

<400> SEQUENCE: 128

000

<210> SEQ ID NO 129
```

```
<400> SEQUENCE: 129

000

<210> SEQ ID NO 130
<400> SEQUENCE: 130

000

<210> SEQ ID NO 131
<211> LENGTH: 77
<212> TYPE: DNA
<213> ORGANISM: Artificial
<220> FEATURE:
<223> OTHER INFORMATION: synthetic

<400> SEQUENCE: 131
ggatccaaac gatgagattt ccttctattt ttactgcagt tttattcgct gcatcctccg    60
cattagctgc tctcgag                                                   77

<210> SEQ ID NO 132
<400> SEQUENCE: 132

000

<210> SEQ ID NO 133
<400> SEQUENCE: 133

000

<210> SEQ ID NO 134
<400> SEQUENCE: 134

000

<210> SEQ ID NO 135
<400> SEQUENCE: 135

000

<210> SEQ ID NO 136
<400> SEQUENCE: 136

000

<210> SEQ ID NO 137
<400> SEQUENCE: 137

000

<210> SEQ ID NO 138
<400> SEQUENCE: 138

000

<210> SEQ ID NO 139
<400> SEQUENCE: 139
```

000

<210> SEQ ID NO 140

<400> SEQUENCE: 140

000

<210> SEQ ID NO 141

<400> SEQUENCE: 141

000

<210> SEQ ID NO 142

<400> SEQUENCE: 142

000

<210> SEQ ID NO 143

<400> SEQUENCE: 143

000

<210> SEQ ID NO 144

<400> SEQUENCE: 144

000

<210> SEQ ID NO 145

<400> SEQUENCE: 145

000

<210> SEQ ID NO 146

<400> SEQUENCE: 146

000

<210> SEQ ID NO 147

<400> SEQUENCE: 147

000

<210> SEQ ID NO 148

<400> SEQUENCE: 148

000

<210> SEQ ID NO 149

<400> SEQUENCE: 149

000

<210> SEQ ID NO 150

<400> SEQUENCE: 150

000

```
<210> SEQ ID NO 151
<400> SEQUENCE: 151
000

<210> SEQ ID NO 152
<400> SEQUENCE: 152
000

<210> SEQ ID NO 153
<400> SEQUENCE: 153
000

<210> SEQ ID NO 154
<400> SEQUENCE: 154
000

<210> SEQ ID NO 155
<400> SEQUENCE: 155
000

<210> SEQ ID NO 156
<400> SEQUENCE: 156
000

<210> SEQ ID NO 157
<400> SEQUENCE: 157
000

<210> SEQ ID NO 158
<400> SEQUENCE: 158
000

<210> SEQ ID NO 159
<400> SEQUENCE: 159
000

<210> SEQ ID NO 160
<400> SEQUENCE: 160
000

<210> SEQ ID NO 161
<400> SEQUENCE: 161
000
```

-continued

<210> SEQ ID NO 162
<400> SEQUENCE: 162
000

<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172
<400> SEQUENCE: 172
000

<210> SEQ ID NO 173

```
<400> SEQUENCE: 173

000

<210> SEQ ID NO 174

<400> SEQUENCE: 174

000

<210> SEQ ID NO 175

<400> SEQUENCE: 175

000

<210> SEQ ID NO 176

<400> SEQUENCE: 176

000

<210> SEQ ID NO 177

<400> SEQUENCE: 177

000

<210> SEQ ID NO 178

<400> SEQUENCE: 178

000

<210> SEQ ID NO 179

<400> SEQUENCE: 179

000

<210> SEQ ID NO 180

<400> SEQUENCE: 180

000

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184
```

-continued

000

<210> SEQ ID NO 185

<400> SEQUENCE: 185

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192

<400> SEQUENCE: 192

000

<210> SEQ ID NO 193

<400> SEQUENCE: 193

000

<210> SEQ ID NO 194

<400> SEQUENCE: 194

000

<210> SEQ ID NO 195

<400> SEQUENCE: 195

000

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201
<211> LENGTH: 20
<212> TYPE: DNA
<213> ORGANISM: Artificial
<220> FEATURE:
<223> OTHER INFORMATION: synthetic

<400> SEQUENCE: 201
ctgccagagc gctctgcatg                                        20

<210> SEQ ID NO 202
<211> LENGTH: 20
<212> TYPE: DNA
<213> ORGANISM: Artificial
<220> FEATURE:
<223> OTHER INFORMATION: synthetic

<400> SEQUENCE: 202
ctggaggtgc ctcagaaggt                                        20

<210> SEQ ID NO 203
<211> LENGTH: 20
<212> TYPE: DNA
<213> ORGANISM: Artificial
<220> FEATURE:
<223> OTHER INFORMATION: synthetic

<400> SEQUENCE: 203
atggaggcca ggatgttctg                                        20

<210> SEQ ID NO 204
<211> LENGTH: 20
<212> TYPE: DNA
<213> ORGANISM: Artificial
<220> FEATURE:
<223> OTHER INFORMATION: synthetic

<400> SEQUENCE: 204
tcagaaggtg cattctgttt                    20

<210> SEQ ID NO 205
<211> LENGTH: 20
<212> TYPE: DNA
<213> ORGANISM: Artificial
<220> FEATURE:
<223> OTHER INFORMATION: synthetic

<400> SEQUENCE: 205
aacgatctct gagcggtcgg                    20

<210> SEQ ID NO 206
<211> LENGTH: 20
<212> TYPE: DNA
<213> ORGANISM: Artificial
<220> FEATURE:
<223> OTHER INFORMATION: synthetic

<400> SEQUENCE: 206
tgcttcaaaa tctgcattct                    20

<210> SEQ ID NO 207
<211> LENGTH: 20
<212> TYPE: DNA
<213> ORGANISM: Artificial
<220> FEATURE:
<223> OTHER INFORMATION: synthetic

<400> SEQUENCE: 207
tgctgccatg gagaccagag                    20

<210> SEQ ID NO 208
<211> LENGTH: 20
<212> TYPE: DNA
<213> ORGANISM: Artificial
<220> FEATURE:
<223> OTHER INFORMATION: synthetic

<400> SEQUENCE: 208
ctggagcctg gacagcttca                    20

<210> SEQ ID NO 209
<211> LENGTH: 20
<212> TYPE: DNA
<213> ORGANISM: Artificial
<220> FEATURE:
<223> OTHER INFORMATION: synthetic

<400> SEQUENCE: 209
agcttgcctg ctgccatgga                    20

<210> SEQ ID NO 210
<211> LENGTH: 20
<212> TYPE: DNA
<213> ORGANISM: Artificial
<220> FEATURE:
<223> OTHER INFORMATION: synthetic

<400> SEQUENCE: 210
tcctggagcc tggacagctt                    20

<210> SEQ ID NO 211
<211> LENGTH: 31

-continued

```
<212> TYPE: DNA
<213> ORGANISM: Artificial
<220> FEATURE:
<223> OTHER INFORMATION: synthetic

<400> SEQUENCE: 211
ctcgagaaaa gagaggagta cgtgggcctg t                               31

<210> SEQ ID NO 212
<211> LENGTH: 25
<212> TYPE: DNA
<213> ORGANISM: Artificial
<220> FEATURE:
<223> OTHER INFORMATION: synthetic

<400> SEQUENCE: 212
gaattctcag aaggtgcatt ctgct                                      25

<210> SEQ ID NO 213
<211> LENGTH: 30
<212> TYPE: DNA
<213> ORGANISM: Artificial
<220> FEATURE:
<223> OTHER INFORMATION: synthetic

<400> SEQUENCE: 213
ctcgagaaaa gagccgggga gtatgtgggc                                 30

<210> SEQ ID NO 214
<211> LENGTH: 26
<212> TYPE: DNA
<213> ORGANISM: Artificial
<220> FEATURE:
<223> OTHER INFORMATION: synthetic

<400> SEQUENCE: 214
gaattctcag aaggtgcatt ctgttt                                     26

<210> SEQ ID NO 215
<211> LENGTH: 30
<212> TYPE: DNA
<213> ORGANISM: Artificial
<220> FEATURE:
<223> OTHER INFORMATION: synthetic

<400> SEQUENCE: 215
ctcgagaaaa gagtggctta ccagggcctg                                 30

<210> SEQ ID NO 216
<211> LENGTH: 24
<212> TYPE: DNA
<213> ORGANISM: Artificial
<220> FEATURE:
<223> OTHER INFORMATION: synthetic

<400> SEQUENCE: 216
gaattctcaa aatctgcatt ctgt                                       24

<210> SEQ ID NO 217
<211> LENGTH: 30
<212> TYPE: DNA
<213> ORGANISM: Artificial
<220> FEATURE:
<223> OTHER INFORMATION: synthetic

<400> SEQUENCE: 217
```

-continued ctcgagaaaa gacaggaatt tgttggccta                                              30

<210> SEQ ID NO 218
<211> LENGTH: 24
<212> TYPE: DNA
<213> ORGANISM: Artificial
<220> FEATURE:
<223> OTHER INFORMATION: synthetic

<400> SEQUENCE: 218
gaattctcaa aatgtacatt ctgt                                                    24

<210> SEQ ID NO 219
<211> LENGTH: 30
<212> TYPE: DNA
<213> ORGANISM: Artificial
<220> FEATURE:
<223> OTHER INFORMATION: synthetic

<400> SEQUENCE: 219
ctcgagaaaa gagcagatta cgttggcctg                                              30

<210> SEQ ID NO 220
<211> LENGTH: 24
<212> TYPE: DNA
<213> ORGANISM: Artificial
<220> FEATURE:
<223> OTHER INFORMATION: synthetic

<400> SEQUENCE: 220
gaattctcaa aatgtgcatt ctgt                                                    24

<210> SEQ ID NO 221
<211> LENGTH: 32
<212> TYPE: DNA
<213> ORGANISM: Artificial
<220> FEATURE:
<223> OTHER INFORMATION: synthetic

<400> SEQUENCE: 221
ctcgagaaaa gaatgctggg gctggtcctg gc                                           32

<210> SEQ ID NO 222
<211> LENGTH: 25
<212> TYPE: DNA
<213> ORGANISM: Artificial
<220> FEATURE:
<223> OTHER INFORMATION: synthetic

<400> SEQUENCE: 222
gaattctcag aaggtgcatt ctgct                                                   25

<210> SEQ ID NO 223
<211> LENGTH: 30
<212> TYPE: DNA
<213> ORGANISM: Artificial
<220> FEATURE:
<223> OTHER INFORMATION: synthetic

<400> SEQUENCE: 223
ctcgagaaaa gaatggaggc caggatgttc                                              30

<210> SEQ ID NO 224
<211> LENGTH: 26
<212> TYPE: DNA
<213> ORGANISM: Artificial

```
<220> FEATURE:
<223> OTHER INFORMATION: synthetic

<400> SEQUENCE: 224
gaattctcag aaggtgcatt ctgttt                                           26

<210> SEQ ID NO 225
<211> LENGTH: 29
<212> TYPE: DNA
<213> ORGANISM: Artificial
<220> FEATURE:
<223> OTHER INFORMATION: synthetic

<400> SEQUENCE: 225
ctcgagaaaa gaatggaggc cagagtgct                                        29

<210> SEQ ID NO 226
<211> LENGTH: 24
<212> TYPE: DNA
<213> ORGANISM: Artificial
<220> FEATURE:
<223> OTHER INFORMATION: synthetic

<400> SEQUENCE: 226
gaattctcaa aatctgcatt ctgt                                             24

<210> SEQ ID NO 227
<211> LENGTH: 30
<212> TYPE: DNA
<213> ORGANISM: Artificial
<220> FEATURE:
<223> OTHER INFORMATION: synthetic

<400> SEQUENCE: 227
ctcgagaaaa gaatggagac cagagccttc                                       30

<210> SEQ ID NO 228
<211> LENGTH: 24
<212> TYPE: DNA
<213> ORGANISM: Artificial
<220> FEATURE:
<223> OTHER INFORMATION: synthetic

<400> SEQUENCE: 228
gaattctcaa aatgtacatt ctgt                                             24

<210> SEQ ID NO 229
<211> LENGTH: 30
<212> TYPE: DNA
<213> ORGANISM: Artificial
<220> FEATURE:
<223> OTHER INFORMATION: synthetic

<400> SEQUENCE: 229
ctcgagaaaa gagcagatta cgttggcctg                                       30

<210> SEQ ID NO 230
<211> LENGTH: 24
<212> TYPE: DNA
<213> ORGANISM: Artificial
<220> FEATURE:
<223> OTHER INFORMATION: synthetic

<400> SEQUENCE: 230
gaattctcaa aatgtgcatt ctgt                                             24
```

<210> SEQ ID NO 231
<211> LENGTH: 31
<212> TYPE: DNA
<213> ORGANISM: Artificial
<220> FEATURE:
<223> OTHER INFORMATION: synthetic

<400> SEQUENCE: 231
ctcgagaaaa gagaggagta cgtgggcctg t              31

<210> SEQ ID NO 232
<211> LENGTH: 25
<212> TYPE: DNA
<213> ORGANISM: Artificial
<220> FEATURE:
<223> OTHER INFORMATION: synthetic

<400> SEQUENCE: 232
gaattctcag aaggtgcatt ctgct                     25

<210> SEQ ID NO 233
<211> LENGTH: 30
<212> TYPE: DNA
<213> ORGANISM: Artificial
<220> FEATURE:
<223> OTHER INFORMATION: synthetic

<400> SEQUENCE: 233
ctcgagaaaa gagccgggga gtatgtgggc                30

<210> SEQ ID NO 234
<211> LENGTH: 26
<212> TYPE: DNA
<213> ORGANISM: Artificial
<220> FEATURE:
<223> OTHER INFORMATION: synthetic

<400> SEQUENCE: 234
gaattctcag aaggtgcatt ctgttt                    26

<210> SEQ ID NO 235
<211> LENGTH: 30
<212> TYPE: DNA
<213> ORGANISM: Artificial
<220> FEATURE:
<223> OTHER INFORMATION: synthetic

<400> SEQUENCE: 235
ctcgagaaaa gagtggctta ccagggcctg                30

<210> SEQ ID NO 236
<211> LENGTH: 24
<212> TYPE: DNA
<213> ORGANISM: Artificial
<220> FEATURE:
<223> OTHER INFORMATION: synthetic

<400> SEQUENCE: 236
gaattctcaa aatctgcatt ctgt                      24

<210> SEQ ID NO 237
<211> LENGTH: 30
<212> TYPE: DNA
<213> ORGANISM: Artificial
<220> FEATURE:
<223> OTHER INFORMATION: synthetic

<400> SEQUENCE: 237
ctcgagaaaa gacaggaatt tgttggccta                              30

<210> SEQ ID NO 238
<211> LENGTH: 24
<212> TYPE: DNA
<213> ORGANISM: Artificial
<220> FEATURE:
<223> OTHER INFORMATION: synthetic

<400> SEQUENCE: 238
gaattctcaa aatgtacatt ctgt                                    24

<210> SEQ ID NO 239
<211> LENGTH: 30
<212> TYPE: DNA
<213> ORGANISM: Artificial
<220> FEATURE:
<223> OTHER INFORMATION: synthetic

<400> SEQUENCE: 239
ctcgagaaaa gagcagatta cgttggcctg                              30

<210> SEQ ID NO 240
<211> LENGTH: 24
<212> TYPE: DNA
<213> ORGANISM: Artificial
<220> FEATURE:
<223> OTHER INFORMATION: synthetic

<400> SEQUENCE: 240
gaattctcaa aatgtgcatt ctgt                                    24

<210> SEQ ID NO 241
<211> LENGTH: 17
<212> TYPE: DNA
<213> ORGANISM: Artificial
<220> FEATURE:
<223> OTHER INFORMATION: synthetic

<400> SEQUENCE: 241
ggatccaaac gatgaga                                            17

<210> SEQ ID NO 242
<211> LENGTH: 24
<212> TYPE: DNA
<213> ORGANISM: Artificial
<220> FEATURE:
<223> OTHER INFORMATION: synthetic

<400> SEQUENCE: 242
ctcgagagca gctaatgcgg atgc                                    24

<210> SEQ ID NO 243
<211> LENGTH: 27
<212> TYPE: DNA
<213> ORGANISM: Artificial
<220> FEATURE:
<223> OTHER INFORMATION: synthetic

<400> SEQUENCE: 243
ctcgagtaga attccctagg gcggccg                                 27

<210> SEQ ID NO 244

```
<211> LENGTH: 86
<212> TYPE: DNA
<213> ORGANISM: Artificial
<220> FEATURE:
<223> OTHER INFORMATION: synthetic

<400> SEQUENCE: 244
ggatccaaac gatgagattt ccttctattt ttactgcagt tttattcgct gcatcctccg    60
caatagctgc tctcgagtag aaattc                                         86

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254
```

000

<210> SEQ ID NO 255
<400> SEQUENCE: 255
000

<210> SEQ ID NO 256
<400> SEQUENCE: 256
000

<210> SEQ ID NO 257
<400> SEQUENCE: 257
000

<210> SEQ ID NO 258
<400> SEQUENCE: 258
000

<210> SEQ ID NO 259
<400> SEQUENCE: 259
000

<210> SEQ ID NO 260
<400> SEQUENCE: 260
000

<210> SEQ ID NO 261
<400> SEQUENCE: 261
000

<210> SEQ ID NO 262
<400> SEQUENCE: 262
000

<210> SEQ ID NO 263
<400> SEQUENCE: 263
000

<210> SEQ ID NO 264
<400> SEQUENCE: 264
000

<210> SEQ ID NO 265
<400> SEQUENCE: 265
000

-continued

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

-continued

<210> SEQ ID NO 277
<400> SEQUENCE: 277
000

<210> SEQ ID NO 278
<400> SEQUENCE: 278
000

<210> SEQ ID NO 279
<400> SEQUENCE: 279
000

<210> SEQ ID NO 280
<400> SEQUENCE: 280
000

<210> SEQ ID NO 281
<400> SEQUENCE: 281
000

<210> SEQ ID NO 282
<400> SEQUENCE: 282
000

<210> SEQ ID NO 283
<400> SEQUENCE: 283
000

<210> SEQ ID NO 284
<400> SEQUENCE: 284
000

<210> SEQ ID NO 285
<400> SEQUENCE: 285
000

<210> SEQ ID NO 286
<400> SEQUENCE: 286
000

<210> SEQ ID NO 287
<400> SEQUENCE: 287
000

<210> SEQ ID NO 288

-continued

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300

<400> SEQUENCE: 300

000

<210> SEQ ID NO 301
<211> LENGTH: 73
<212> TYPE: PRT
<213> ORGANISM: Homo sapien

<400> SEQUENCE: 301

```
Met Leu Gly Leu Val Leu Ala Leu Leu Ser Ser Ser Ala Glu Glu
1               5                   10                  15

Tyr Val Gly Leu Ser Ala Asn Gln Cys Ala Val Pro Ala Lys Asp Arg
                20                  25                  30

Val Asp Cys Gly Tyr Pro His Val Thr Pro Lys Glu Cys Asn Asn Arg
            35                  40                  45

Gly Cys Cys Phe Asp Ser Arg Ile Pro Gly Val Pro Trp Cys Phe Lys
    50                  55                  60

Pro Leu Gln Glu Ala Glu Cys Thr Phe
65                  70
```

<210> SEQ ID NO 302
<211> LENGTH: 80
<212> TYPE: PRT
<213> ORGANISM: Porcine

<400> SEQUENCE: 302

```
Met Glu Ala Arg Met Phe Trp Leu Leu Val Val Leu Ala Leu Ala
1               5                   10                  15

Ser Ser Ser Ala Gly Glu Tyr Val Gly Leu Ser Ala Asn Gln Cys
                20                  25                  30

Ala Val Pro Ala Arg Asp Arg Val Asp Cys Gly Tyr Pro Gln Val Thr
            35                  40                  45

Pro Glu Gln Cys Asn Asn Arg Gly Cys Cys Phe Asp Ser Ser Ile Pro
    50                  55                  60

Gly Val Pro Trp Cys Phe Lys Pro Leu Gln Glu Thr Glu Cys Thr Phe
65                  70                  75                  80
```

<210> SEQ ID NO 303
<211> LENGTH: 80
<212> TYPE: PRT
<213> ORGANISM: Canine

<400> SEQUENCE: 303

```
Met Glu Ala Arg Val Leu Trp Leu Leu Val Val Leu Val Leu Gly
1               5                   10                  15

Ser Ser Ser Leu Ala Val Ala Tyr Gln Gly Leu Ala Thr Asn Leu Cys
                20                  25                  30

Glu Val Pro Pro Lys Asp Arg Val Asp Cys Gly Tyr Pro Glu Ile Thr
            35                  40                  45

Ser Glu Gln Cys Val Asn Arg Gly Cys Cys Phe Asp Ser Ser Ile His
    50                  55                  60

Gly Val Pro Trp Cys Phe Lys Pro Leu Gln Asp Thr Glu Cys Arg Phe
65                  70                  75                  80
```

-continued

<210> SEQ ID NO 304
<211> LENGTH: 81
<212> TYPE: PRT
<213> ORGANISM: Rattus norvegicus

<400> SEQUENCE: 304

Met Glu Thr Arg Ala Phe Trp Thr Thr Leu Leu Val Leu Val Ala
1               5                   10                  15

Gly Ser Ser Cys Lys Ala Gln Glu Phe Val Gly Leu Ser Pro Ser Gln
            20                  25                  30

Cys Met Ala Pro Thr Asn Val Arg Val Asp Cys Asn Tyr Pro Thr Val
            35                  40                  45

Thr Ser Glu Gln Cys Asn Asn Arg Gly Cys Cys Phe Asp Ser Ser Ile
        50                  55                  60

Pro Asn Val Pro Trp Cys Phe Lys Pro Leu Gln Glu Thr Glu Cys Thr
65                  70                  75                  80

Phe

<210> SEQ ID NO 305
<211> LENGTH: 81
<212> TYPE: PRT
<213> ORGANISM: Mus musculus

<400> SEQUENCE: 305

Met Glu Thr Arg Ala Leu Trp Leu Met Leu Leu Val Val Leu Val Ala
1               5                   10                  15

Gly Ser Ser Gly Ile Ala Ala Asp Tyr Val Gly Leu Ser Pro Ser Gln
            20                  25                  30

Cys Met Val Pro Ala Asn Val Arg Val Asp Cys Gly Tyr Pro Ser Val
            35                  40                  45

Thr Ser Glu Gln Cys Asn Asn Arg Gly Cys Cys Phe Asp Ser Ser Ile
        50                  55                  60

Pro Asn Val Pro Trp Cys Phe Lys Pro Leu Gln Glu Thr Glu Cys Thr
65                  70                  75                  80

Phe

<210> SEQ ID NO 306
<211> LENGTH: 144
<212> TYPE: PRT
<213> ORGANISM: Artificial
<220> FEATURE:
<223> OTHER INFORMATION: synthetic

<400> SEQUENCE: 306

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Leu Ser Ile Ala Ala Lys Glu Glu Gly Val
65                  70                  75                  80

Ser Leu Glu Lys Arg Glu Glu Tyr Val Gly Leu Ser Ala Asn Gln Cys
                85                  90                  95

Ala Val Pro Ala Lys Asp Arg Val Asp Cys Gly Tyr Pro His Val Thr
            100                 105                 110

```
Pro Lys Glu Cys Asn Asn Arg Gly Cys Cys Phe Asp Ser Arg Ile Pro
            115                 120                 125

Gly Val Pro Trp Cys Phe Lys Pro Leu Gln Glu Ala Glu Cys Thr Phe
        130                 135                 140

<210> SEQ ID NO 307
<211> LENGTH: 144
<212> TYPE: PRT
<213> ORGANISM: Artificial
<220> FEATURE:
<223> OTHER INFORMATION: synthetic

<400> SEQUENCE: 307

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Leu Ser Ile Ala Ala Lys Glu Glu Gly Val
65                  70                  75                  80

Ser Leu Glu Lys Arg Gly Glu Tyr Val Gly Leu Ser Ala Asn Gln Cys
                85                  90                  95

Ala Val Pro Ala Arg Asp Arg Val Asp Cys Gly Tyr Pro Gln Val Thr
            100                 105                 110

Pro Glu Gln Cys Asn Asn Arg Gly Cys Cys Phe Asp Ser Ser Ile Pro
            115                 120                 125

Gly Val Pro Trp Cys Phe Lys Pro Leu Gln Glu Thr Glu Cys Thr Phe
        130                 135                 140

<210> SEQ ID NO 308
<211> LENGTH: 144
<212> TYPE: PRT
<213> ORGANISM: Artificial
<220> FEATURE:
<223> OTHER INFORMATION: synthetic

<400> SEQUENCE: 308

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Leu Ser Ile Ala Ala Lys Glu Glu Gly Val
65                  70                  75                  80

Ser Leu Glu Lys Arg Val Ala Tyr Gln Gly Leu Ala Thr Asn Leu Cys
                85                  90                  95

Glu Val Pro Pro Lys Asp Arg Val Asp Cys Gly Tyr Pro Glu Ile Thr
            100                 105                 110

Ser Glu Gln Cys Val Asn Arg Gly Cys Cys Phe Asp Ser Ser Ile His
            115                 120                 125

Gly Val Pro Trp Cys Phe Lys Pro Leu Gln Asp Thr Glu Cys Arg Phe
```

<210> SEQ ID NO 309
<211> LENGTH: 144
<212> TYPE: PRT
<213> ORGANISM: Artificial
<220> FEATURE:
<223> OTHER INFORMATION: synthetic

<400> SEQUENCE: 309

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Leu Ser Ile Ala Ala Lys Glu Glu Gly Val
65                  70                  75                  80

Ser Leu Glu Lys Arg Gln Glu Phe Val Gly Leu Ser Pro Ser Gln Cys
                85                  90                  95

Met Ala Pro Thr Asn Val Arg Val Asp Cys Asn Tyr Pro Thr Val Thr
            100                 105                 110

Ser Glu Gln Cys Asn Asn Arg Gly Cys Cys Phe Asp Ser Ser Ile Pro
        115                 120                 125

Asn Val Pro Trp Cys Phe Lys Pro Leu Gln Glu Thr Glu Cys Thr Phe
    130                 135                 140

<210> SEQ ID NO 310
<211> LENGTH: 144
<212> TYPE: PRT
<213> ORGANISM: Artificial  Sequence
<220> FEATURE:
<223> OTHER INFORMATION: Synthetic

<400> SEQUENCE: 310

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Leu Ser Ile Ala Ala Lys Glu Glu Gly Val
65                  70                  75                  80

Ser Leu Glu Lys Arg Ala Asp Tyr Val Gly Leu Ser Pro Ser Gln Cys
                85                  90                  95

Met Val Pro Ala Asn Val Arg Val Asp Cys Gly Tyr Pro Ser Val Thr
            100                 105                 110

Ser Glu Gln Cys Asn Asn Arg Gly Cys Cys Phe Asp Ser Ser Ile Pro
        115                 120                 125

Asn Val Pro Trp Cys Phe Lys Pro Leu Gln Glu Thr Glu Cys Thr Phe
    130                 135                 140

<210> SEQ ID NO 311
<211> LENGTH: 158

```
<212> TYPE: PRT
<213> ORGANISM: Artificial Sequence
<220> FEATURE:
<223> OTHER INFORMATION: synthetic

<400> SEQUENCE: 311

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Leu Ser Ile Ala Ala Lys Glu Glu Gly Val
65                  70                  75                  80

Ser Leu Glu Lys Arg Met Leu Gly Leu Val Leu Ala Leu Leu Ser Ser
                85                  90                  95

Ser Ser Ala Glu Glu Tyr Val Gly Leu Ser Ala Asn Gln Cys Ala Val
            100                 105                 110

Pro Ala Lys Asp Arg Val Asp Cys Gly Tyr Pro His Val Thr Pro Lys
        115                 120                 125

Glu Cys Asn Asn Arg Gly Cys Cys Phe Asp Ser Arg Ile Pro Gly Val
    130                 135                 140

Pro Trp Cys Phe Lys Pro Leu Gln Glu Ala Glu Cys Thr Phe
145                 150                 155

<210> SEQ ID NO 312
<211> LENGTH: 165
<212> TYPE: PRT
<213> ORGANISM: Artificial
<220> FEATURE:
<223> OTHER INFORMATION: synthetic

<400> SEQUENCE: 312

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Leu Ser Ile Ala Ala Lys Glu Glu Gly Val
65                  70                  75                  80

Ser Leu Glu Lys Arg Met Glu Ala Arg Met Phe Trp Leu Leu Val Val
                85                  90                  95

Leu Leu Ala Leu Ala Ser Ser Ser Ala Gly Glu Tyr Val Gly Leu
            100                 105                 110

Ser Ala Asn Gln Cys Ala Val Pro Ala Arg Asp Arg Val Asp Cys Gly
        115                 120                 125

Tyr Pro Gln Val Thr Pro Glu Gln Cys Asn Asn Arg Gly Cys Cys Phe
    130                 135                 140

Asp Ser Ser Ile Pro Gly Val Pro Trp Cys Phe Lys Pro Leu Gln Glu
145                 150                 155                 160

Thr Glu Cys Thr Phe
                165
```

```
<210> SEQ ID NO 313
<211> LENGTH: 165
<212> TYPE: PRT
<213> ORGANISM: Artificial
<220> FEATURE:
<223> OTHER INFORMATION: synthetic

<400> SEQUENCE: 313

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Leu Ser Ile Ala Ala Lys Glu Glu Gly Val
65                  70                  75                  80

Ser Leu Glu Lys Arg Met Glu Ala Arg Val Leu Trp Leu Leu Val Val
                85                  90                  95

Val Leu Val Leu Gly Ser Ser Ser Leu Ala Val Ala Tyr Gln Gly Leu
            100                 105                 110

Ala Thr Asn Leu Cys Glu Val Pro Pro Lys Asp Arg Val Asp Cys Gly
        115                 120                 125

Tyr Pro Glu Ile Thr Ser Glu Gln Cys Val Asn Arg Gly Cys Cys Phe
    130                 135                 140

Asp Ser Ser Ile His Gly Val Pro Trp Cys Phe Lys Pro Leu Gln Asp
145                 150                 155                 160

Thr Glu Cys Arg Phe
                165

<210> SEQ ID NO 314
<211> LENGTH: 166
<212> TYPE: PRT
<213> ORGANISM: Artificial
<220> FEATURE:
<223> OTHER INFORMATION: synthetic

<400> SEQUENCE: 314

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Leu Ser Ile Ala Ala Lys Glu Glu Gly Val
65                  70                  75                  80

Ser Leu Glu Lys Arg Met Glu Thr Arg Ala Phe Trp Thr Thr Leu Leu
                85                  90                  95

Leu Val Leu Val Ala Gly Ser Ser Cys Lys Ala Gln Glu Phe Val Gly
            100                 105                 110

Leu Ser Pro Ser Gln Cys Met Ala Pro Thr Asn Val Arg Val Asp Cys
        115                 120                 125

Asn Tyr Pro Thr Val Thr Ser Glu Gln Cys Asn Asn Arg Gly Cys Cys
```

```
            130                 135                 140
Phe Asp Ser Ser Ile Pro Asn Val Pro Trp Cys Phe Lys Pro Leu Gln
145                 150                 155                 160

Glu Thr Glu Cys Thr Phe
                165

<210> SEQ ID NO 315
<211> LENGTH: 166
<212> TYPE: PRT
<213> ORGANISM: Artificial
<220> FEATURE:
<223> OTHER INFORMATION: synthetic

<400> SEQUENCE: 315

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Leu Ser Ile Ala Ala Lys Glu Glu Gly Val
65                  70                  75                  80

Ser Leu Glu Lys Arg Met Glu Thr Arg Ala Leu Trp Leu Met Leu Leu
                85                  90                  95

Val Val Leu Val Ala Gly Ser Ser Gly Ile Ala Ala Asp Tyr Val Gly
                100                 105                 110

Leu Ser Pro Ser Gln Cys Met Val Pro Ala Asn Val Arg Val Asp Cys
            115                 120                 125

Gly Tyr Pro Ser Val Thr Ser Glu Gln Cys Asn Asn Arg Gly Cys Cys
        130                 135                 140

Phe Asp Ser Ser Ile Pro Asn Val Pro Trp Cys Phe Lys Pro Leu Gln
145                 150                 155                 160

Glu Thr Glu Cys Thr Phe
                165

<210> SEQ ID NO 316
<211> LENGTH: 83
<212> TYPE: PRT
<213> ORGANISM: Artificial
<220> FEATURE:
<223> OTHER INFORMATION: synthetic

<400> SEQUENCE: 316

Met Arg Phe Pro Ser Ile Phe Thr Ala Val Leu Phe Ala Ala Ser Ser
1               5                   10                  15

Ala Leu Ala Ala Leu Glu Lys Arg Glu Glu Tyr Val Gly Leu Ser Ala
                20                  25                  30

Asn Gln Cys Ala Val Pro Ala Lys Asp Arg Val Asp Cys Gly Tyr Pro
            35                  40                  45

His Val Thr Pro Lys Glu Cys Asn Asn Arg Gly Cys Cys Phe Asp Ser
    50                  55                  60

Arg Ile Pro Gly Val Pro Trp Cys Phe Lys Pro Leu Gln Glu Ala Glu
65                  70                  75                  80

Cys Thr Phe
```

-continued

<210> SEQ ID NO 317
<211> LENGTH: 83
<212> TYPE: PRT
<213> ORGANISM: Artificial
<220> FEATURE:
<223> OTHER INFORMATION: synthetic

<400> SEQUENCE: 317

Met Arg Phe Pro Ser Ile Phe Thr Ala Val Leu Phe Ala Ala Ser Ser
1               5                   10                  15

Ala Leu Ala Ala Leu Glu Lys Arg Gly Glu Tyr Val Gly Leu Ser Ala
            20                  25                  30

Asn Gln Cys Ala Val Pro Ala Arg Asp Arg Val Asp Cys Gly Tyr Pro
        35                  40                  45

Gln Val Thr Pro Glu Gln Cys Asn Asn Arg Gly Cys Cys Phe Asp Ser
    50                  55                  60

Ser Ile Pro Gly Val Pro Trp Cys Phe Lys Pro Leu Gln Glu Thr Glu
65                  70                  75                  80

Cys Thr Phe

<210> SEQ ID NO 318
<211> LENGTH: 83
<212> TYPE: PRT
<213> ORGANISM: Artificial
<220> FEATURE:
<223> OTHER INFORMATION: synthetic

<400> SEQUENCE: 318

Met Arg Phe Pro Ser Ile Phe Thr Ala Val Leu Phe Ala Ala Ser Ser
1               5                   10                  15

Ala Leu Ala Ala Leu Glu Lys Arg Val Ala Tyr Gln Gly Leu Ala Thr
            20                  25                  30

Asn Leu Cys Glu Val Pro Pro Lys Asp Arg Val Asp Cys Gly Tyr Pro
        35                  40                  45

Glu Ile Thr Ser Glu Gln Cys Val Asn Arg Gly Cys Cys Phe Asp Ser
    50                  55                  60

Ser Ile His Gly Val Pro Trp Cys Phe Lys Pro Leu Gln Asp Thr Glu
65                  70                  75                  80

Cys Arg Phe

<210> SEQ ID NO 319
<211> LENGTH: 83
<212> TYPE: PRT
<213> ORGANISM: Artificial
<220> FEATURE:
<223> OTHER INFORMATION: synthetic

<400> SEQUENCE: 319

Met Arg Phe Pro Ser Ile Phe Thr Ala Val Leu Phe Ala Ala Ser Ser
1               5                   10                  15

Ala Leu Ala Ala Leu Glu Lys Arg Gln Glu Phe Val Gly Leu Ser Pro
            20                  25                  30

Ser Gln Cys Met Ala Pro Thr Asn Val Arg Val Asp Cys Asn Tyr Pro
        35                  40                  45

Thr Val Thr Ser Glu Gln Cys Asn Asn Arg Gly Cys Cys Phe Asp Ser
    50                  55                  60

Ser Ile Pro Asn Val Pro Trp Cys Phe Lys Pro Leu Gln Glu Thr Glu
65                  70                  75                  80

Cys Thr Phe

<210> SEQ ID NO 320
<211> LENGTH: 83
<212> TYPE: PRT
<213> ORGANISM: Artificial
<220> FEATURE:
<223> OTHER INFORMATION: synthetic

<400> SEQUENCE: 320

```
Met Arg Phe Pro Ser Ile Phe Thr Ala Val Leu Phe Ala Ala Ser Ser
1               5                   10                  15
Ala Leu Ala Ala Leu Glu Lys Arg Ala Asp Tyr Val Gly Leu Ser Pro
            20                  25                  30
Ser Gln Cys Met Val Pro Ala Asn Val Arg Val Asp Cys Gly Tyr Pro
        35                  40                  45
Ser Val Thr Ser Glu Gln Cys Asn Asn Arg Gly Cys Cys Phe Asp Ser
    50                  55                  60
Ser Ile Pro Asn Val Pro Trp Cys Phe Lys Pro Leu Gln Glu Thr Glu
65                  70                  75                  80
Cys Thr Phe
```

<210> SEQ ID NO 321

<400> SEQUENCE: 321

000

<210> SEQ ID NO 322

<400> SEQUENCE: 322

000

<210> SEQ ID NO 323

<400> SEQUENCE: 323

000

<210> SEQ ID NO 324

<400> SEQUENCE: 324

000

<210> SEQ ID NO 325

<400> SEQUENCE: 325

000

<210> SEQ ID NO 326

<400> SEQUENCE: 326

000

<210> SEQ ID NO 327

<400> SEQUENCE: 327

000

<210> SEQ ID NO 328

<400> SEQUENCE: 328

000

<210> SEQ ID NO 329

<400> SEQUENCE: 329

000

<210> SEQ ID NO 330

<400> SEQUENCE: 330

000

<210> SEQ ID NO 331

<400> SEQUENCE: 331

000

<210> SEQ ID NO 332

<400> SEQUENCE: 332

000

<210> SEQ ID NO 333

<400> SEQUENCE: 333

000

<210> SEQ ID NO 334

<400> SEQUENCE: 334

000

<210> SEQ ID NO 335

<400> SEQUENCE: 335

000

<210> SEQ ID NO 336

<400> SEQUENCE: 336

000

<210> SEQ ID NO 337

<400> SEQUENCE: 337

000

<210> SEQ ID NO 338

<400> SEQUENCE: 338

000

<210> SEQ ID NO 339

<400> SEQUENCE: 339

000

<210> SEQ ID NO 340
<400> SEQUENCE: 340
000

<210> SEQ ID NO 341
<400> SEQUENCE: 341
000

<210> SEQ ID NO 342
<400> SEQUENCE: 342
000

<210> SEQ ID NO 343
<400> SEQUENCE: 343
000

<210> SEQ ID NO 344
<400> SEQUENCE: 344
000

<210> SEQ ID NO 345
<400> SEQUENCE: 345
000

<210> SEQ ID NO 346
<400> SEQUENCE: 346
000

<210> SEQ ID NO 347
<400> SEQUENCE: 347
000

<210> SEQ ID NO 348
<400> SEQUENCE: 348
000

<210> SEQ ID NO 349
<400> SEQUENCE: 349
000

<210> SEQ ID NO 350
<400> SEQUENCE: 350
000

-continued

```
<210> SEQ ID NO 351
<400> SEQUENCE: 351
000

<210> SEQ ID NO 352
<400> SEQUENCE: 352
000

<210> SEQ ID NO 353
<400> SEQUENCE: 353
000

<210> SEQ ID NO 354
<400> SEQUENCE: 354
000

<210> SEQ ID NO 355
<400> SEQUENCE: 355
000

<210> SEQ ID NO 356
<400> SEQUENCE: 356
000

<210> SEQ ID NO 357
<400> SEQUENCE: 357
000

<210> SEQ ID NO 358
<400> SEQUENCE: 358
000

<210> SEQ ID NO 359
<400> SEQUENCE: 359
000

<210> SEQ ID NO 360
<400> SEQUENCE: 360
000

<210> SEQ ID NO 361
<400> SEQUENCE: 361
000
```

-continued

<210> SEQ ID NO 362
<400> SEQUENCE: 362
000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<400> SEQUENCE: 370
000

<210> SEQ ID NO 371
<400> SEQUENCE: 371
000

<210> SEQ ID NO 372
<400> SEQUENCE: 372
000

<210> SEQ ID NO 373

-continued

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<400> SEQUENCE: 388

000

<210> SEQ ID NO 389

<400> SEQUENCE: 389

000

<210> SEQ ID NO 390

<400> SEQUENCE: 390

000

<210> SEQ ID NO 391

<400> SEQUENCE: 391

000

<210> SEQ ID NO 392

<400> SEQUENCE: 392

000

<210> SEQ ID NO 393

<400> SEQUENCE: 393

000

<210> SEQ ID NO 394

<400> SEQUENCE: 394

000

<210> SEQ ID NO 395

<400> SEQUENCE: 395

000

<210> SEQ ID NO 396

<400> SEQUENCE: 396

000

<210> SEQ ID NO 397

<400> SEQUENCE: 397

000

<210> SEQ ID NO 398

<400> SEQUENCE: 398

000

<210> SEQ ID NO 399

<400> SEQUENCE: 399

000

<210> SEQ ID NO 400

<400> SEQUENCE: 400

000

<210> SEQ ID NO 401
<211> LENGTH: 4
<212> TYPE: PRT
<213> ORGANISM: Artificial
<220> FEATURE:
<223> OTHER INFORMATION: synthetic

<400> SEQUENCE: 401

Leu Glu Lys Arg
1

<210> SEQ ID NO 402
<211> LENGTH: 61
<212> TYPE: PRT
<213> ORGANISM: Artificial
<220> FEATURE:
<223> OTHER INFORMATION: synthetic

<400> SEQUENCE: 402

Glu Ala Glu Glu Tyr Val Gly Leu Ser Ala Asn Gln Cys Ala Val Pro
1               5                   10                  15

Ala Lys Asp Arg Val Asp Cys Gly Tyr Pro His Val Thr Pro Lys Glu
            20                  25                  30

Cys Asn Asn Arg Gly Cys Cys Phe Asp Ser Arg Ile Pro Gly Val Pro
        35                  40                  45

Trp Cys Phe Lys Pro Leu Gln Glu Ala Glu Cys Thr Phe
    50                  55                  60

<210> SEQ ID NO 403
<211> LENGTH: 59
<212> TYPE: PRT
<213> ORGANISM: Artificial
<220> FEATURE:
<223> OTHER INFORMATION: synthetic

<400> SEQUENCE: 403

```
Glu Glu Tyr Val Gly Leu Ser Ala Asn Gln Cys Ala Val Pro Ala Lys
1               5                   10                  15

Asp Arg Val Asp Cys Gly Tyr Pro His Val Thr Pro Lys Glu Cys Asn
                20                  25                  30

Asn Arg Gly Cys Cys Phe Asn Ser Arg Ile Pro Gly Val Pro Trp Cys
                35                  40                  45

Phe Lys Pro Leu Gln Glu Ala Glu Cys Thr Pro
    50                  55

<210> SEQ ID NO 404
<211> LENGTH: 10
<212> TYPE: PRT
<213> ORGANISM: Artificial
<220> FEATURE:
<223> OTHER INFORMATION: synthetic

<400> SEQUENCE: 404

Leu Glu Lys Arg Glu Ala Glu Glu Tyr Val
1               5                   10

<210> SEQ ID NO 405
<211> LENGTH: 22
<212> TYPE: PRT
<213> ORGANISM: Artificial
<220> FEATURE:
<223> OTHER INFORMATION: synthetic

<400> SEQUENCE: 405

Met Arg Phe Pro Ser Ile Phe Thr Ala Val Leu Phe Ala Ala Ser Ser
1               5                   10                  15

Ala Leu Ala Ala Leu Glu
            20
```